(12) United States Patent
Beers

(10) Patent No.: US 11,166,525 B2
(45) Date of Patent: *Nov. 9, 2021

(54) FOOTWEAR HAVING REMOVABLE MOTORIZED ADJUSTMENT SYSTEM

(71) Applicant: NIKE, Inc., Beaverton, OR (US)

(72) Inventor: Tiffany A. Beers, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/640,282

(22) Filed: Jun. 30, 2017

(65) Prior Publication Data
US 2017/0295889 A1 Oct. 19, 2017

Related U.S. Application Data

(63) Continuation of application No. 14/032,524, filed on Sep. 20, 2013, now Pat. No. 9,693,605, which is a
(Continued)

(51) Int. Cl.
*A43C 11/00* (2006.01)
*B65H 59/38* (2006.01)
(Continued)

(52) U.S. Cl.
CPC .......... *A43C 11/165* (2013.01); *A43B 3/0005* (2013.01); *A43B 3/0015* (2013.01);
(Continued)

(58) Field of Classification Search
CPC ..... A43C 11/00; A43C 11/008; A43C 11/165; Y10T 24/2183; Y10T 24/2187
See application file for complete search history.

(56) References Cited

U.S. PATENT DOCUMENTS

| 1,702,583 A | 2/1929 | Isiah |
| 1,916,483 A | 7/1933 | Ora |

(Continued)

FOREIGN PATENT DOCUMENTS

| CN | 1061706 A | 6/1992 |
| CN | 1550166 A | 12/2004 |

(Continued)

OTHER PUBLICATIONS

"U.S. Appl. No. 14/014,555, Examiner Interview Summary dated Jan. 22, 2016", 3 pgs.
(Continued)

*Primary Examiner* — Jila M Mohandesi
(74) *Attorney, Agent, or Firm* — Schwegman Lundberg & Woessner, P.A.

(57) ABSTRACT

An article of footwear may include a motorized tensioning system. The tensioning system may include a tensile member and a motorized tightening device configured to apply tension in the tensile member to adjust the size of an internal void defined by the article of footwear. The tensioning system may further include a power source configured to supply power to the motorized tightening device. The tensile member, the motorized tightening device, and the power source may be configured to be removably attached to the article of footwear.

20 Claims, 40 Drawing Sheets

Related U.S. Application Data continuation-in-part of application No. 14/014,555, filed on Aug. 30, 2013, now Pat. No. 9,365,387.

(60) Provisional application No. 61/695,953, filed on Aug. 31, 2012.

(51) Int. Cl.

| | | |
|---|---|---|
| *A43C 11/16* | (2006.01) | |
| *B65H 59/00* | (2006.01) | |
| *A43B 11/00* | (2006.01) | |
| *A43B 3/00* | (2006.01) | |
| *A61F 5/02* | (2006.01) | |
| *B65H 69/00* | (2006.01) | |

(52) U.S. Cl.
CPC .............. *A43B 11/00* (2013.01); *A43C 11/00* (2013.01); *A43C 11/008* (2013.01); *A61F 5/028* (2013.01); *B65H 59/00* (2013.01); *B65H 59/384* (2013.01); *B65H 69/00* (2013.01)

(56) References Cited

U.S. PATENT DOCUMENTS

| | | | |
|---|---|---|---|
| 3,187,342 A | 6/1965 | Aileo | |
| 3,430,303 A | 3/1969 | Perrin et al. | |
| 3,481,557 A * | 12/1969 | Miller | B66D 1/34 242/395 |
| 3,549,878 A | 12/1970 | Bailey | |
| 3,859,496 A | 1/1975 | Giese | |
| 4,011,634 A | 3/1977 | Olivieri | |
| 4,020,571 A | 5/1977 | Olivieri | |
| 4,037,333 A | 7/1977 | Olivieri | |
| 4,090,278 A | 5/1978 | Olivieri | |
| 4,130,949 A | 12/1978 | Seidel | |
| 4,253,217 A | 3/1981 | Marzocchi | |
| 4,310,951 A | 1/1982 | Riedel | |
| 4,326,320 A | 4/1982 | Riedel | |
| 4,424,636 A | 1/1984 | Everest | |
| 4,433,456 A * | 2/1984 | Baggio | A43C 11/16 24/68 B |
| 4,453,290 A | 6/1984 | Riedel | |
| 4,602,822 A * | 7/1986 | Kim | B62K 25/02 280/229 |
| 4,619,057 A | 10/1986 | Sartor et al. | |
| 4,644,938 A | 2/1987 | Yates et al. | |
| 4,667,896 A * | 5/1987 | Frey | B65H 75/18 242/118.41 |
| 4,697,360 A | 10/1987 | Sartor | |
| 4,724,626 A | 2/1988 | Baggio | |
| 4,741,115 A | 5/1988 | Pozzobon | |
| 4,780,968 A | 11/1988 | Bragagnolo | |
| 4,787,124 A | 11/1988 | Pozzobon et al. | |
| 4,800,659 A | 1/1989 | Marega | |
| 4,802,290 A | 2/1989 | Marega | |
| 4,841,649 A | 6/1989 | Baggio et al. | |
| 4,942,678 A | 7/1990 | Gumbert | |
| 5,105,566 A | 4/1992 | Legon | |
| 5,129,130 A | 7/1992 | Lecouturier | |
| 5,157,813 A | 10/1992 | Carroll | |
| 5,170,732 A * | 12/1992 | Gordon | D05B 57/28 112/256 |
| 5,186,411 A * | 2/1993 | Fanning | B65H 75/406 242/405.3 |
| 5,341,583 A | 8/1994 | Hallenbeck | |
| 5,381,609 A | 1/1995 | Hieblinger | |
| 5,425,185 A | 6/1995 | Gansler | |
| 5,456,393 A | 10/1995 | Mathis et al. | |
| 5,467,537 A | 11/1995 | Aveni et al. | |
| 5,469,640 A | 11/1995 | Nichols | |
| 5,495,682 A | 3/1996 | Chen | |
| 5,555,650 A | 9/1996 | Longbottom et al. | |
| 5,692,324 A | 12/1997 | Goldston et al. | |
| 5,695,148 A * | 12/1997 | Christensen | B65H 75/18 242/405.3 |
| 5,755,044 A | 5/1998 | Veylupek | |
| 5,791,068 A | 8/1998 | Bernier et al. | |
| 5,836,899 A | 11/1998 | Reilly | |
| 5,839,210 A * | 11/1998 | Bernier | A43B 1/0072 36/50.1 |
| 5,934,599 A * | 8/1999 | Hammerslag | A43C 1/00 242/396.1 |
| 6,015,110 A * | 1/2000 | Lai | B65H 75/28 242/388.1 |
| 6,018,890 A | 2/2000 | Bowen | |
| 6,032,387 A | 3/2000 | Johnson | |
| 6,052,924 A | 4/2000 | Sabat | |
| 6,148,489 A | 11/2000 | Dickie et al. | |
| 6,202,953 B1 | 3/2001 | Hammerslag | |
| 6,289,558 B1 | 9/2001 | Hammerslag | |
| 6,289,609 B1 | 9/2001 | Bowen | |
| 6,390,519 B1 * | 5/2002 | Dreisbach | G09F 3/0364 242/388.1 |
| 6,427,361 B1 | 8/2002 | Chou | |
| 6,449,878 B1 | 9/2002 | Lyden | |
| 6,467,194 B1 | 10/2002 | Johnson | |
| 6,601,042 B1 | 7/2003 | Lyden | |
| 6,681,504 B2 | 1/2004 | Kinan | |
| 6,691,433 B2 * | 2/2004 | Liu | A43B 3/0005 24/68 SK |
| 6,691,443 B1 | 2/2004 | Slayden | |
| 6,751,490 B2 | 6/2004 | Esenaliev et al. | |
| 6,862,820 B2 | 3/2005 | Farys et al. | |
| 6,892,429 B2 | 5/2005 | Sartor et al. | |
| 6,896,128 B1 | 5/2005 | Johnson | |
| 6,922,917 B2 | 8/2005 | Kerns et al. | |
| 7,017,848 B2 * | 3/2006 | Fleming | B65H 75/406 242/395 |
| 7,065,906 B2 | 6/2006 | Jones et al. | |
| 7,096,559 B2 | 8/2006 | Johnson | |
| 7,103,994 B2 | 9/2006 | Johnson | |
| 7,200,957 B2 | 4/2007 | Hubbard et al. | |
| 7,287,342 B2 | 10/2007 | Keen | |
| 7,310,895 B2 | 12/2007 | Whittlesey et al. | |
| 7,367,522 B2 | 5/2008 | Chen | |
| 7,503,131 B2 * | 3/2009 | Nadel | A43B 5/0415 36/117.1 |
| 7,584,528 B2 * | 9/2009 | Hu | A43C 11/16 24/68 SK |
| 7,591,050 B2 | 9/2009 | Hammerslag | |
| 7,676,960 B2 | 3/2010 | Dibenedetto et al. | |
| 7,721,468 B1 * | 5/2010 | Johnson | A43C 1/06 36/118.1 |
| 7,752,774 B2 | 7/2010 | Ussher | |
| 7,950,112 B2 | 5/2011 | Hammerslag et al. | |
| 7,954,204 B2 | 6/2011 | Hammerslag et al. | |
| 7,980,009 B2 | 7/2011 | Carnes et al. | |
| 7,992,261 B2 | 8/2011 | Hammerslag et al. | |
| 8,020,320 B2 | 9/2011 | Gillespie | |
| 8,046,937 B2 | 11/2011 | Beers et al. | |
| 8,056,269 B2 | 11/2011 | Beers et al. | |
| 8,061,061 B1 | 11/2011 | Rivas | |
| 8,074,379 B2 | 12/2011 | Robinson et al. | |
| 8,091,182 B2 | 1/2012 | Hammerslag et al. | |
| 8,141,277 B2 | 3/2012 | Robinson et al. | |
| 8,151,490 B2 | 4/2012 | Sokolowski | |
| 8,231,074 B2 | 7/2012 | Hu et al. | |
| 8,387,282 B2 | 3/2013 | Baker et al. | |
| 8,434,200 B2 * | 5/2013 | Chen | A43C 11/165 2/418 |
| 8,904,673 B2 | 12/2014 | Johnson et al. | |
| 9,365,387 B2 | 6/2016 | Beers et al. | |
| 9,693,605 B2 | 7/2017 | Beers | |
| 9,861,164 B2 * | 1/2018 | Beers | A43B 3/0005 |
| 10,046,942 B2 | 8/2018 | Beers et al. | |
| 11,000,099 B2 | 5/2021 | Beers et al. | |
| 11,044,968 B2 | 6/2021 | Beers | |
| 2002/0043007 A1 | 4/2002 | Hannah | |
| 2002/0095750 A1 | 7/2002 | Hammerslag | |
| 2003/0204938 A1 * | 11/2003 | Hammerslag | A43C 11/004 24/68 SK |

(56) References Cited

U.S. PATENT DOCUMENTS

| | | |
|---|---|---|
| 2004/0128863 A1 | 7/2004 | Hong et al. |
| 2005/0098673 A1 | 5/2005 | Huang |
| 2005/0102861 A1 | 5/2005 | Martin |
| 2005/0160627 A1 | 7/2005 | Dalgaard et al. |
| 2006/0000116 A1 | 1/2006 | Brewer |
| 2006/0053845 A1* | 3/2006 | Benda .............. E05B 67/006 70/18 |
| 2006/0116483 A1 | 6/2006 | Tonkel |
| 2006/0156517 A1 | 7/2006 | Hammerslag et al. |
| 2006/0201031 A1 | 9/2006 | Jones et al. |
| 2007/0000105 A1 | 1/2007 | Grande et al. |
| 2007/0006489 A1 | 1/2007 | Case et al. |
| 2007/0011914 A1 | 1/2007 | Keen et al. |
| 2007/0043630 A1 | 2/2007 | Lyden |
| 2007/0169378 A1 | 7/2007 | Sodeberg et al. |
| 2007/0278911 A1 | 12/2007 | Vallance et al. |
| 2008/0060167 A1 | 3/2008 | Hammerslag et al. |
| 2008/0066272 A1 | 3/2008 | Hammerslag et al. |
| 2008/0222917 A1 | 9/2008 | Dojan et al. |
| 2008/0235990 A1 | 10/2008 | Wegener |
| 2008/0307673 A1 | 12/2008 | Johnson |
| 2009/0039191 A1* | 2/2009 | Yen .............. B65H 75/4431 242/378.2 |
| 2009/0055044 A1 | 2/2009 | Dienst |
| 2009/0184189 A1 | 7/2009 | Soderberg et al. |
| 2009/0205221 A1 | 8/2009 | Mitchell |
| 2009/0272007 A1* | 11/2009 | Beers .............. A43B 3/0005 36/50.1 |
| 2009/0313853 A1 | 12/2009 | Tadin |
| 2010/0101116 A1 | 4/2010 | Serafino et al. |
| 2010/0139057 A1* | 6/2010 | Soderberg .......... A43C 11/16 24/68 R |
| 2010/0251524 A1* | 10/2010 | Chen .............. A43C 7/00 24/713.2 |
| 2010/0299959 A1 | 12/2010 | Hammerslag et al. |
| 2011/0175744 A1 | 7/2011 | Englert et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005923 A1 | 1/2012 | Beers et al. |
| 2012/0117821 A1 | 5/2012 | Adams et al. |
| 2012/0192457 A1 | 8/2012 | Youngs |
| 2013/0312293 A1 | 11/2013 | Gerber |
| 2014/0068838 A1 | 3/2014 | Beers et al. |
| 2014/0070042 A1 | 3/2014 | Beers et al. |
| 2014/0082963 A1 | 3/2014 | Beers |
| 2014/0094728 A1 | 4/2014 | Soderberg et al. |
| 2016/0272458 A1 | 9/2016 | Beers et al. |
| 2016/0345681 A1 | 12/2016 | Pheil et al. |
| 2018/0317609 A1 | 11/2018 | Beers et al. |
| 2020/0281321 A1 | 9/2020 | Beers et al. |
| 2020/0329821 A1 | 10/2020 | Beers |
| 2021/0022451 A1 | 1/2021 | Beers et al. |
| 2021/0022452 A1 | 1/2021 | Beers et al. |

FOREIGN PATENT DOCUMENTS

| | | | |
|---|---|---|---|
| CN | 102014682 | A | 4/2011 |
| CN | 104582519 | A | 4/2015 |
| CN | 104822284 | A | 8/2015 |
| CN | 105722419 | A | 6/2016 |
| CN | 104822284 | B | 10/2016 |
| CN | 106820446 | A | 6/2017 |
| CN | 105722419 | B | 6/2018 |
| CN | 108652118 | A | 10/2018 |
| CN | 106820446 | B | 4/2019 |
| DE | 29817003 | U1 | 3/1999 |
| DE | 19833801 | A1 | 2/2000 |
| DE | 10109673 | A1 | 9/2002 |
| DE | 102005036013 | A1 | 2/2007 |
| EP | 1064863 | A1 | 1/2001 |
| EP | 1530913 | A1 | 5/2005 |
| EP | 3046434 | B1 | 5/2019 |
| EP | 2871994 | | 8/2020 |
| FR | 2827486 | A1 | 1/2003 |
| GB | 2449722 | A | 12/2008 |
| JP | 2004222782 | A | 8/2004 |
| JP | 2005036374 | A | 2/2005 |
| JP | 2005124597 | A | 5/2005 |
| JP | 2010148927 | A | 7/2010 |
| JP | 2011519611 | A | 7/2011 |
| JP | 2013529504 | A | 7/2013 |
| JP | 2016530058 | A | 9/2016 |
| JP | 6581989 | B2 | 9/2019 |
| TW | 521593 | U | 2/2003 |
| WO | WO-0115559 | A1 | 3/2001 |
| WO | WO-2009071652 | A1 * | 6/2009 ........ A43C 11/008 |
| WO | WO-2009071652 | A1 | 6/2009 |
| WO | WO-2009134858 | A1 | 11/2009 |
| WO | WO-2014036371 | A1 | 3/2014 |
| WO | WO-2014036374 | A1 | 3/2014 |

OTHER PUBLICATIONS

"U.S. Appl. No. 14/014,555, Non Final Office Action dated Aug. 26, 2015", 8 pgs.

"U.S. Appl. No. 14/014,555, Notice of Allowance dated Feb. 17, 2016", 7 pgs.

"U.S. Appl. No. 14/014,555, Response filed Jan. 26, 2016 to Non Final Office Action dated Aug. 26, 2015", 14 pgs.

"U.S. Appl. No. 14/014,555, Response filed Aug. 14, 2015 to Restriction Requirement dated May 15, 2015", 11 pgs.

"U.S. Appl. No. 14/014,555, Restriction Requirement dated May 15, 2015", 7 pgs.

"U.S. Appl. No. 14/032,524 Notice of Allowance dated Nov. 23, 2016", 7 pgs.

"U.S. Appl. No. 14/032,524, Examiner Interview Summary dated Mar. 3, 2016", 3 pgs.

"U.S. Appl. No. 14/032,524, Final Office Action dated May 6, 2016", 6 pgs.

"U.S. Appl. No. 14/032,524, Non Final Office Action dated Dec. 9, 2015", 11 pgs.

"U.S. Appl. No. 14/032,524, Notice of Allowability dated May 22, 2017", 2 pgs.

"U.S. Appl. No. 14/032,524, Notice of Allowance dated Mar. 30, 2017", 8 pgs.

"U.S. Appl. No. 14/032,524, Notice of Allowance dated Jul. 26, 2016", 8 pgs.

"U.S. Appl. No. 14/032,524, Response filed Mar. 9, 2016 to Non Final Office Action dated Dec. 9, 2015", 14 pgs.

"U.S. Appl. No. 14/032,524, Response filed Jul. 6, 2016 to Final Office Action dated May 6, 2016", 11 pgs.

"U.S. Appl. No. 14/032,524, Response filed Oct. 6, 2015 to Restriction Requirement dated Aug. 7, 2015", 11 pgs.

"U.S. Appl. No. 14/032,524, Restriction Requirement dated Aug. 7, 2015", 8 pgs.

"Chinese Application Serial No. 201380044810.0, Office Action dated Dec. 2, 2015", with English translation of claims, 14 pgs.

"Chinese Application Serial No. 201380044810.0, Response filed Apr. 18, 2016", 72 pgs.

"Chinese Application Serial No. 201380044810.0, Response filed Apr. 18, 2016 to Office Action dated Dec. 2, 2015", with English translation of claims, 21 pgs.

"Chinese Application Serial No. 201380044813.4, Notice of Allowance dated May 23, 2016", 73 pgs.

"Chinese Application Serial No. 201480062685.0, Office Action dated Mar. 2, 2017", with English translation of claims, 14 pgs.

"Chinese Application Serial No. 201480062685.0, Voluntary Amendment filed Oct. 21, 2016", 201 pgs.

"European Application Serial No. 13783413.1, Response filed Sep. 7, 2015 to Written Opinion and Voluntary Amendments dated Mar. 11, 2015", 18 pgs.

"European Application Serial No. 13783414.9, Communication Pursuant to Article 94(3) EPC dated May 23, 2017", 5 pgs.

(56) References Cited

OTHER PUBLICATIONS

"European Application Serial No. 13783414.9, Response filed Sep. 7, 2015 to Communication pursuant to Rules 161(1) and 162 EPC dated Mar. 10, 2015", 14 pgs.
"European Application Serial No. 14790802.4, Response filed Nov. 3, 2016", 19 pgs.
"International Application Serial No. PCT/US2013/057462, International Preliminary Report on Patentability dated Mar. 12, 2015", 9 pgs.
"International Application Serial No. PCT/US2013/057462, International Search Report dated Jan. 3, 2014", 5 pgs.
"International Application Serial No. PCT/US2013/057462, Written Opinion dated Jan. 3, 2014", 7 pgs.
"International Application Serial No. PCT/US2013/057467, International Preliminary Report on Patentability dated Mar. 12, 2015", 9 pgs.
"International Application Serial No. PCT/US2013/057467, International Search Report dated Jan. 3, 2014", 5 pgs.
"International Application Serial No. PCT/US2013/057467, Written Opinion dated Jan. 3, 2014", 7 pgs.
"International Application Serial No. PCT/US2014/056207, International Preliminary Report on Patentability dated Mar. 31, 2016", 10 pgs.
"International Application Serial No. PCT/US2014/056207, International Search Report dated Dec. 22, 2014", 3 pgs.
"International Application Serial No. PCT/US2014/056207, Written Opinion dated Dec. 22, 2014", 7 pgs.
"Japanese Application Serial No. 2016-543980, Office Action dated May 13, 2016", 87 pgs.
Blake, Bevin, "About the Project", Power-Laces.com Archived, [Online]. Retrieved from the Internet: <URL: http://web.archive.org/web/20120818223427/http://www.power-laces.com>, (Aug. 18, 2012), 2 pgs.
Blake, Bevin, "Power Laces Prototype Version 1", [Online] retrieved from the internet: <http://www.youtube.com/watch?v=ROEZsOHpFQc&feature=endscreen&NR=1>, (Uploaded Jul. 4, 2010), 3 pgs.
Blake, Bevin, "Power Laces Prototype Version 2", [Online] retrieved from the internet: <http://www.youtube.com/watch?v=k Efr2TaEPo>, (Aug. 29, 2010), 7 pgs.
"U.S. Appl. No. 15/171,500, Notice of Allowability dated Jul. 5, 2018", 2 pgs.
"U.S. Appl. No. 15/171,500, Notice of Allowability dated Jul. 19, 2018", 2 pgs.
"Chinese Application Serial No. 201610836651.3, Office Action dated May 24, 2018", w/English Translation, 6 pgs.
"European Application Serial No. 13783414.9, Communication Pursuant to Article 94(3) EPC dated Jul. 24, 2018", 6 pgs.
"European Application Serial No. 13783414.9, Response filed Sep. 12, 2017 to Communication Pursuant to Article 94(3) EPC dated May 23, 2017", 15 pgs.
"European Application Serial No. 14790802.4, Response filed Aug. 21, 2018 to Communication Pursuant to Article 94(3) EPC dated Apr. 11, 2018", 15 pgs.
"Japanese Application Serial No. 2016-543980, Office Action dated Jun. 21, 2018", w/ English translation, 8 pgs.
"Chinese Application Serial No. 201480062685.0, Office Action dated Sep. 15, 2017", w/ English Translation, 20 pgs.
"Chinese Application Serial No. 201480062685.0, Response filed Jul. 17, 2017 to Office Action dated Mar. 2, 2017", w/ English Translation, 8 pgs.
"Chinese Application Serial No. 201480062685.0, Response filed Dec. 22, 2017 to Office Action dated Sep. 15, 2017", claims not amended in response, attached currently pending claims to response PDF, 13 pgs.
"Japanese Application Serial No. 2016-543980, Office Action dated Jan. 25, 2018", w/ English translation, 9 pgs.
"U.S. Appl. No. 15/171,500, Notice of Allowability dated Apr. 18, 2018", 2 pgs.
"U.S. Appl. No. 15/171,500, Notice of Allowance dated Apr. 10, 2018", 7 pgs.
"European Application Serial No. 14790802.4, Communication Pursuant to Article 94(3) EPC dated Apr. 11, 2018", 7 pgs.
"Japanese Application Serial No. 2016-543980, Response filed Mar. 29, 2018 to Office Action dated Jan. 25, 2018", w/ English claims, 11 pgs.
"Chinese Application Serial No. 201610836651.3, Response filed Nov. 8, 2018 to Office Action dated May 24, 2018", w/ English claims, 9 pgs.
"Japanese Application Serial No. 2016-543980, Response filed Nov. 21, 2018 to Office Action dated Jun. 21, 2018", w/ English claims, 13 pgs.
"European Application Serial No. 13783414.9, Response filed Jan. 30, 2019 to Communication Pursuant to Article 94(3) EPC dated Jul. 24, 2018", 14 pgs.
"Japanese Application Serial No. 2016-543980, Examiners Decision of Final Refusal dated Dec. 20, 2018", W/ English Translation, 10 pgs.
"Chinese Application Serial No. 201910272193.9, Office Action dated Jul. 24, 2019", 1 pg.
"Japanese Application Serial No. 2016-543980, Appeal of an Adverse Desicion filed Mar. 28, 2019 to Examiners Decision of Final Refusal dated Dec. 20, 2018", w/ English claims, 13 pgs.
"European Application Serial No. 13783414.9, Communication Pursuant to Article 94(3) dated Aug. 5, 2019", also listed on EPO website as an examiner telephone interview, 4 pgs.
"European Application Serial No. 13783414.9, Examiner Interview Summary dated Nov. 21, 2019", 3 pgs.
"European Application Serial No. 13783414.9, Response filed Jan. 16, 2020 to Examiner Interview Summary dated Nov. 21, 2019", 13 pgs.
"European Application Serial No. 19175382.1, Extended European Search Report dated Dec. 12, 2019", 10 pgs.
"U.S. Appl. No. 16/037,334, Non Final Office Action dated May 7, 2020", 12 pgs.
"U.S. Appl. No. 16/884,427, Non Final Office Action dated Jun. 29, 2020".
"Chinese Application Serial No. 2018104506951, Office Action dated Apr. 3, 2020", w/o English translation, 6 pgs.
"U.S. Appl. No. 16/037,334, Advisory Action dated Nov. 3, 2020", 3 pgs.
"U.S. Appl. No. 16/037,334, Response filed Oct. 26, 2020 to Final Office Action dated Aug. 26, 2020", 9 pgs.
"U.S. Appl. No. 16/884,427, Ex Parte Quayle Action mailed Oct. 20, 2020", 5 pgs.
"U.S. Appl. No. 17/070,298, Preliminary Amendment filed Oct. 15, 2020", 7 pgs.
"European Application Serial No. 19175382.1, Communication Pursuant to Article 94(3) EPC dated Aug. 31, 2020", 7 pgs.
"European Application Serial No. 19175382.1, Response filed Jul. 15, 2020 to Extended European Search Report dated Dec. 12, 2019", 15 pgs.
"Chinese Application Serial No. 2018104506951, Response filed Aug. 3, 2020 to Office Action dated Apr. 3, 2020", w English claims, 14 pgs.
"U.S. Appl. No. 16/884,427, Examiner Interview Summary dated Jul. 21, 2020".
"U.S. Appl. No. 16/916,943, Restriction Requirement dated Jul. 27, 2020", 8 pgs.
"U.S. Appl. No. 16/037,334, Response filed Aug. 6, 2020 to Non Final Office Action dated May 7, 2020", 9 pgs.
"U.S. Appl. No. 16/916,943, Response filed Sep. 25, 2020 to Restriction Requirement dated Jul. 27, 2020", 8 pgs.
"U.S. Appl. No. 16/037,334, Final Office Action dated Aug. 26, 2020", 9 pgs.
"U.S. Appl. No. 16/884,427, Response filed Sep. 29, 2020 to Non Final Office Action dated Jun. 29, 2020", 11 pgs.
"U.S. Appl. No. 16/037,334, Non Final Office Action dated Mar. 11, 2021", 6 pgs.
"U.S. Appl. No. 16/884,427, Supplemental Notice of Allowability dated Apr. 13, 2021", 2 pgs.
"U.S. Appl. No. 16/916,943, Notice of Allowance dated Feb. 26, 2021", 14 pgs.

(56) References Cited

OTHER PUBLICATIONS

"U.S. Appl. No. 16/916,943, Response filed Feb. 18, 2021 to Non Final Office Action dated Jan. 13, 2021", 8 pgs.

"U.S. Appl. No. 16/916,943, Supplemental Notice of Allowability dated Jan. 4, 2021", 2 pgs.

"U.S. Appl. No. 17/070,387, Advisory Action dated May 17, 2021", 3 pgs.

"U.S. Appl. No. 17/070,387, Final Office Action dated Mar. 9, 2021", 7 pgs.

"U.S. Appl. No. 17/070,387, Response filed Feb. 26, 2021 to Non Final Office Action dated Nov. 30, 2020", 7 pgs..

"U.S. Appl. No. 17/070,387, Response filed May 10, 2021 to Final Office Action dated Mar. 9, 2021", 7 pgs.

"Chinese Application Serial No. 201810450695.1, Response filed Mar. 26, 2021 to Office Action dated Nov. 11, 2020". w/ English claims, 23 pgs.

"European Application Serial No. 19175382.1, Communication Pursuant to Article 94(3) EPC dated Mar. 16, 2021", 4 pgs.

"European Application Serial No. 19175382.1, Response filed Feb. 11, 2021 to Communication Pursuant to Article 94(3) EPC dated Aug. 31, 2020", 6 pgs.

"European Application Serial No. 20192754.8, Extended European Search Report dated Mar. 16, 2021", 6 pgs.

"U.S. Appl. No. 17/070,387, Non Final Office Action dated Nov. 30, 2020".

"Chinese Application Serial No. 201810450695.1, Office Action dated Nov. 11, 2020", w English Translation, 18 pgs.

"U.S. Appl. No. 16/884,427, Response filed Dec. 17, 2020 to Ex Parte Quayle Action mailed Oct. 20, 2020", 11 pgs.

"U.S. Appl. No. 17/070,387, Examiner Interview Summary dated Dec. 28, 2020", 3 pgs.

"U.S. Appl. No. 16/884,427, Notice of Allowance dated Jan. 6, 2021", 5 pgs.

"U.S. Appl. No. 16/916,943, Non Final Office Action dated Jan. 13, 2021", 10 pgs.

"U.S. Appl. No. 16/037,334, Notice of Allowance dated Jul. 29, 2021", 7 pgs.

"U.S. Appl. No. 16/037,334, Response filed Jul. 15, 2021 to Non Final Office Action dated Mar. 11, 2021", 8 pgs.

"European Application Serial No. 19175382.1, Communication Pursuant to Article 94(3) EPC dated Jul. 7, 2021", 5 pgs.

"Chinese Application Serial No. 201810450695.1, Office Action dated Jul. 8, 2021", With English translation, 16 pages.

\* cited by examiner

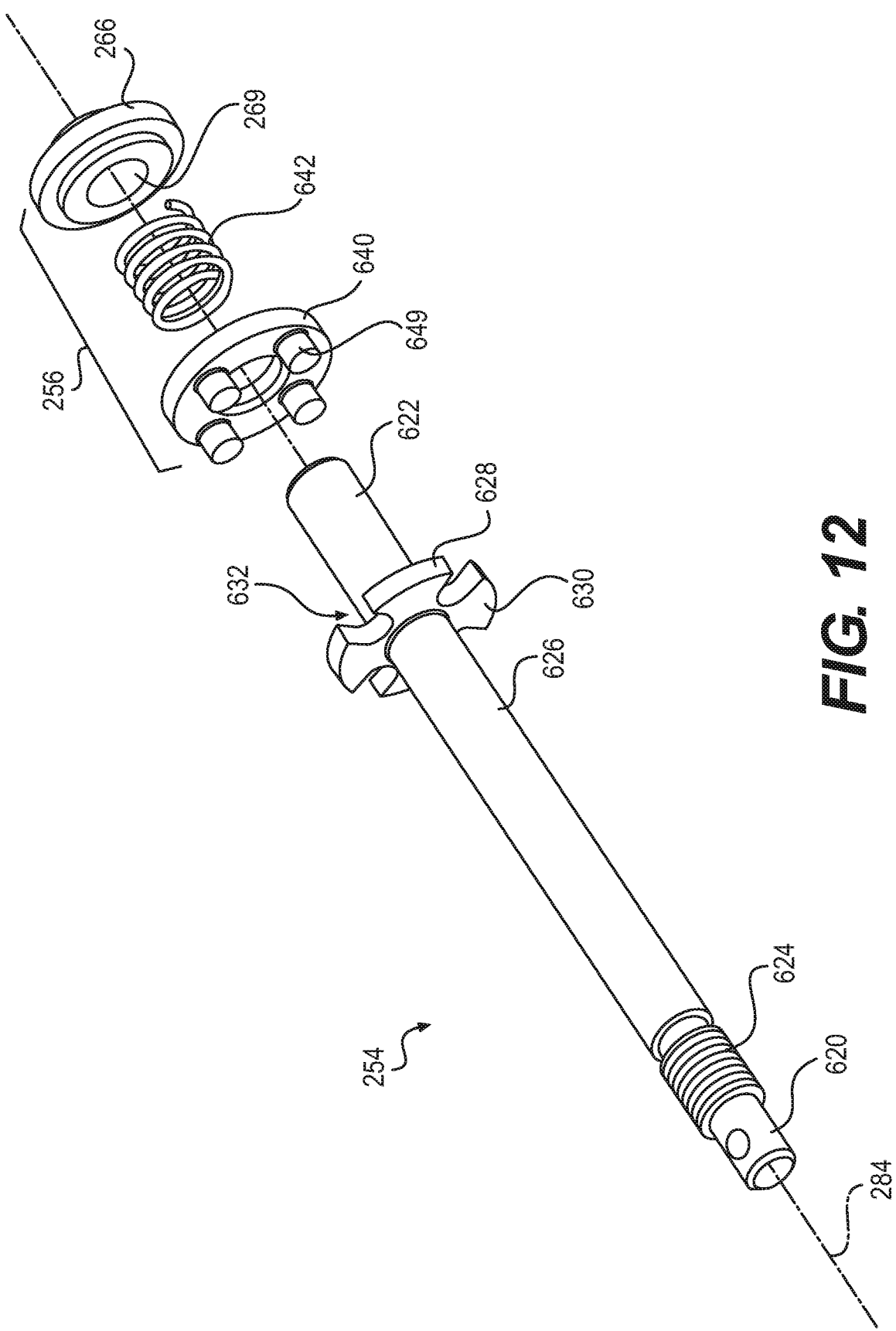

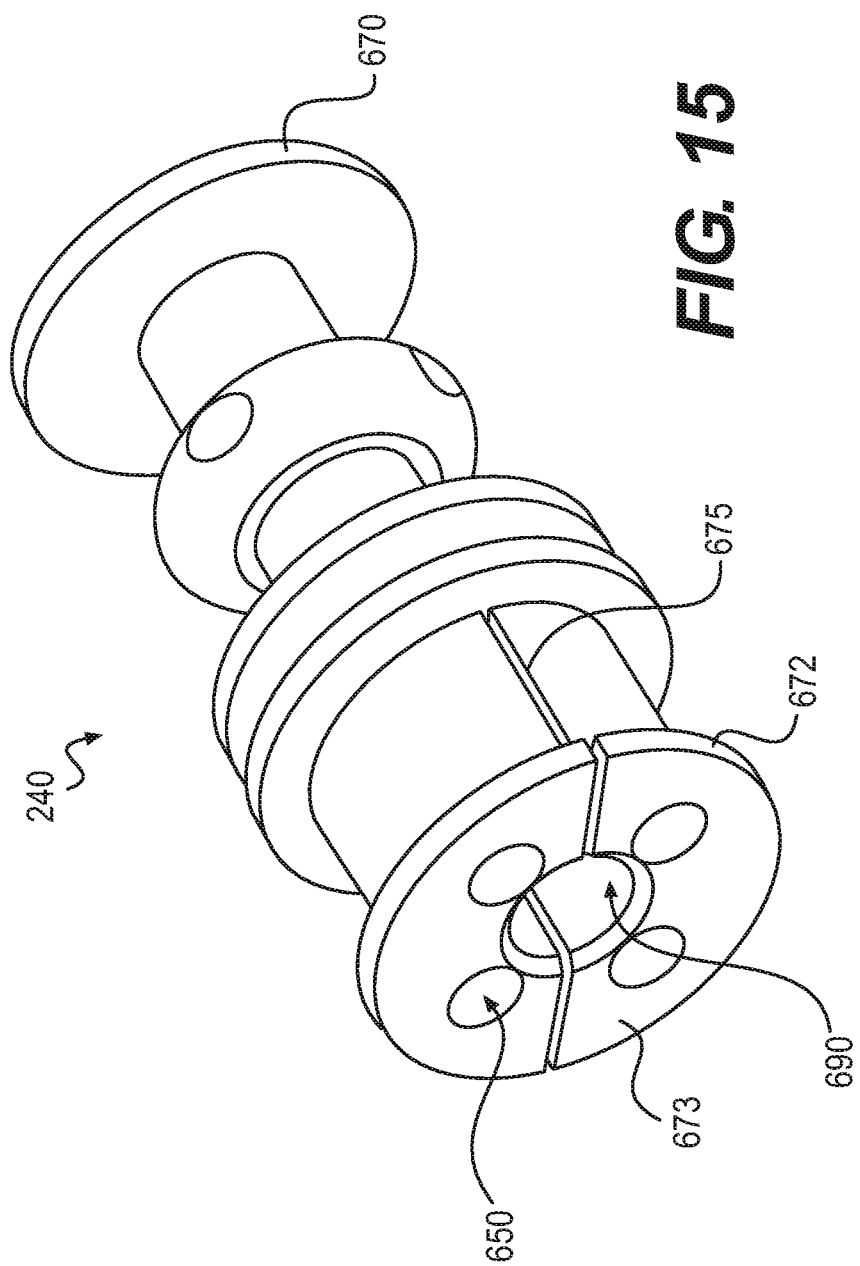

FOOTWEAR HAVING REMOVABLE MOTORIZED ADJUSTMENT SYSTEM

CROSS REFERENCE TO RELATED APPLICATIONS

This application is a continuation of U.S. patent application Ser. No. 14/032,524, filed on Sep. 20, 2013, which is a continuation-in-part (CIP) of U.S. patent application Ser. No. 14/014,555, filed Aug. 30, 2013, and issued as U.S. Pat. No. 9,365,387 on Jun. 14, 2016, which claims priority to U.S. Provisional Patent Application No. 61/695,953, filed Aug. 31, 2012, the benefit of priority of each of which is claimed hereby, and each of which is incorporated herein by reference in its entirety.

BACKGROUND

The present embodiments relate generally to articles of footwear and including removable motorized adjustment systems.

Articles of footwear generally include two primary elements: an upper and a sole structure. The upper is often formed from a plurality of material elements (e.g., textiles, polymer sheet layers, foam layers, leather, synthetic leather) that are stitched or adhesively bonded together to form a void on the interior of the footwear for comfortably and securely receiving a foot. More particularly, the upper forms a structure that extends over instep and toe areas of the foot, along medial and lateral sides of the foot, and around a heel area of the foot. The upper may also incorporate a lacing system to adjust the fit of the footwear, as well as permitting entry and removal of the foot from the void within the upper. Likewise, some articles of apparel may include various kinds of closure systems for adjusting the fit of the apparel.

SUMMARY

In one aspect, the present disclosure is directed to an article of footwear including a motorized tensioning system. The tensioning system may include a tensile member and a motorized tightening device configured to apply tension in the tensile member to adjust the size of an internal void defined by the article of footwear. The tensioning system may further include a power source configured to supply power to the motorized tightening device. The tensile member, the motorized tightening device, and the power source may be configured to be removably attached to the article of footwear.

In another aspect, the present disclosure is directed to a method of changing a lacing system of an article of footwear. The method may include providing an article of footwear including a motorized tensioning system attached to the article of footwear, the motorized tensioning system including a tensile member laced through eye stays in a lacing region of the article of footwear, a motorized tightening device configured to apply tension in the tensile member to adjust the size of an internal void defined by the article of footwear, and a power source configured to supply power to the motorized tightening device. The method may further include removing the tensile member, the motorized tightening device, and the power source from the article of footwear. In addition, the method may include lacing a manual lace into the article of footwear.

In another aspect, the present disclosure is directed to a motorized footwear lacing system. The lacing system may include an article of footwear and a manual lace. In addition, the lacing system may include a motorized tensioning system, including a tensile member and a motorized tightening device configured to apply tension in the tensile member to adjust the size of an internal void defined by the article of footwear. Also the lacing system may include a container configured to contain the article of footwear, the manual lace, the tensile member, and the motorized tightening device. Further, the tensile member and the motorized tightening device may be configured to be removably attached to the article of footwear and replaced with the manual lace.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 12 is a schematic isometric view of an embodiment of a shaft and a rotational control assembly;

FIG. 15 is a schematic isometric view of an embodiment of a spool;

DETAILED DESCRIPTION

Figure 1:
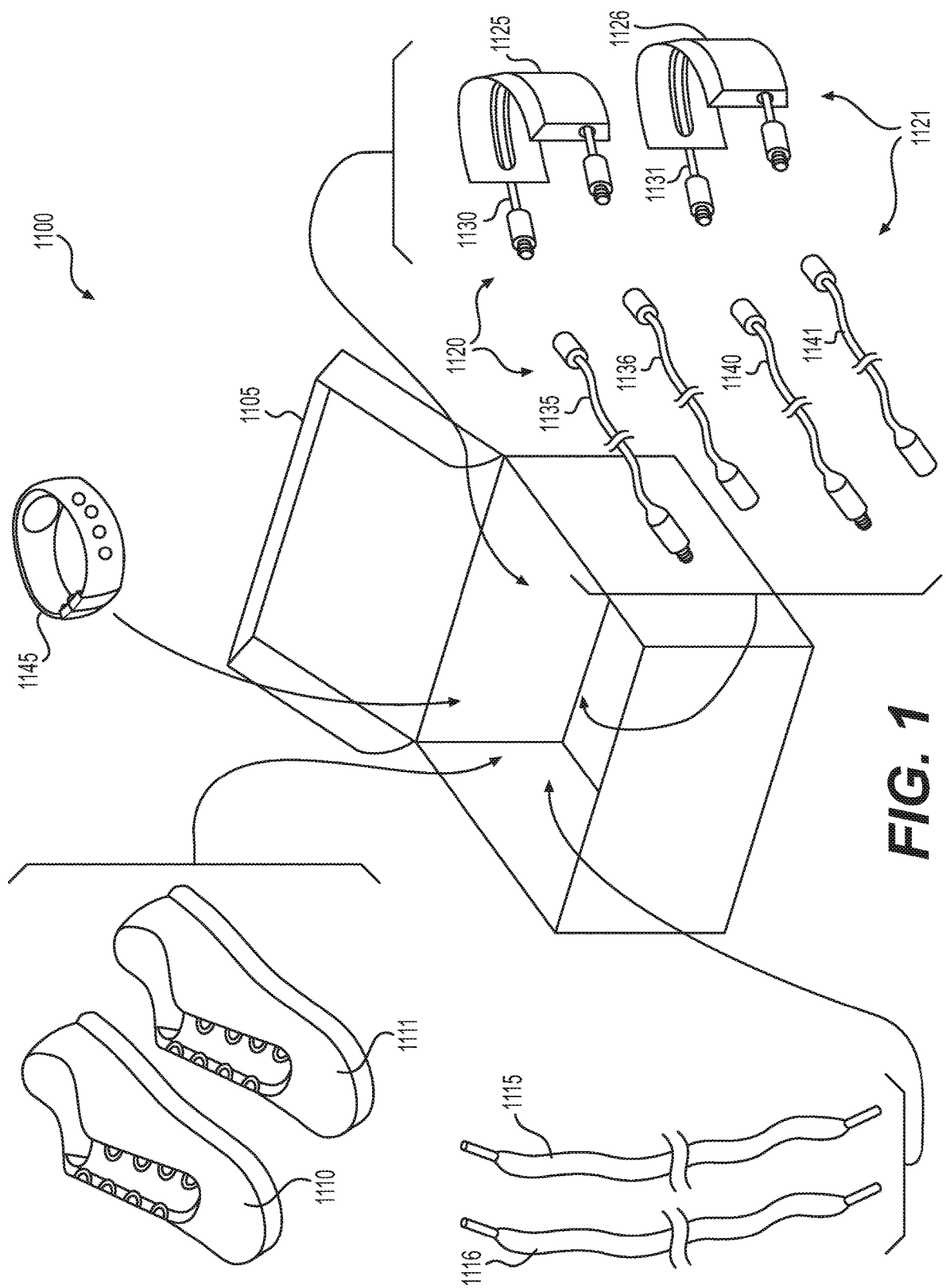
FIG. 1 is a schematic illustration of an embodiment of a kit of parts including an article of footwear, a motorized tensioning system, and a remote device for controlling the tensioning system.

The following discussion and accompanying figures disclose articles of footwear and motorized lacing systems for the footwear. Concepts associated with the footwear disclosed herein may be applied to a variety of athletic footwear types, including running shoes, basketball shoes, soccer shoes, baseball shoes, football shoes, and golf shoes, for example. Accordingly, the concepts disclosed herein apply to a wide variety of footwear types.

To assist and clarify the subsequent description of various embodiments, various terms are defined herein. Unless otherwise indicated, the following definitions apply throughout this specification (including the claims). For consistency and convenience, directional adjectives are employed throughout this detailed description corresponding to the illustrated embodiments.

The term "longitudinal," as used throughout this detailed description and in the claims, refers to a direction extending a length of a component. For example, a longitudinal direction of an article of footwear extends from a forefoot region to a heel region of the article of footwear. The term "forward" is used to refer to the general direction in which the toes of a foot point, and the term "rearward" is used to refer to the opposite direction, i.e., the direction in which the heel of the foot is facing.

The term "lateral direction," as used throughout this detailed description and in the claims, refers to a side-to-side direction extending a width of a component. In other words, the lateral direction may extend between a medial side and a lateral side of an article of footwear, with the lateral side of the article of footwear being the surface that faces away from the other foot, and the medial side being the surface that faces toward the other foot.

The term "side," as used in this specification and in the claims, refers to any portion of a component facing generally in a lateral, medial, forward, or rearward direction, as opposed to an upward or downward direction.

The term "vertical," as used throughout this detailed description and in the claims, refers to a direction generally perpendicular to both the lateral and longitudinal directions. For example, in cases where a sole is planted flat on a ground surface, the vertical direction may extend from the ground surface upward. It will be understood that each of these directional adjectives may be applied to individual components of a sole. The term "upward" refers to the vertical direction heading away from a ground surface, while the term "downward" refers to the vertical direction heading towards the ground surface. Similarly, the terms "top," "upper," and other similar terms refer to the portion of an object substantially furthest from the ground in a vertical direction, and the terms "bottom," "lower," and other similar terms refer to the portion of an object substantially closest to the ground in a vertical direction.

The "interior" of a shoe refers to space that is occupied by a wearer's foot when the shoe is worn. The "inner side" of a panel or other shoe element refers to the face of that panel or element that is (or will be) oriented toward the shoe interior in a completed shoe. The "outer side" or "exterior" of an element refers to the face of that element that is (or will be) oriented away from the shoe interior in the completed shoe. In some cases, the inner side of an element may have other elements between that inner side and the interior in the completed shoe. Similarly, an outer side of an element may have other elements between that outer side and the space external to the completed shoe. Further, the terms "inward" and "inwardly" shall refer to the direction toward the interior of the shoe, and the terms "outward" and "outwardly" shall refer to the direction toward the exterior of the shoe.

For purposes of this disclosure, the foregoing directional terms, when used in reference to an article of footwear, shall refer to the article of footwear when sitting in an upright position, with the sole facing groundward, that is, as it would be positioned when worn by a wearer standing on a substantially level surface.

In addition, for purposes of this disclosure, the term "fixedly attached" shall refer to two components joined in a manner such that the components may not be readily separated (for example, without destroying one or both of the components). Exemplary modalities of fixed attachment may include joining with permanent adhesive, rivets, stitches, nails, staples, welding or other thermal bonding, or other joining techniques. In addition, two components may be "fixedly attached" by virtue of being integrally formed, for example, in a molding process.

For purposes of this disclosure, the term "removably attached" shall refer to the joining of two components in a manner such that the two components are secured together, but may be readily detached from one another. Examples of removable attachment mechanisms may include hook and loop fasteners, friction fit connections, interference fit connections, threaded connectors, cam-locking connectors, and other such readily detachable connectors.

A motorized footwear lacing system may include an article of footwear, a manual lace, and a motorized tensioning system. The motorized tensioning system may include a tensile member and a motorized tightening device that may be removable and interchangeable with the manual lace. In some embodiments, the lacing system may be provided as a kit of parts, including a container in which a pair of footwear, a pair of motorized tensioning systems, and a pair of manual laces may be provided. In some embodiments, the motorized tightening device may be removably attached to the heel portion of the article of footwear. The tensile member may include a cord or other lace-like member that attaches to the motorized tightening device. In some embodiments, the cord may be laced through eye stays in a lacing region of the article of footwear. Accordingly, when the motorized tightening device and the tensile member are removed from the footwear, the manual lace may be laced into the same eye stays in which the tensile member is used.

The motorized tensioning system enables relatively rapid tightening of the footwear. In addition, in some embodiments the tightening system may provide incremental tightening. Such incremental tightening may enable the user to achieve a predictable tightness for each wearing. In some embodiments, sensors may be included to monitor tightness. In such embodiments, the user may also achieve a predictable tightness.

In some cases, using a motorized tensioning device may remove dexterity issues that may occur with other tensioning technologies (pulling straps, Velcro, and other such manual closure systems). Such a design could improve the use of footwear for physically impaired or injured individuals who may otherwise have a hard time putting on and adjusting their footwear. Using the designs proposed here, footwear could be tightened via a push button or remote interface.

In some embodiments, the tensioning system may be remotely controlled, for example by a bracelet or hand-held device. In such embodiments, adjustments may be made without the wearer having to stop the activity in which they are participating. For example, a distance runner may adjust the tightness of their footwear without interrupting their workout or competitive event.

In addition, the tensioning system may also be configured to make automatic adjustments. For example, using tightness sensors, the system may be configured to maintain tightness during wear by adjusting tightness according to changes in the fit. For example, as feet swell during wear, the tensioning system may release tension on the tensile member, in order to maintain the initially selected tightness.

In addition, the tensioning system may be configured to adjust the tightness during use to improve performance. For example, as a wearer places loads on the footwear during an athletic activity, the system may tighten or loosen the tensile members to achieve desired performance characteristics. For example, as a runner proceeds around a curve, the tensioning system may tighten the footwear in order to provide additional stability and maintain the foot in a centralized position within the footwear. As another example, when a runner is running downhill, the tightening system may loosen the footwear to limit additional forces exerted on the foot as the foot tends to slide toward the front of the footwear during the downhill run. Numerous other automated adjustments may be utilized for performance. Such automated adjustments may vary for each activity. In addition, the type and amount of such adjustments may be preselected by the user. For instance, using the examples above, the user may select whether to tighten or loosen the footwear while proceeding around a curve. In addition, the user may select whether to utilize an automated adjustment at all during certain conditions. For example, the user may choose to implement the adjustment while proceeding around curves, but may opt not to utilize an adjustment when running downhill.

Providing the motorized tensioning system as removable from the article of footwear may enable the footwear to be used conventionally. In addition, removability of the tensioning system may enable components of the tensioning system to be repaired or replaced independent of the footwear. In addition, removability of the tensioning system enables the footwear to be repaired or replaced independent of the tensioning system.

FIG. 1 illustrates a motorized footwear lacing system 1100. As shown in FIG. 1, system 1100 may be a kit of parts. The kit of parts may include a container 1105 configured to store components of the motorized footwear lacing system 1100. System 1100 may include a first article of footwear 1100. System 1100 may also include a first manual lace 1116 configured to be laced into footwear 1110 in a conventional manner. Lace 1116 may be utilized to modify the dimensions of interior void 1165, thereby securing the foot of a wearer within interior void 1165 and facilitating entry and removal of the foot from interior void 1165.

System 1100 may include a first motorized tensioning system 1120, which may include a first tensile member and a first motorized tightening device 1125 configured to apply tension in the tensile member to adjust the size of an internal void defined by footwear 1110. The term "tensile member," as used throughout this detailed description and in the claims, refers to any component that has a generally elongated shape and high tensile strength. In some cases, a tensile member could also have a generally low elasticity. Examples of different tensile members include, but are not limited to: laces, cables, straps and cords. In some cases, tensile members may be used to fasten and/or tighten an article footwear. In other cases, tensile members may be used to apply tension at a predetermined location for purposes of actuating some components or system.

In some embodiments, the tensile member may be provided in sections. For example, the tensile member may include a first tensile member portion 1130, which may be associated with tightening device 1125. For example, first tensile member portion 1130 may extend through motorized tightening device 1125, as shown in FIG. 1. In addition, the tensile member may include a second tensile member portion 1135, which may be releasably attached to first tensile member portion 1130. Also, the tensile member may include a third tensile member portion 1136, which may be attachable to first tensile member portion 1130. Second tensile member portion 1135 and third tensile member portion 1136 may be laced into footwear 1110, and thus, replace manual lace 1116. Once second tensile member portion 1135 and third tensile member portion 1136 are laced into footwear 1110, second tensile member portion 1135 may be releasably fastened to third tensile member portion 1136.

Motorized tightening device 1125 and the tensile member may be removably attached to footwear 1110. In addition, manual lace 1116 may be interchangeable with the tensile member and motorized tightening device 1125.

In some embodiments, system 1100 may include a pair of footwear and thus may include a second article of footwear 1111. Further, since system 1100 may include a pair of footwear, the other components of system 1100 may also be provided in pairs. For example, system 1100 may include a second manual lace 1115. In addition, system 1100 may include a second motorized tensioning system 1121. Second motorized tensioning system 1121 may include a second motorized tensioning device 1126. Second motorized tensioning system 1121 may also include a second tensile member, including a fourth tensile member portion 1131, a fifth tensile member portion 1140, and a sixth tensile member portion 1141. For purposes of description, only one of each pair of components will be discussed in detail below.

As further shown in FIG. 1, motorized footwear lacing system 1100 may include a remote device 1145 configured to control motorized tightening device 1125. In some embodiments, remote device 1145 may be provided in the form of a bracelet, as shown in FIG. 1. For example, remote device 1145 may be implemented as a function of a watch. In some embodiments, remote device 1145 may be a handheld device. For example, remote device 1145 may be implemented as a function of a mobile telephone or other mobile device.

Container 1105 may be configured to contain the pair of footwear, the pair of manual laces, and the pair of motorized tensioning systems, including the tensile members and the pair of motorized tightening devices. As shown in FIG. 1, in some embodiments, container 1105 may be a box, such as a shoe box.

Figure 2:
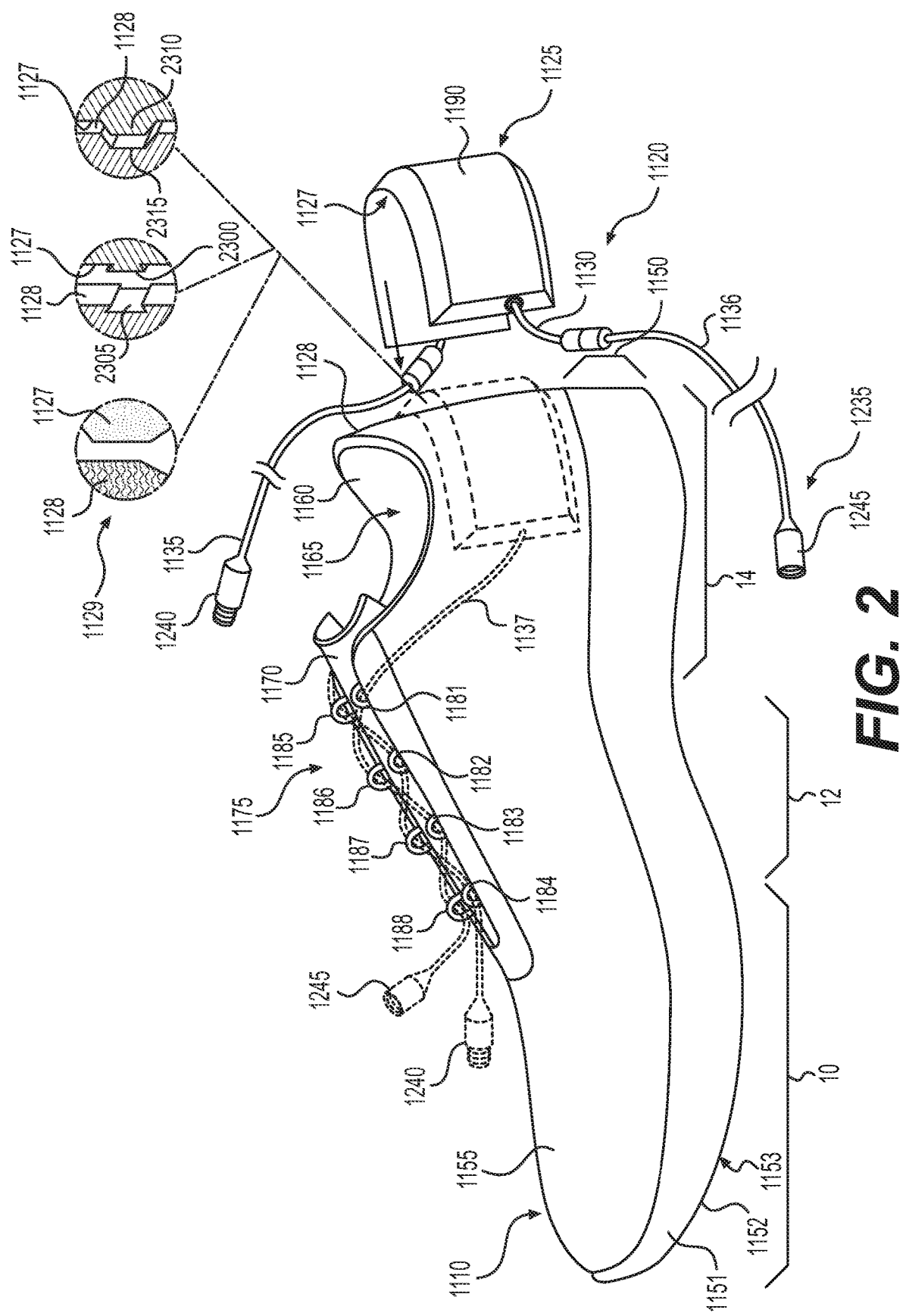
FIG. 2 is an exploded view of an embodiment of an article of footwear and an attachable motorized tensioning system.

FIG. 2 illustrates the association between tensioning system 1120 and footwear 1110. For reference purposes, footwear 1110 may be divided into three general regions: a forefoot region 10, a midfoot region 12, and a heel region 14. Forefoot region 10 generally includes portions of footwear 1110 corresponding with the toes and the joints connecting the metatarsals with the phalanges. Midfoot region 12 generally includes portions of footwear 1110 corresponding with an arch area of the foot. Heel region 14 generally corresponds with rear portions of the foot, including the calcaneus bone. Forefoot region 10, midfoot region 12, and heel region 14 are not intended to demarcate precise areas of footwear 1110. Rather, forefoot region 10, midfoot region 12, and heel region 14 are intended to represent general relative areas of footwear 1110 to aid in the following discussion. Since various features of footwear 1110 extend beyond one region of footwear 1110, the terms forefoot region 10, midfoot region 12, and heel region 14 apply not only to footwear 1110, but also to the various features of footwear 1110.

Footwear 1110 may include a sole structure 1150 and an upper 1155 secured to sole structure 1150. As shown in FIG. 2, upper 1155 may include one or more material elements (for example, meshes, textiles, foam, leather, and synthetic leather), which may be joined to define an interior void 1165 configured to receive a foot of a wearer. The material elements may be selected and arranged to selectively impart properties such as light weight, durability, air-permeability, wear-resistance, flexibility, and comfort. Upper 1155 may define a throat opening 1160 through which a foot of a wearer may be received into void 1165.

Sole structure 1150 may be fixedly attached to upper 1155 (for example, with adhesive, stitching, welding, or other suitable techniques) and may have a configuration that extends between upper 1155 and the ground. Sole structure 1150 may include provisions for attenuating ground reaction forces (that is, cushioning and stabilizing the foot during vertical and horizontal loading). In addition, sole structure 1150 may be configured to provide traction, impart stability, and control or limit various foot motions, such as pronation, supination, or other motions.

The configuration of sole structure 1150 may vary significantly according to one or more types of ground surfaces on which sole structure 1155 may be used. For example, the disclosed concepts may be applicable to footwear configured for use on any of a variety of surfaces, including indoor surfaces or outdoor surfaces. The configuration of sole structure 11150 may vary based on the properties and conditions of the surfaces on which footwear 1110 is anticipated to be used. For example, sole structure 1150 may vary depending on whether the surface is harder or softer. In addition, sole structure 1150 may be tailored for use in wet or dry conditions.

In some embodiments, sole structure 1150 may be configured for a particularly specialized surface or condition. For example, in some embodiments, footwear 1110 is illustrated in the accompanying figures as a running shoe and, accordingly, the illustrated sole structure 1150 is configured for providing cushioning, stability, and traction on hard, smooth surfaces, such as pavement. The proposed footwear upper construction may be applicable to any kind of footwear, however, such as basketball, soccer, football, and other athletic activities. Accordingly, in some embodiments, sole structure 1150 may be configured to provide traction and stability on hard indoor surfaces (such as hardwood), soft, natural turf surfaces, or on hard, artificial turf surfaces. In some embodiments, sole structure 1150 may be configured for use on a multiple different surfaces.

In some embodiments, sole structure 1150 may include multiple components, which may individually or collectively provide footwear 1110 with a number of attributes, such as support, rigidity, flexibility, stability, cushioning, comfort, reduced weight, or other attributes. In some embodiments, sole structure 1150 may include an insole/sockliner (See FIG. 46), a midsole 1151, and a ground-contacting outer sole member 1152, which may have an exposed, ground-contacting lower surface 1153, as shown in FIG. 2. In some cases, however, one or more of these components may be omitted.

The insole may be disposed in void 1165 defined by upper 1155. The insole may extend through each of forefoot region 10, midfoot region 12, and heel region 14, and between a lateral side and medial side of footwear 1110. The insole may be formed of a deformable (for example, compressible) material, such as polyurethane foams, or other polymer foam materials. Accordingly, the insole may, by virtue of its compressibility, provide cushioning, and may also conform to the foot in order to provide comfort, support, and stability.

Midsole 1151 may be fixedly attached to a lower area of upper 1155 (for example, through stitching, adhesive bonding, thermal bonding (such as welding), or other techniques), or may be integral with upper 1155. Midsole 1151 may extend through each of forefoot region 10, midfoot region 12, and heel region 14, and between a lateral side and medial side of footwear 100. In some embodiments, portions of midsole 1151 may be exposed around the periphery of footwear 1110, as shown in FIG. 2. In other embodiments, midsole 1151 may be completely covered by other elements, such as material layers from upper 1155. Midsole 1151 may be formed from any suitable material having the properties described above, according to the activity for which footwear 1110 is intended. In some embodiments, midsole 160 may include a foamed polymer material, such as polyurethane (PU), ethyl vinyl acetate (EVA), or any other suitable material that operates to attenuate ground reaction forces as sole structure 1150 contacts the ground during walking, running, or other ambulatory activities.

As shown in FIG. 2, footwear 1110 may include a tongue 2270, which may be provided in a lacing region 1175. In some embodiments, lacing region 1175 may be provided in an instep region of footwear 1110, as shown in FIG. 2. However, in other embodiments, the lacing region may be provided in other portions of the article of footwear. (See FIGS. 48 and 49.)

As shown in FIG. 2, footwear 1110 may include a plurality of eye stays in lacing region 1175 configured to receive a lace. For example, footwear 1110 may include a first eye stay 1181, a second eye stay 1182, a third eye stay 1183, and a fourth eye stay 1184 on a first side of lacing region 1175. In addition, footwear 1110 may include a fifth eye stay 1185, a sixth eye stay 1186, a seventh eye stay 1187, and an eighth eye stay 1188 on a second side of lacing region 1175. The eye stays are illustrated schematically in FIG. 2, and may have any suitable configuration that will accept a conventional shoelace as well as the tensile member of tensioning system 1120.

FIG. 2 schematically illustrates the placement of motorized tensioning system 1120 when removably attached to footwear 1110. As illustrated by a dashed outline 1137, tensioning system 1120 may be removably attached to heel region 14 of footwear 1110. Motorized tightening device 1125 may be disposed in a housing 1190, which may have a shape that conforms with the heel counter of footwear 1110.

As shown in FIG. 2, housing 1190 may have a first surface 1127 configured to mate with a second surface 1128 on upper 1155 of footwear 1110. In some embodiments, first surface 1127 and second surface 1128 may be removably attached with a hook and loop fastener material 1129. In other embodiments, first surface 1127 and second surface 1128 may be removably attached with a tongue and groove configuration, including a tongue 2300 and groove 2305. Tongue 2300 and groove 2305 are shown oriented in a substantially horizontal position for purposes of illustration. As implemented, tongue 2300 and groove 2305 may be oriented vertically. In such a vertical orientation, housing 1190 may be slid vertically into position. In other embodiments, first surface 1127 and second surface 1128 may be removably attached with an interference fit or friction fit. For example, a first protruding portion 2310 may extend into a recess 2315 in an interference fit. The components of such a friction fit attachment may have any suitable orientation.

It will be noted that the components of these connections may be disposed on either first surface 1127 or second surface 1128. For example, the hook component of the hook and loop fastener 1129 may be located on either first surface 1127 or second surface 1128. The loop component of hook and loop fastener 1129 may be disposed on the opposing surface to the hook component. Similarly, tongue 2300 may be located on either first surface 1127 or second surface 1128 and groove 2305 may be located on the opposing surface from tongue 2300. Further, protruding portion 2310 may be located on either first surface 1127 or second surface 1128 and recess 2315 may be located on the opposing surface from protruding portion 2310. These disclosed removable connections are intended to be exemplary only. Alternative types of removable connections are also possible including, for example, threaded fasteners, cam-lock fasteners, spring clip type fasteners, and other removable connection mechanisms.

As shown in FIG. 2 by dashed line 1137, the tensile member may be laced through the eyelets in lacing region 1175, in the same or similar manner as a manual lace. For example, third tensile member portion 1135 may be threaded through fifth eyelet 185, second eyelet 182, seventh eyelet 1187, and fourth eyelet 1184. Similarly, fourth tensile member portion 1136 may be threaded through first eyelet 1181, sixth eyelet 1186, third eyelet 1183, and eighth eyelet 1188. Since third tensile member portion 1135 and fourth tensile member portion 1136 may be detachable from first tensile member portion 1130, third tensile member portion 1135 and fourth tensile member portion 1136 may be laced through the eyelets from either end. It will be noted that the mechanical connectors connecting the portions of the tensile member together are shown schematically and are shown enlarged for purposes of illustration. For example, a coupling 1235 at the distal ends of third tensile member portion 1135 an fourth tensile member portion 1136 may include a first connector portion 1240 and a second connector portion 1245. First connector portion 1240 and second female portion 1245 may be sized and configured to be laced through the eyelets in lacing region 1175.

A method of changing the lacing system of footwear 1110 may include removing the tensile member, motorized tightening device 1125, and a power source from the article of footwear and lacing a manual lace into footwear 1110. In some embodiments, lacing a manual lace into the article of footwear includes lacing the manual lace into the eye stays from which the tensile member of system 1120 was removed. The step of removing motorized tightening device 1125 from footwear 1110 may include detaching housing 1190 from upper 1155 of footwear 1110.

Figure 3:
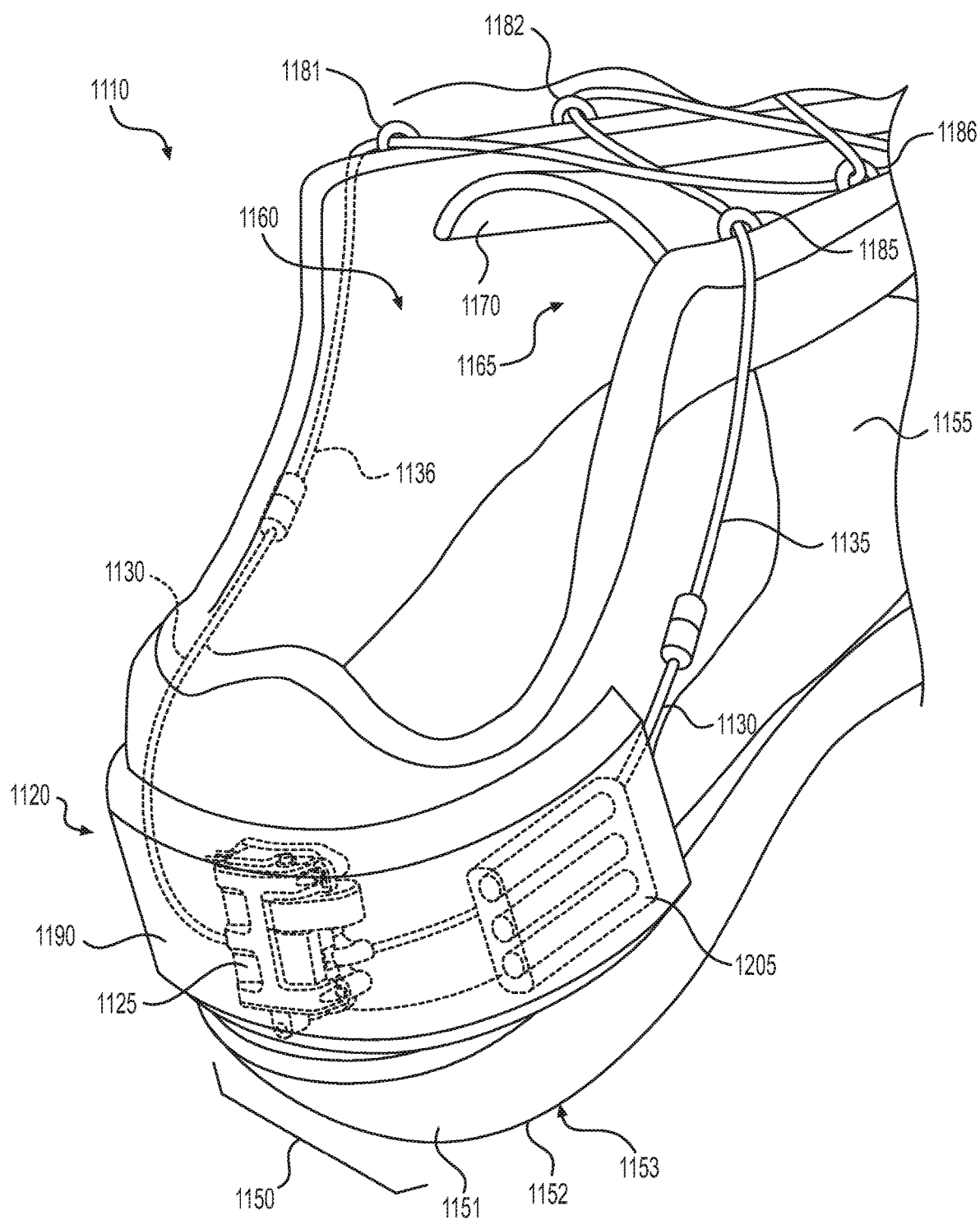
FIG. 3 is a perspective, assembled view of an embodiment of an article of footwear and an attachable motorized tensioning system.

FIG. 3 is a rear perspective view of article of footwear 1110 with tensioning system 1120 removably installed. As shown in FIG. 3, housing 1190 is removably attached to a heel portion of footwear 1110. In addition, third tensile member portion 1135 and fourth tensile member portion 1136 are laced into the eye stays, including first eye stay 1181, second eye stay 1182, fifth eye stay 1185, and sixth eye stay 1186. The remainder of the lacing region has been truncated in FIG. 3 for purposes of illustration.

As shown in FIG. 3, tensioning system 1120 may include motorized tightening device 1125 configured to apply tension in the tensile member to adjust the size of internal void 1165 defined by footwear 1110. Tightening device may be disposed within housing 1190.

As also shown in FIG. 3, system 1120 may include a power source 1205 configured to supply power to motorized tightening device 1125. Housing 1190 may be configured to house motorized tightening device 1125 and power source 1205, as well as first tensile member portion 1130.

In some embodiments, power source 1205 may include one or more batteries. Power source 1205 is only intended as a schematic representation of one or more types of battery technologies that could be used to power motorized tightening device 1125. One possibly battery technology that could be used is a lithium polymer battery. The battery (or batteries) could be rechargeable or replaceable units packaged as flat, cylindrical, or coin shaped. In addition, batteries could be single cell or cells in series or parallel.

Rechargeable batteries could be recharged in place or removed from an article for recharging. In some embodiments, charging circuitry could be built in and on board. In other embodiments, charging circuitry could be located in a remote charger. In another embodiment, inductive charging could be used for charging one or more batteries. For example, a charging antenna could be disposed in a sole structure of an article and the article could then be placed on a charging mat to recharge the batteries.

Additional provisions could be incorporated to maximize battery power and/or otherwise improve use. For example, it is also contemplated that batteries could be used in combination with super caps to handle peak current requirements. In other embodiments, energy harvesting techniques could be incorporated which utilize the weight of the runner and each step to generate power for charging a battery.

Figure 4:
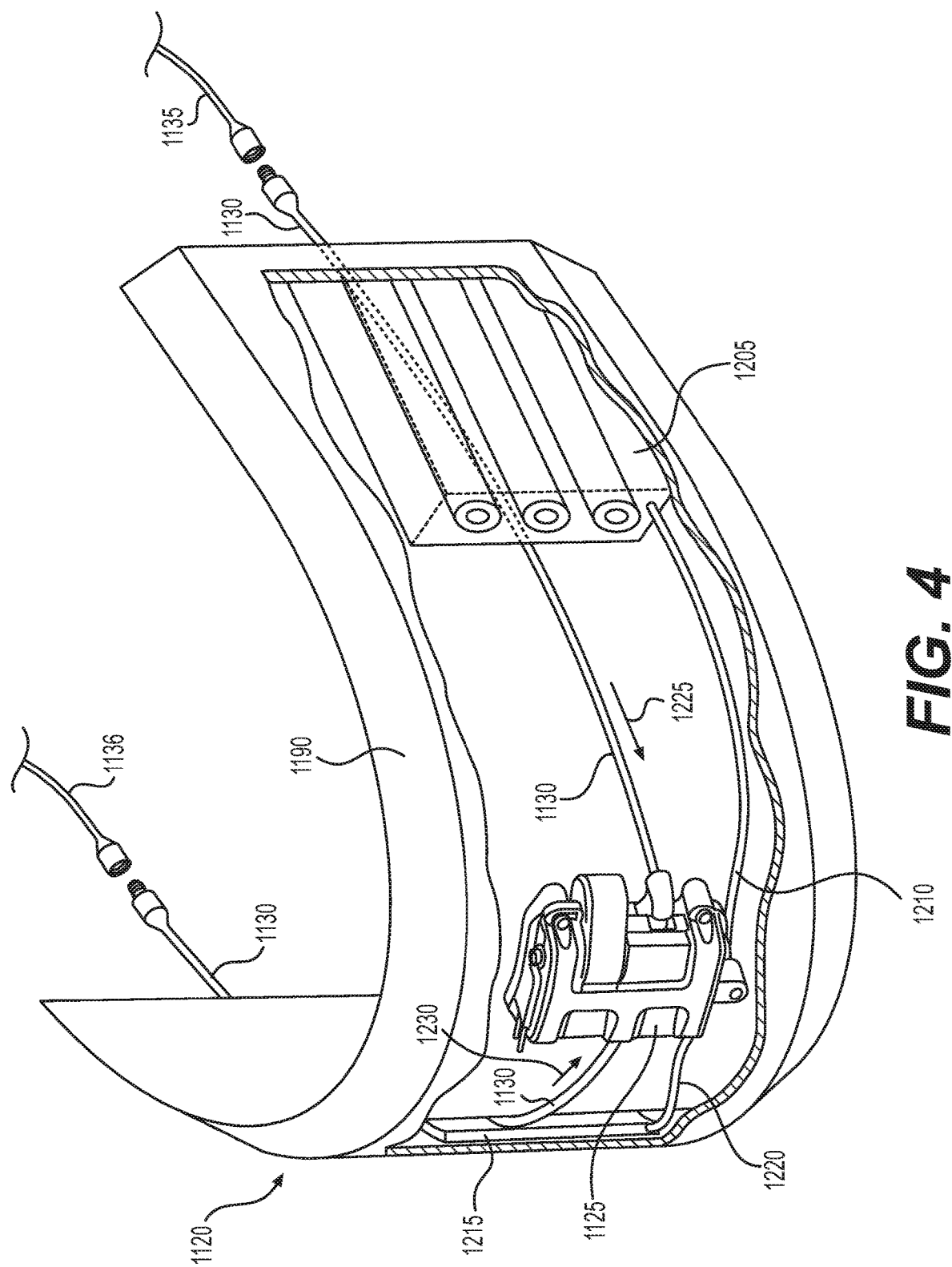
FIG. 4 is a partial cutaway view of the attachable motorized tensioning system.

FIG. 4 is a rear perspective view of motorized tensioning system 1120. FIG. 4 includes a cutaway view of housing 1190 exposing components of system 1120 located within housing 1190. For example, FIG. 4 shows motorized tightening device 1125. FIG. 4 shows an outer housing of tightening device 1125. The inner winding mechanisms of tightening device 1125 are discussed in greater detail below. As shown in FIG. 4, tightening device 1125 may be configured to apply tension to the tensile member by drawing first tensile member portion 1130 into tightening device 1125, as illustrated by a first arrow 1225 and a second arrow 1230. It will be noted that the routing of first tensile member portion 1130 is merely schematic, and more complicated arrangements for such routing are possible.

Also exposed in FIG. 4 is power source 1205, as well as a control unit 1215. Control unit 1215 may include various circuitry components. In addition, control unit 1215 may include a processor, configured to control motorized tightening device 1125. As shown in FIG. 4, tensioning system 1120 may include a first electrical cable 1210 extending between power source 1205 and motorized tightening device 1125. In addition, a second electrical cable 1220 may extend between control unit 1215 and tightening device 1125. First electrical cable 1210 and second electrical cable 1220 may be configured to deliver electrical power, as well as electronic communication signals, between power source 1205, tightening device 1125, and control unit 1215.

Control unit 1215 is only intended as a schematic representation of one or more control technologies that could be used with motor tightening device 1125. For example, there are various approaches to motor control that may be employed to allow speed and direction control. For some embodiments, a microcontroller unit may be used. The microcontroller may use internal interrupt generated timing pulses to create pulse-width modulation (PWM) output. This PWM output is fed to an H-bridge which allows high current PWM pulses to drive the motor both clockwise and counterclockwise with speed control. However, any other methods of motor control known in the art could also be used.

Figure 5:
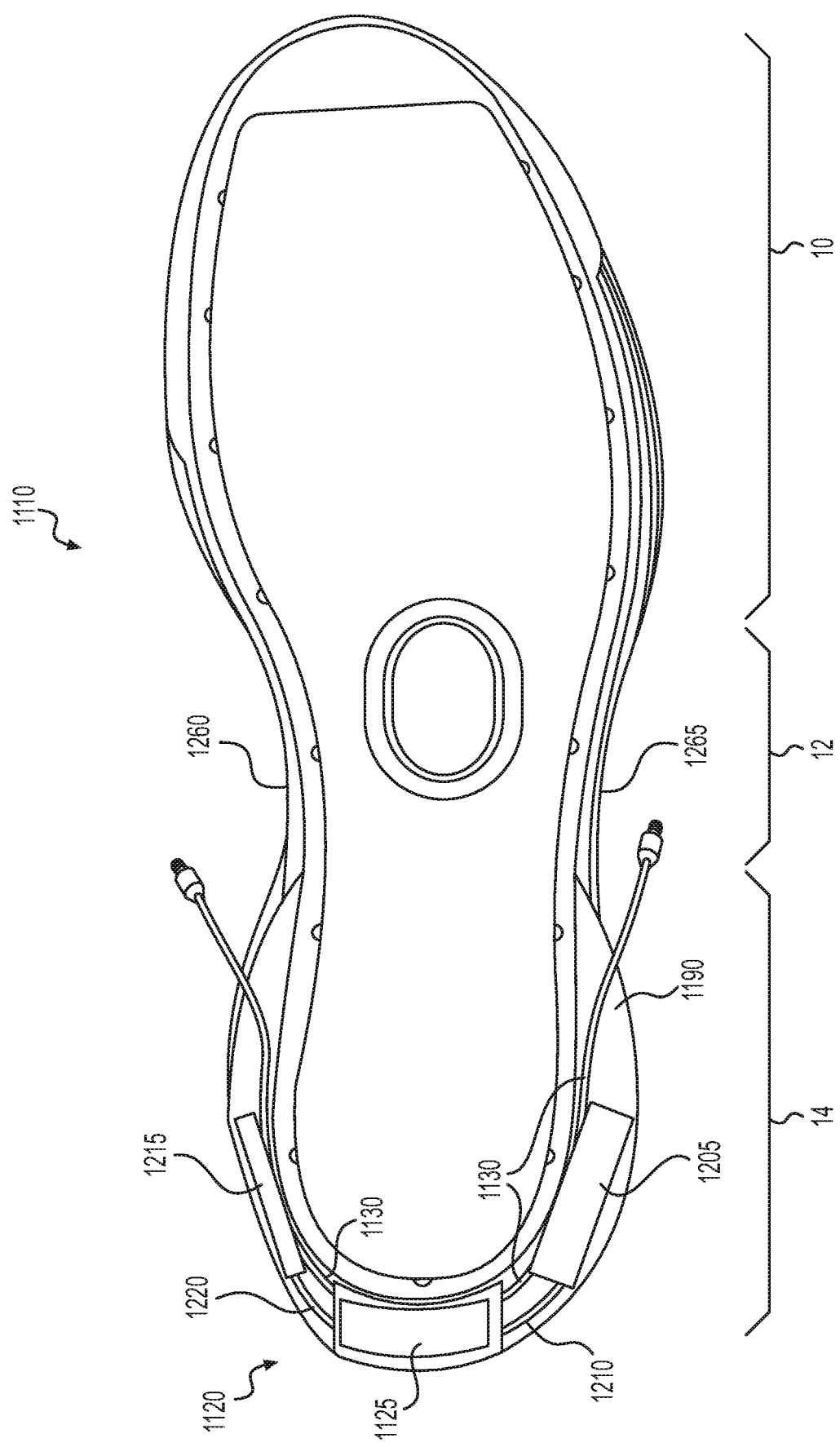
FIG. 5 is a top down schematic view of a portion of an article of footwear including a removable adjustment apparatus, in which the locations of a motorized tensioning device, a control unit, and a battery pack are indicated schematically.

FIG. 5 is a schematic top view of tensioning system 1120 installed on footwear 1110. As shown in FIG. 5, housing 1190 may be configured to be removably attached to a heel portion of footwear 1110. Further, tightening device 1125, power source 1205, and control unit 1215 may be housed within housing 1190, which may function to receive and protect these components. As shown in FIG. 5, in some embodiments, when housing 1190 is attached to the heel portion of footwear 1110, motorized tensioning device 1125 may be disposed in a rearmost portion of footwear 1110. This positioning may facilitate the application of tension to tensile members on both a medial side 1260 and a lateral side 1265 of footwear 1110.

In other embodiments, however, any of these components could be disposed in any other portions of an article, including the upper and/or sole structure. In some cases, some components could be disposed in one portion of an article and other components could be disposed in another, different, portion. In another embodiment motorized tensioning device 1125 could be disposed at the heel of an upper, while power source 1205 and/or control unit 1215 could be disposed with a sole structure of footwear 1110. For example, in one embodiment the power source and control unit may be disposed under midfoot region 12 of article 1110 with a cable connection (or a simple electrical contact connection) to motorized tensioning device 1125, which may be disposed in heel region 14. In still other embodiments, a power source and a control unit could be integrated into a motorized tensioning device. For example, in some embodiments, both a battery and a control unit could be disposed within an outer housing of motorized tensioning device 1125.

Further, in some embodiments, housing 1190 may be configured to wrap at least partially around medial side 1260 and lateral side 1265 of the heel portion of footwear 1110, as also shown in FIG. 5. In FIG. 5, control unit 1215 is shown on medial side 1260 in heel region 14 of footwear 1110. Power source 1205 is shown on lateral side 1265 in heel region 14 of footwear 1110. The positions of control unit 1215 and power source 1205 may be reversed in some embodiments. However, it may be advantageous to locate the thinner component on the medial side 1260 of footwear 1110. This may enable housing 1190 to have a lower profile on medial side 1260 than on lateral side 1265 (as shown in FIG. 5), which may minimize the amount of housing 1190 that extends medially and could interfere with the footwear on the other foot of the wearer.

Figure 6:
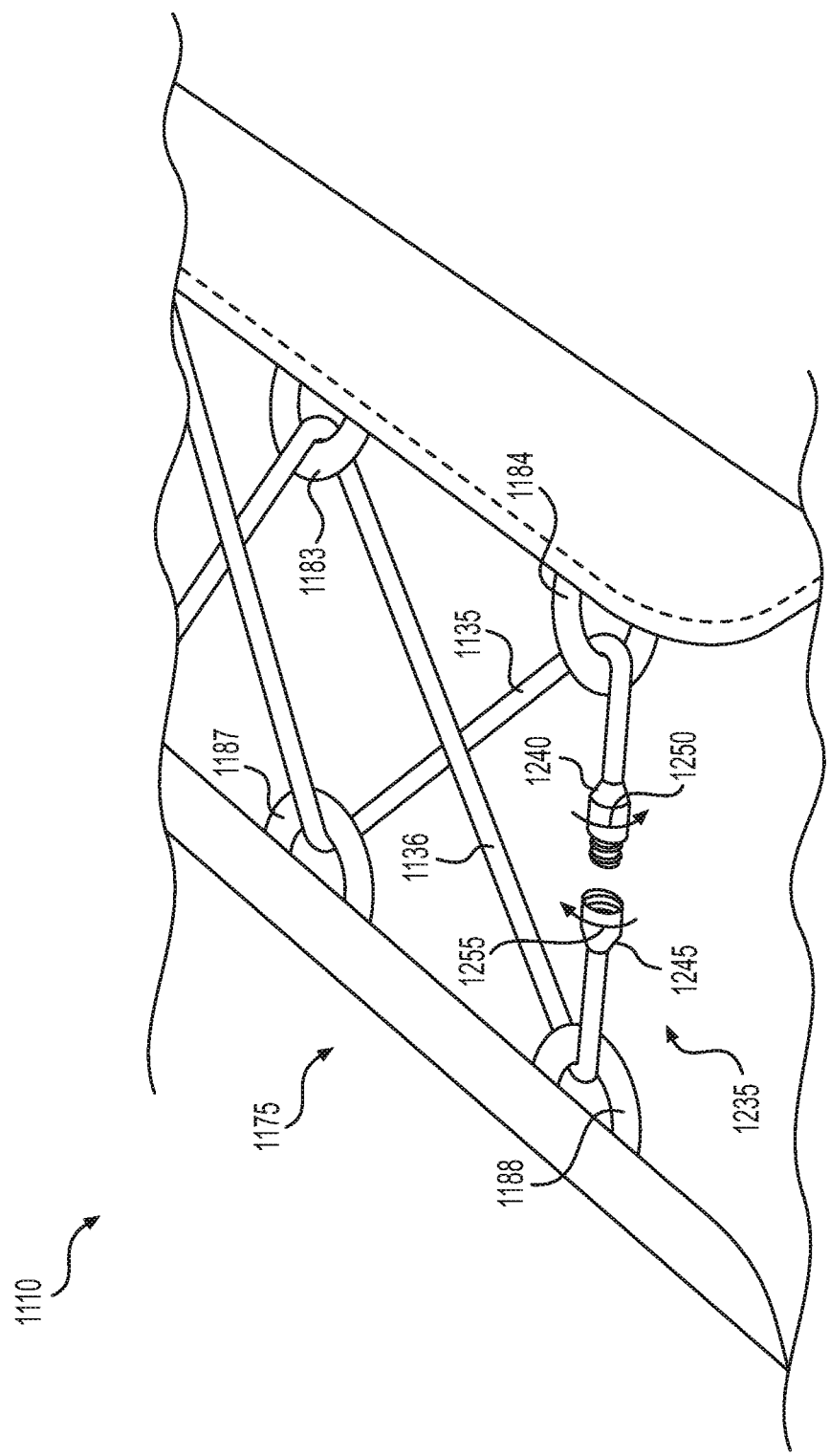
FIG. 6 is a schematic isometric view of an embodiment of a manual release mechanism for a tensioning system including a motorized tensioning device.

FIG. 6 is a partial view of lacing region 1175 of footwear 1110 with the tensile member of the tensioning system installed. As shown in FIG. 6, third tensile member portion 1135 is laced through seventh eyelet 1187 and fourth eyelet 1184. In addition, fourth tensile member portion 1136 is laced through third eyelet 1183 and eighth eyelet 1188. As shown in FIG. 6, the tensile member may include a manual release mechanism for manually decoupling third tensile member portion 1135 from a fourth tensile member portion 1136. For example, a coupling 1235 may include first connector portion 1240 at the distal end of third tensile member portion 1135, and second connector portion 1245 at the distal end of fourth tensile member portion 1135. As shown in FIG. 6, in some embodiments, the manual release mechanism, such as coupling 1235, may be located in an instep region of footwear 1110.

Coupling 1235 may be a readily decoupled manually, in order to enable removal of the tensile member from the article of footwear. Such manual decoupling may facilitate removal of the motorized tensioning system from footwear 1110. This manual release mechanism may also enable the tension in the tensile member to be released in the event of a malfunction or low battery power. Exemplary manual release mechanisms may include any suitable connector types. In some embodiments, threaded connections may be utilized. For example, first connector portion 1240 may include a male threaded portion and second connector portion 1245 may include a female threaded portion. In order to decouple coupling 1235, first connector portion 1240 and second connector portion 1245 may be twisted, for example in the directions of a first arrow 1250 and a second arrow 1255. While FIG. 6 illustrates a threaded coupling, in other embodiments the tensile member could utilized any other fastening provisions including a snap fit connector, a hook and receiver type connector, or any other kinds of manual fasteners known in the art.

Figure 7:
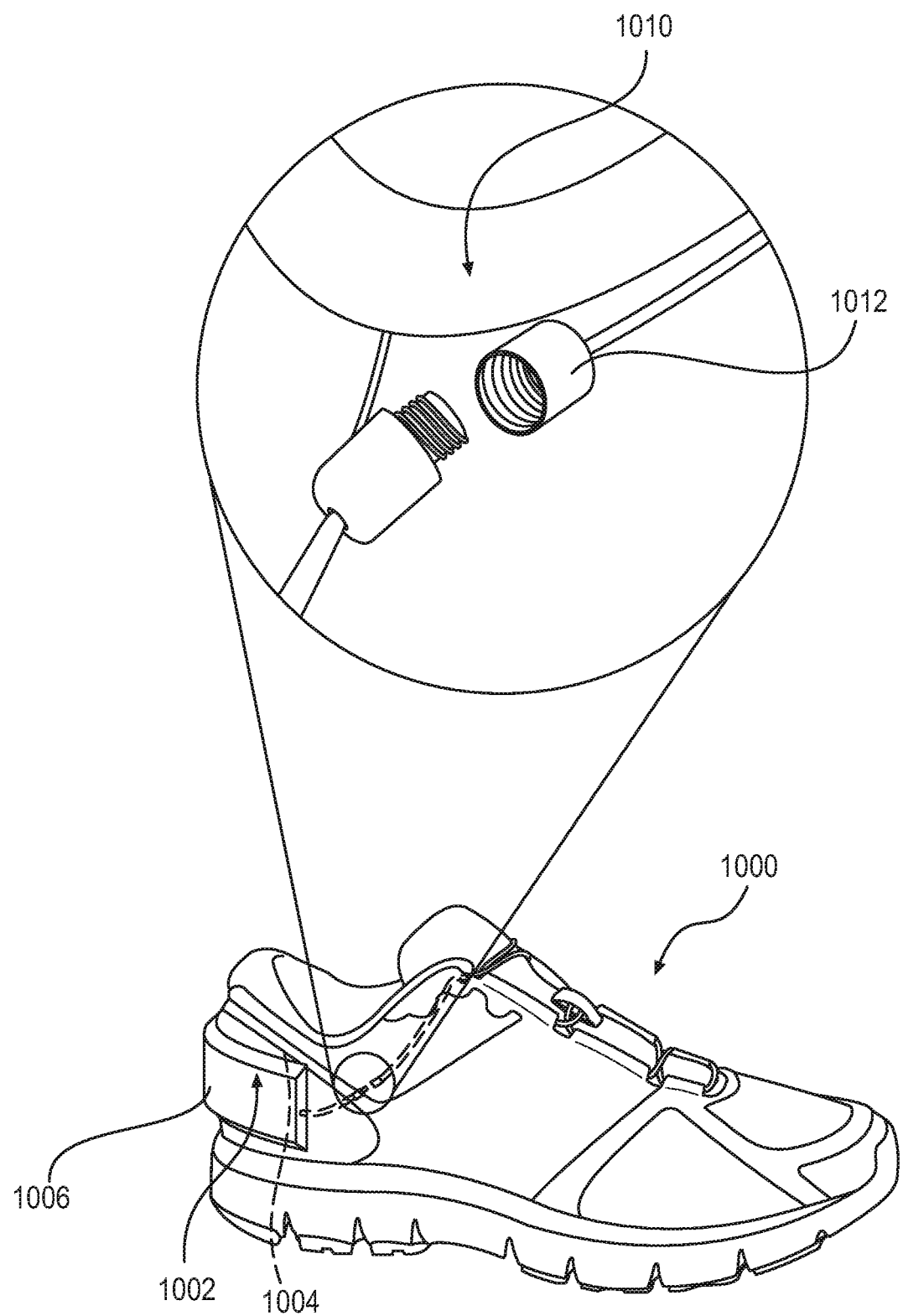
FIG. 7 is a schematic view of an embodiment of another manual release mechanism for a tensioning system including a motorized tensioning device.

FIG. 7 illustrates an embodiment of an exemplary manual release system for tensile members. Referring to FIG. 7, article 1000 may be similar to previous embodiments and can include a tensioning system 1002 with a lace 1004 and a motorized tensioning device 1006. In this embodiment, a portion of lace 1004 is equipped with a manual release mechanism 1010. In the embodiment shown here, manual release mechanism 1010 includes corresponding fasteners 1012 that can be manually disconnected to relieve lace tension. In some cases, fasteners 1012 comprise a threaded coupling, as shown in FIG. 7. However, other embodiments could utilized any other fastening provisions including a snap fit connector, a hook and receiver type connector, or any other kinds of fasteners known in the art.

Figure 8:
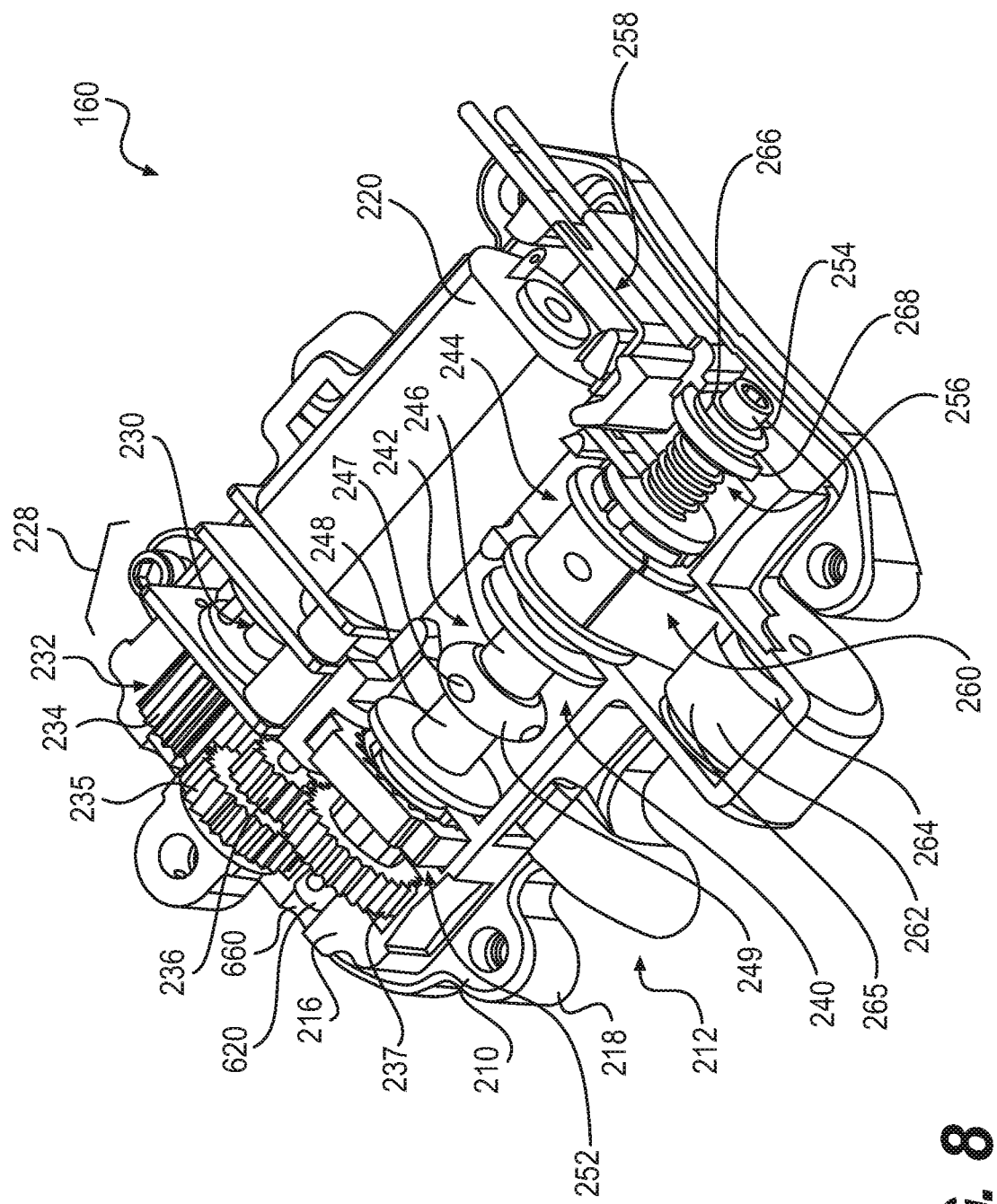
FIG. 8 is a schematic isometric view of an embodiment of a motorized tensioning device with an outer cover of the housing unit removed.
Figure 9:
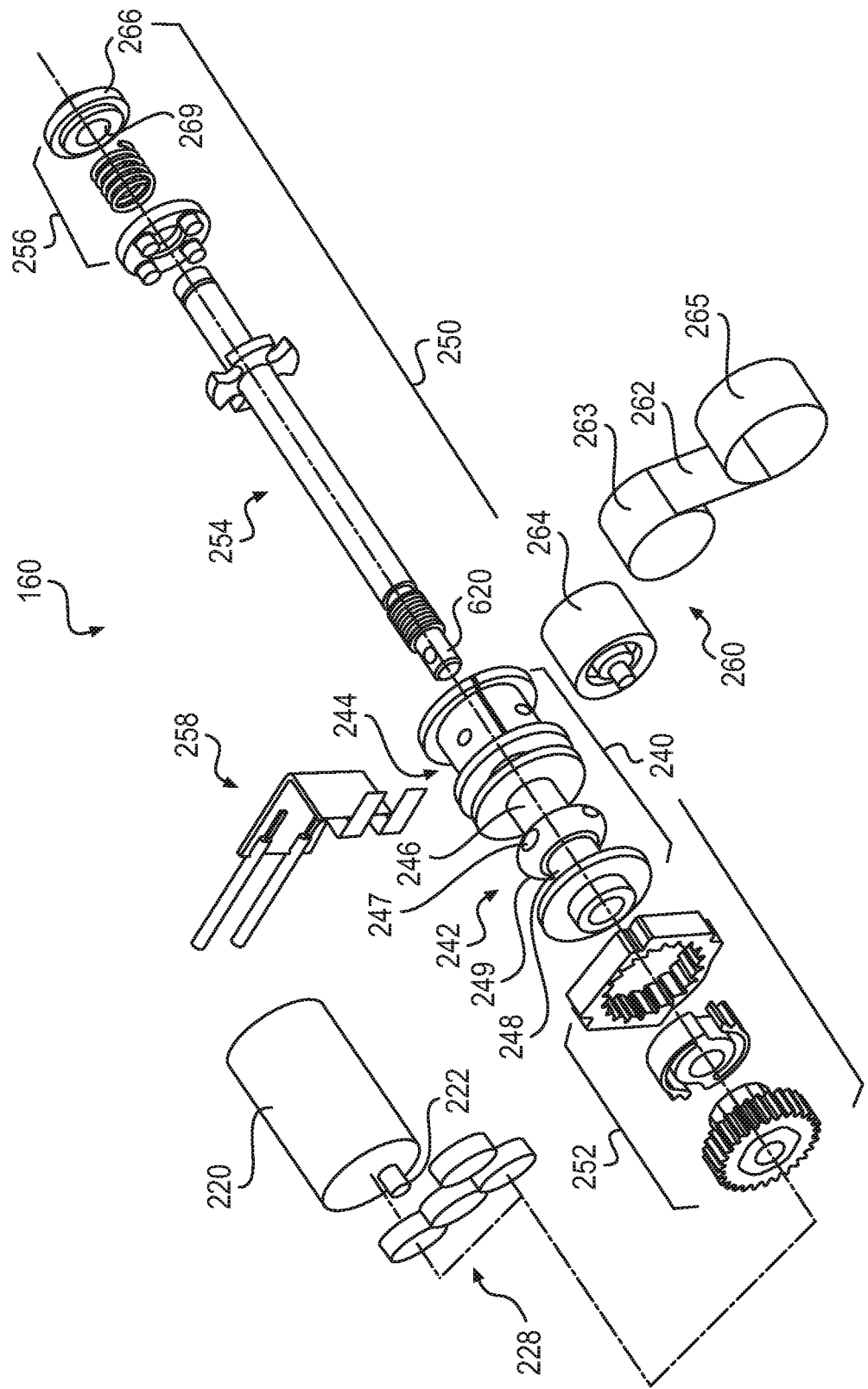
FIG. 9 is a schematic exploded isometric view of an embodiment of some components of a motorized tensioning device.

FIGS. 8 and 9 illustrate an isometric view and isometric exploded view, respectively, of an embodiment of the internal components of motorized tensioning device 160. Referring first to FIG. 8, the components are shown within a portion of housing unit 212. Housing unit 212 may further include an inner housing portion 216 and an outer housing portion 218. Outer housing portion 218 may include a base panel 210 as well as an outer cover 214, and generally provides a protective outer covering for components of motorized tensioning device 160. Inner housing portion 216 may be shaped to support components of motorized tensioning device 160. In some cases, portions of inner housing portion 216 function to limit the mobility of some components, as discussed in detail below.

Referring now to FIGS. 8 and 9, in some embodiments, motorized tensioning system 160 may comprise motor 220 (shown schematically in FIG. 9). In some embodiments, motor 220 may be an electric motor. However, in other embodiments, motor 220 could comprise any kind of non-electric motor known in the art. Examples of different motors that can be used include, but are not limited to: DC motors (such as permanent-magnet motors, brushed DC motors, brushless DC motors, switched reluctance motors, etc.), AC motors (such as motors with sliding rotors, synchronous electrical motors, asynchronous electrical motors, induction motors, etc.), universal motors, stepper motors, piezoelectric motors, as well as any other kinds of motors known in the art. Motor 220 may further include a motor crankshaft 222 that can be used to drive one or more components of motorized tensioning system 160. Provisions for powering motor 220, including various kinds of batteries, are discussed in detail below.

In some embodiments, motorized tensioning system 160 can include provisions for reducing the output speed of, and increasing the torque generated by, motor 220. In some embodiments, motorized tensioning system 160 can include one or more gear reduction assemblies and/or gear reduction systems. In some embodiments, motorized tensioning system 160 may include a single gear reduction assembly. In other embodiments, motorized tensioning system 160 may include two or more gear reduction assemblies. In one embodiment, motorized tensioning system 160 includes first gear reduction assembly 230 and second gear reduction assembly 232, which may be collectively referred to as gear reduction system 228. First gear reduction assembly 230 may be an in-line spur gear reduction assembly that is generally aligned with motor 220 and/or crankshaft 222. In contrast, second gear reduction assembly 232 may provide additional gear reduction that extends in a generally perpendicular direction to the orientation of crankshaft 222. With respect to housing unit 212, first gear reduction assembly 230 may extend in a longitudinal direction of housing unit 212 while second gear reduction assembly 232 may extend in a lateral (or horizontal) direction of housing unit 212. By using a combination of in-line gears and horizontally spaced gears, relative to the orientation of crankshaft 222, motor 220 can be arranged in parallel with a spool and corresponding spool shaft (as discussed in further detail below). This arrangement may reduce the longitudinal space required to fit all the components of motorized tensioning device 160 within housing unit 212.

Each gear reduction assembly can comprise one or more gears. In the exemplary embodiment, first gear reduction assembly 230 comprises one or more in-line spur gears. Moreover, first gear reduction assembly 230 may be driven by crankshaft 222 and itself drives a first gear 234 of second gear reduction assembly 232.

In one embodiment, second gear reduction assembly 232 may be configured with 4 stages of spur gears, including a first gear 234, a second gear 235, a third gear 236 and a fourth gear 237. In this embodiment, fourth gear 237 acts as a clamping gear for turning additional components of motorized tensioning device 160, as described in further detail below. The current embodiment of second gear reduction assembly 232 includes four gears. However, other embodiments could use any other number of gears. Likewise, the number of gears comprising first gear reduction assembly 230 may vary in different embodiments. Additionally, in different embodiments, the type of gears used in first gear reduction assembly 230 and/or second gear assembly 232 could vary. In some cases, spur gears may be used. Other examples of gears that may be used include, but are not limited to: helical gears, external gears, internal gears, bevel gears, crown gears, worm gears, non-circular gears, rack and pinion gears, epicyclic gears, planetary gears, harmonic drive gears, cage gears, magnetic gears as well as any other kinds of gears and/or any combinations of various kinds of gears. The number, type and arrangement of gears for gear reduction system 228 may be selected to achieve the desired tradeoff between size, torque and speed of the motorized tensioning system 160.

In some embodiments, motorized tensioning system 160 can include provisions for winding and unwinding portions of a lace. In some embodiments, motorized tensioning system 160 can include spool 240. In some cases, spool 240 may further comprise a first receiving portion 242 and a second receiving portion 244 for receiving a lace and a portion of a spring, respectively. Moreover, in some cases, first receiving portion 242 may comprise a first lace winding region 246 and a second lace winding region 248, which in some cases can be used to separately wind two ends of a lace. Since torque output goes down as the lace builds up in diameter, using separate winding regions for each lace end may help decrease the diameter of wound lace on spool 240 and thereby minimize torque output reduction. In some cases, first lace winding region 246 and second lace winding region 248 may be separated by a dividing portion 249, which may include a lace receiving channel 247 for permanently retaining a portion of the lace on spool 240. In other cases, however, first receiving portion 242 may comprise a single lace winding region.

Motorized lacing system 160 may include provisions for transferring torque between a final drive gear of second gear reduction assembly 232 and spool 240. In some embodiments, motorized lacing system 160 may include provisions for transferring torque from second gear reduction assembly 232 (or more generally from gear reduction system 228) to spool 240 in a manner that allows for incremental tightening, incremental loosening and full loosening of a lace. In one embodiment, motorized lacing system 160 may be configured with a torque transmitting system 250 that facilitates the transmission of torque from fourth gear 237 of second gear reduction assembly 232 to spool 240.

Torque transmitting system 250 may further comprise various assemblies and components. In some embodiments, torque transmitting system 250 may include a ratcheting assembly 252, a shaft 254 and a rotation control assembly 256. As discussed in further detail below, the components of torque transmitting system 250 operate to transmit torque from fourth gear 237 of second gear reduction assembly 232 to spool 240. More specifically, these components operate in a manner that allows for incremental tightening (spool winding), incremental loosening (spool unwinding) as well as full tension release (during which time substantially no torque is transferred from fourth gear 237 to spool 240).

In some embodiments, motorized tensioning device 160 may further include a secondary winding assembly 260. In some embodiments, secondary winding assembly 260 may be configured to apply torque to spool 240 independently of any torque applied by motor 220. In some cases, for example, secondary winding assembly 260 comprises a spring member 262 and a rotatable spring bearing 264. Spring member 262 may extends between second receiving portion 244 of spool 240 and spring bearing 264. In particular, a first end portion 263 of spring member 262 may be associated with spool 240 while a second end portion 265 of spring member 262 may be associated with spring bearing 264. In operation, spring member 262 may be configured to apply a biasing torque that may tend to rotate spool 240 in the lace winding direction in the absence of other forces or torques (for example when there is slack in the lace). Spring member 262 could be a wind-up spring, a constant force spring, a constant torque spring, a clock spring as well as any other kind of spring.

Some embodiments can also include a fixed bearing 266, which may be associated with an end of shaft 254. In some embodiments, fixed bearing 266 may be received within a recess 268 of inner housing portion 216. In some embodiments, an end of shaft 254 may be disposed within opening 269 of fixed bearing 266, and may be configured so that shaft 254 can slide through opening 269 to provide some axial movement for shaft 254.

In some embodiments, motorized tensioning device 160 may include provisions for adjusting the operation of motor 220 according to one or more feedback signals. In some embodiments, for example, motorized tensioning device 160 may include a limit switch assembly 258. Generally, limit switch assembly 258 may detect current across portions of rotation control assembly 256 and vary the operation of motor 220 according to the detected current. Further details on the operation of limit switch assembly 258 are discussed in detail below.

For purposes of reference, the following detailed description uses the terms "first rotational direction" and "second rotational direction" in describing the rotational directions of one or more components about an axis. For purposes of convenience, the first rotational direction and the second rotational direction refer to rotational directions about a longitudinal axis 284 (see FIG. 12) of shaft 254 and are generally opposite rotational directions. The first rotational direction may refer to the clockwise rotation of a component about longitudinal axis 284, when viewing the component from the vantage point of first end portion 620 of shall 254. First end portion 620 of shaft 254 may be the end portion associated with fourth gear 237. The second rotational direction may be then be characterized by the counterclockwise rotation of a component about longitudinal axis 284, when viewing the component from the same vantage point.

A brief overview of the operation of motorized tensioning device 160 is described here. A detailed description of the operation is given below. In the incremental tighten mode motor 220 may begin operating in order to rotate crankshaft 222. Crankshaft 222 may turn an input gear of first gear reduction assembly 230, such that the output gear of first gear reduction assembly 230 drives first gear 234 of second gear reduction assembly 232. The intermediate second gear 235 and third gear 236 both rotate, which drives fourth gear 237 in the first rotational direction. As fourth gear 237 rotates, fourth gear 237 may engage and drive torque transmitting system 250 such that spool 240 may eventually begin to rotate in the first rotational direction. This causes lace 152 to wind onto first receiving portion 242 of spool 240.

In the incremental loosen mode, motor 220 may operate to rotate crankshaft 222. In the loosening mode, motor 220 and crankshaft 222 turn in an opposite direction of the direction associated with tightening. The gear reduction system 228 is then driven such that fourth gear 237 of second gear reduction assembly 32 rotates in the second rotational direction. In contrast to the incremental tighten mode, in the incremental loosen mode fourth gear 237 does not directly drive portions of torque transmitting system 250 and spool 240. Instead, the motion of fourth gear 237 in the second rotational direction causes torque transmitting system 250 to momentarily release spool 240, allowing spool 240 to unwind by a predetermined amount after which torque transmitting system 250 reengages spool 240 and prevents further unwinding. This sequence of releasing and catching spool 240 occurs over and over as long as fourth gear 237 rotates in the second rotational direction. Further details of the method by which this incremental loosening is achieved is described in detail below.

Finally, in the open or fully loosen mode, torque transmitting system 250 operates so that substantially no torque is transmitted to spool 240 from any components of torque transmitting system 250. During this mode, spool 240 may rotate more easily in the unwinding direction about shaft 254 (for example, as a wearer manually loosens lace 152 to take off article 100). As slack forms along the lace, secondary winding assembly 260 may apply a small amount of torque to second receiving portion 244 of spool 240, which acts to wind up slack in lace 152.

FIGS. 10-14 illustrate various schematic views of the components comprising torque transmitting system 250. For purposes of clarity, these components are shown in isolation from other parts of motorized tightening device 160. Additionally, some components are not shown or may be shown in phantom in some views to reveal interior components.

Figure 10:
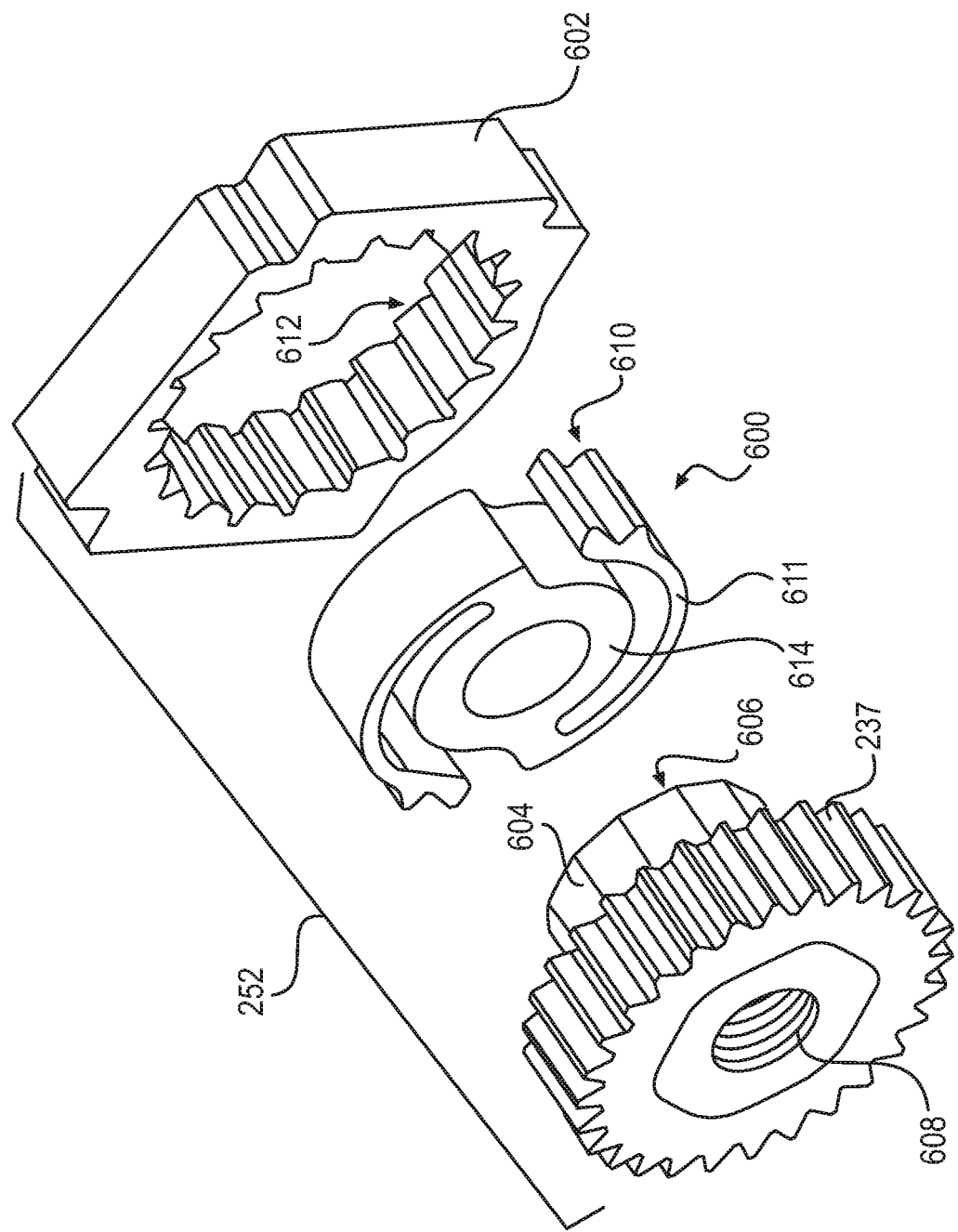
FIG. 10 is a schematic exploded isometric view of an embodiment of a ratcheting assembly.
Figure 11:
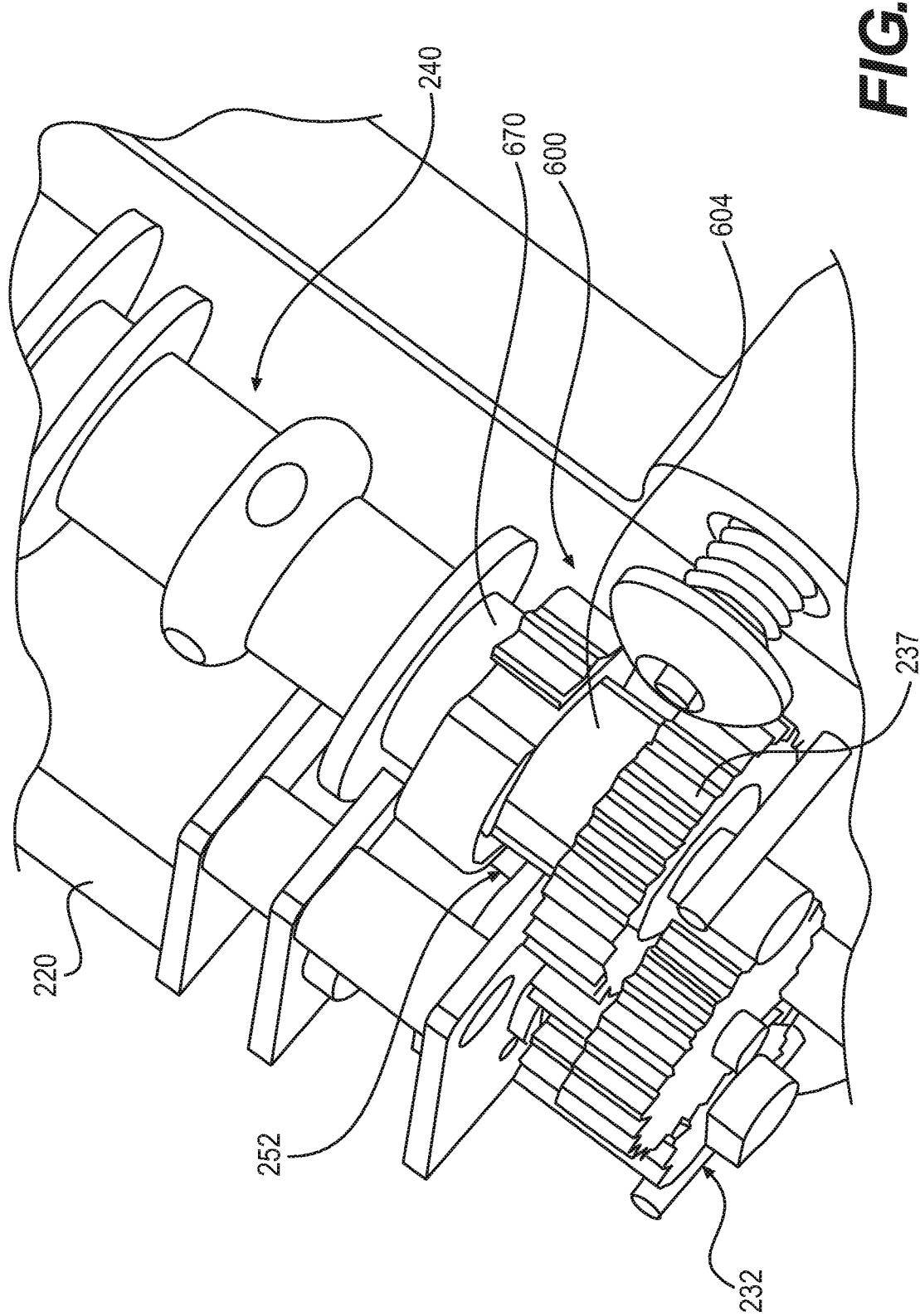
FIG. 11 is a schematic isometric view of a portion of a motorized tensioning system showing a ratcheting assembly clamped to a spool.

Referring first to FIGS. 10 and 11, ratcheting assembly 252 may comprise several components including fourth gear 237, pawl member 600 and ratchet housing 602 (ratchet housing 602 is not shown in FIG. 11 to better show the relative positions of fourth gear 237, pawl member 600 and spool 240). Fourth gear 237 may include an extended boss portion 604. In some embodiments, the extended boss portion 604 further includes a frictional face 606 that contacts pawl member 600. Fourth gear 237 may also include an internally threaded cavity 608 that may engage threading on shaft 254. For purposes of convenience, fourth gear 237 is characterized as part of both ratcheting assembly 252 and second gear reduction assembly 232 as fourth gear 237 acts as an element that confronts and directly drives pawl member 600 and also as a final driving gear of second gear reduction assembly 232. In particular, it is to be understood that characterizing fourth gear 237 as part of one assembly does not preclude it from being associated with a different assembly.

In some embodiments, pawl member 600 is configured to interface with ratchet housing 602. In particular, teeth 610, which extend from pawlarms 611, may engage with corresponding teeth 612 on ratchet housing 602. In some cases the geometry of pawl arms 611 and teeth 610 provide an arrangement where pawl member 600 can rotate within ratchet housing 602 in a first rotational direction, but pawl member 600 is prevented from rotating within ratchet housing 602 in a second rotational direction that is opposite of the first rotational direction.

In some embodiments, pawl member 600 includes a boss engaging surface 614 that confronts and can engage frictional face 606 of fourth gear 237. When frictional face 606 of fourth gear 237 is brought into contact with boss engaging surface 614 of pawl member 600, fourth gear 237 may drive pawl member 600. Moreover, the one-way ratchet design of ratcheting assembly 252 ensures that fourth gear 237 may only drive pawl member 600 in a first rotational direction.

Pawl member 600 may include a spool engaging surface 616 (see also FIG. 16) which confronts a first end 670 of spool 240. When spool engaging surface 616 is pressed against spool 240 with enough frictional force, pawl member 600 may be used to drive spool 240 in the first rotational direction. Thus, in the configuration shown in FIG. 11, with fourth gear 237, pawl member 600 and spool 240 all clamped together under sufficient frictional force, fourth gear 237 may act to drive pawl member 600 and thus spool 240.

Ratcheting assembly 252 is only intended to be exemplary of a one-way torque transmitting mechanism that may be used to transmit torque to a spool. Other embodiments are not limited to ratchet-like mechanisms and could include other one-way mechanisms. Examples of other one-way mechanisms that could be used include, but are not limited to: roller bearings, sprag clutches, ratcheting wheel and pawl as well as other mechanisms.

Figure 14:
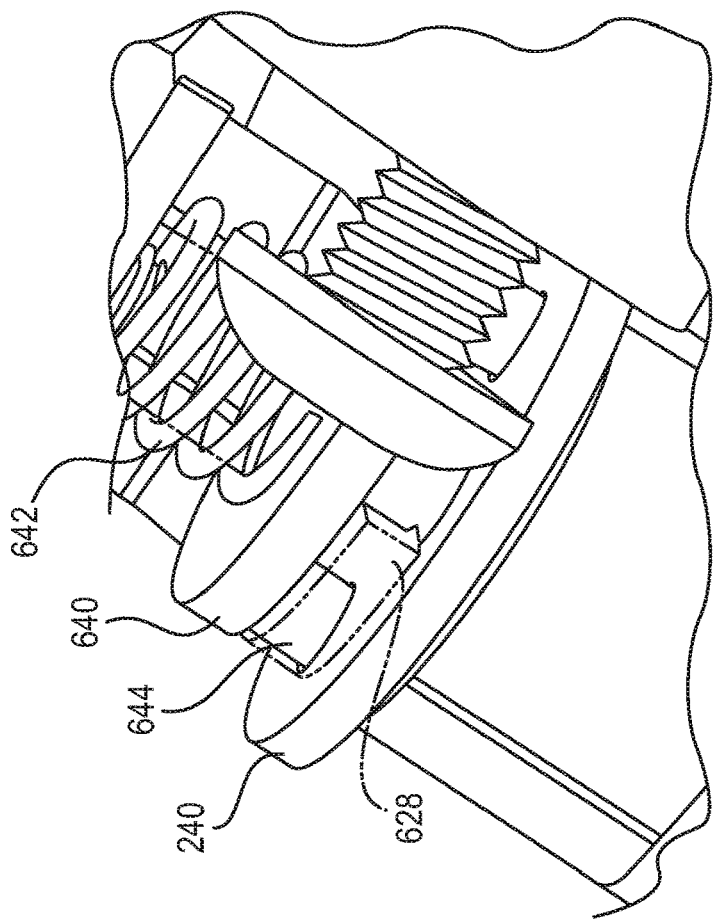
FIG. 14 is another schematic isometric view of a portion of the rotational control assembly of FIG. 13.
Figure 13:
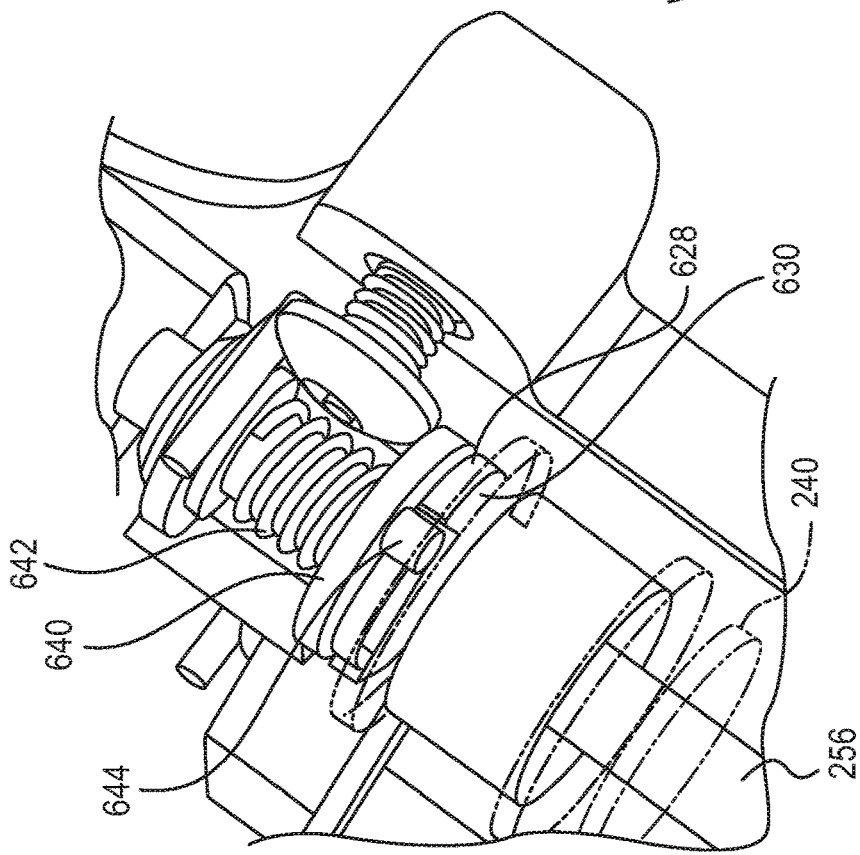
FIG. 13 is a schematic isometric view of a portion of a motorized tensioning system showing a rotational control assembly engaging a spool.

FIGS. 12-14 illustrate various views of additional components of torque transmitting system 250, including shaft 254 and rotation control assembly 256. In particular, FIG. 12 illustrates an isolated exploded view of shaft 254 and rotation control assembly 256, while FIGS. 13-14 illustrate assembled views of some portions of these components from various perspectives.

Shaft 254 may comprise a first end portion 620. In some embodiments, first end portion 620 may include threading 624. In some cases, threading 624 may engage internally threaded cavity 608 (see FIG. 10) of fourth gear 237, which may facilitate the relative axial movement of fourth gear 237 along shaft 254. Shaft 254 may also include a second end portion 622 that engages opening 269 of fixed bearing 266. In some embodiments, an intermediate portion 626 of shaft 254 may be disposed between first end portion 620 and second end portion 622.

Various portions of shaft 254 are configured to receive components of torque transmitting system 250 and spool 240. First end portion 620 and second end portion 622 may be associated with ratcheting assembly 252 and rotation control assembly 256, respectively. Intermediate portion 626 may be inserted within a central cavity 690 of spool 240 (see FIG. 15), such that spool 240 may rotate about intermediate portion 262.

In some embodiments, intermediate portion 626 of shaft 254 further includes a flange portion 628 that extends radially outwards from shaft 254. Flange portion 628 may include a spool engaging surface 630 that contacts spool 240. An opposing surface of flange portion 628 (not shown) may confront rotation control assembly 256. In some embodiments, flange portion 628 may include one or more slots 632.

In some embodiments, rotation control assembly 256 may include an engagement plate 640 and a compression spring 642. In some embodiments, engagement plate 640 further includes pins 644 that extend towards engagement plate 640 and spool 240. In some embodiments, pins 644 may be inserted through slots 632 of flange portion 628. Moreover, in some cases, pins 644 may be inserted into alignment holes 650 of spool 240 (see FIG. 15), which prevents shaft 254 and spool 240 from rotating independently of one another.

As seen in FIGS. 12-14, the components of rotation control assembly 256 are disposed along second end portion 622 of shaft 254. In some embodiments, compression spring 642 may be disposed between engagement plate 640 and fixed bearing 266 so that compression spring 642 may act to bias engagement plate 640 in an axial direction towards flange portion 628 and spool 240.

In other embodiments, alternate methods could be used for releasably coupling a shaft and spool. Examples include other kinds of physical interlocking features or including friction increasing features. As one example, axial compliant friction coupling could be achieved using a wave washer or Belleville washer.

FIG. 15 illustrates an isometric view of an embodiment spool 240 in isolation. As previously described, spool 240 includes provisions for receiving pins 644 of engagement plate 640. In this case, four alignment holes 650 are approximately evenly spaced about a second end face 673. Additionally, this particular view of spool 240 clearly illustrates a slot 675 that may be used for retaining an end of spring member 262.

Figure 16:
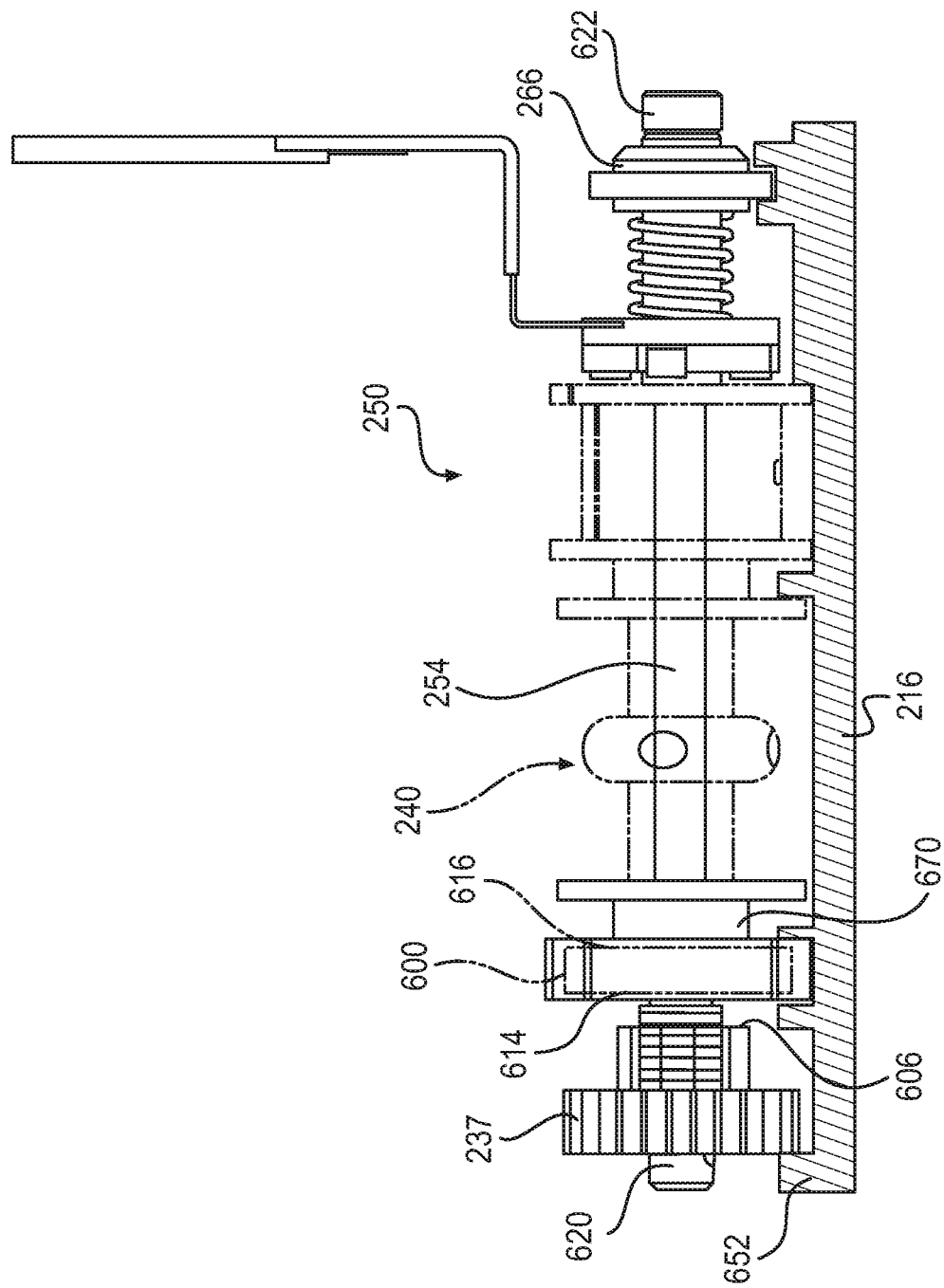
FIG. 16 is a side schematic view of an embodiment of a torque transmitting system.

Referring now to FIG. 16, the components of torque transmitting system 250 are shown in their assembled configuration along shaft 254. For purposes of reference, spool 240 is shown in phantom on shaft 254. In addition, a cross-sectional portion of inner housing portion 216 is shown for reference. As also seen in FIG. 8, when installed within inner housing portion 216, some components of torque transfer system 250 are constrained from any axial movement. For example, spool 240 and ratchet housing 602 are constrained from moving in an axial direction (or along a longitudinal direction of shaft 254). In contrast, fourth gear 237, which is threaded along first end portion 620 of shaft 254, can rotate about shaft 254 and translate axially (because of the threaded engagement) along shaft 254. In some embodiments, a wall portion 652 of inner housing portion 216 limits the axial motion of fourth gear 237 in a direction away from ratcheting assembly 252.

The arrangement shown here for torque transmitting system 250 also allows for both rotation and axial translation of shaft 254. In particular, second end portion 622 of shaft 254 may slide through fixed bearing 266, while first end portion 620 of shaft 254 is disposed in a channel 660 of inner housing portion 216 (see FIG. 8) that also allows for some axial motion of shaft 254. In some embodiments, the amount of axial translation may be limited by features including contact between flange portion 628 and spool 240, as well as possibly other features.

Figure 17:
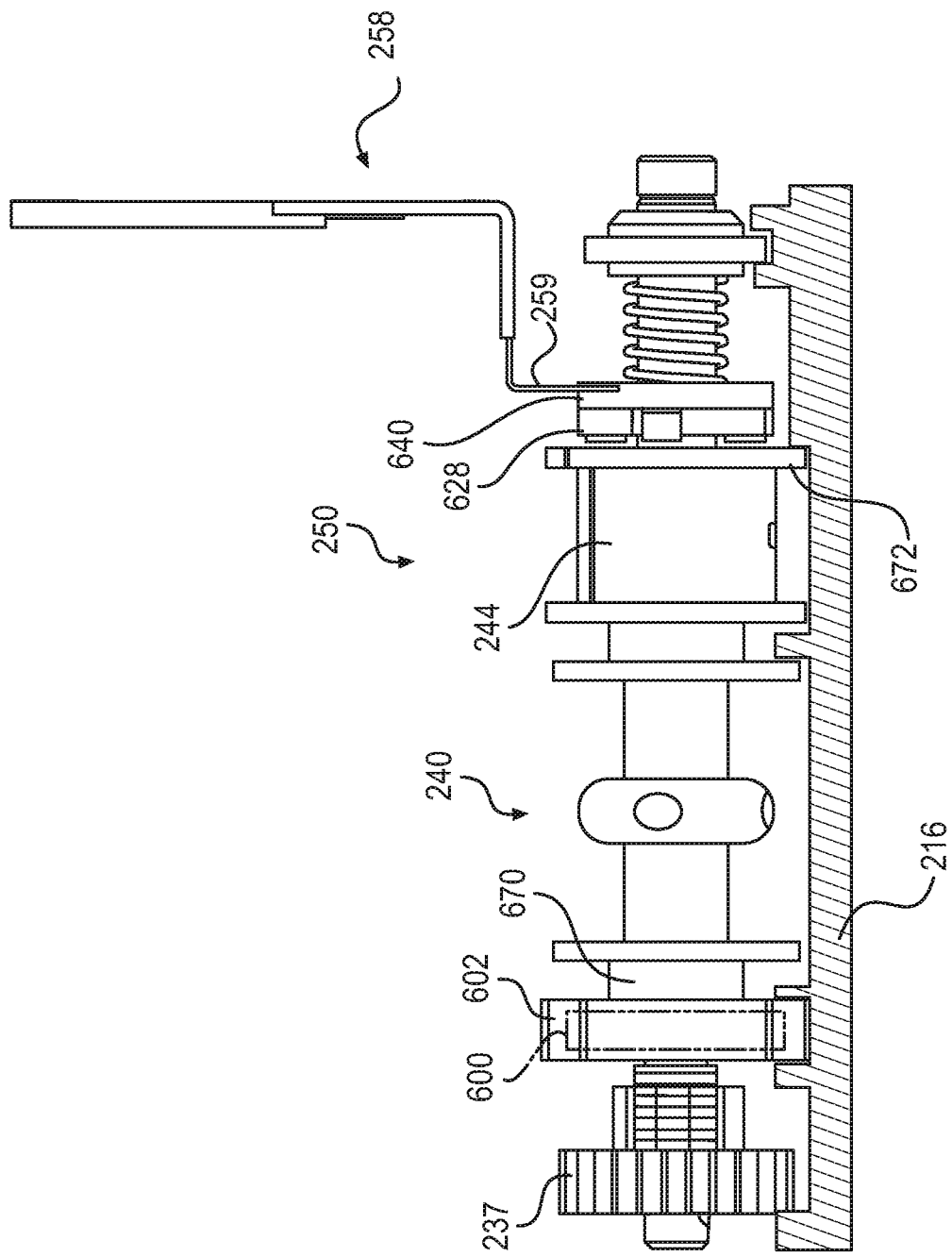
FIG. 17 is a side schematic view of an embodiment of a torque transmitting system in a fully loosened configuration.

FIGS. 17 through 26 illustrate schematic views of torque transmitting system 250 and spool 240 for purposes of illustrating the operation of torque transmitting system 250 during incremental tightening, incremental loosening and full loosening. Referring first to FIG. 17, torque transmitting system 250 is in a configuration where the lace is fully loosened. More specifically, this configuration is one in which no torque is transmitted to spool 240 from torque transmitting system 250. In this configuration, fourth gear 237 may be spaced away from pawl member 600 (disposed within ratchet housing 602) so that no torque is transmitted from fourth gear 237 to pawl member 600. Furthermore, without fourth gear 237 to provide any clamping pressure against pawl member 600 and spool 240, spool 240 may rotate without any substantial resistance at first end portion 670 from pawl member 600. Furthermore, in this configuration engagement plate 640 and flange portion 628 are spaced apart from second end 672 of spool 640, so that spool 240 also does not undergo any resistance to rotation at second end 672. Although features of inner housing portion 612 prevent any axial motion of spool 240, in this configuration spool 240 may rotate in a first rotational direction or a second rotational direction. As previously described, spool 240 may be biased to rotate in a first rotational direction (i.e., lace winding direction) by secondary winding assembly 260 (not shown), which applies a biasing torque to spool at second receiving portion 244. However, this biasing force may be just large enough to pull in slack and can be overcome relatively easily by a wearer pulling on the laces to unwind them from spool 240. Thus, spool 240 may rotate relatively freely in this configuration, though spool 240 will be biased to wind in slack in the absence of tension applied by the lace to spool 240.

As also shown in FIG. 17, in this fully loosened configuration the contacts 259 of limit switch assembly 258 are pressed against engagement plate 640. This contact with engagement plate 640 provides continuity for the switch, so that current may flow between contacts 259.

Figure 18:
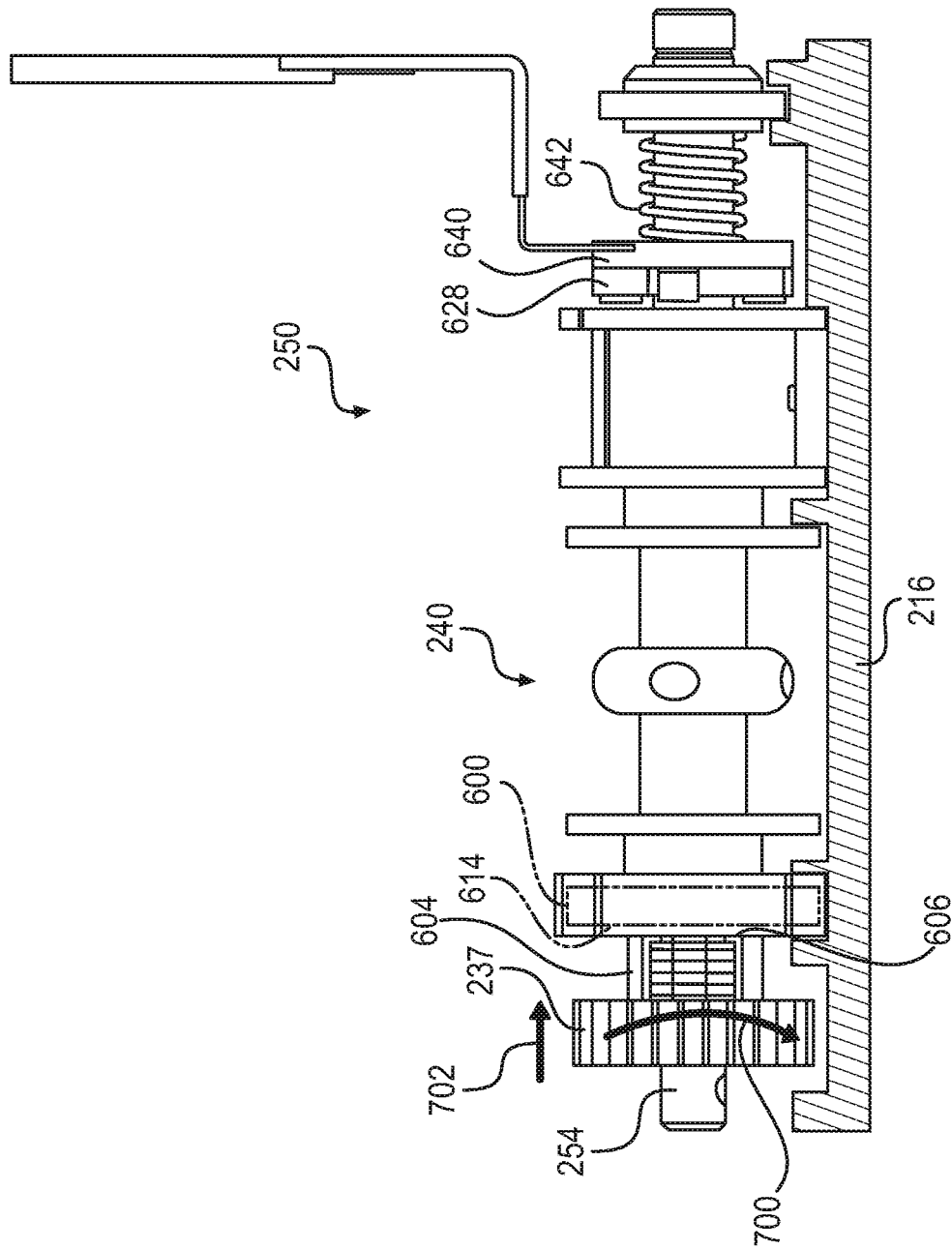
FIG. 18 is a side schematic view of an embodiment of a torque transmitting system in an incremental tightening configuration.

FIG. 18 shows the operation of torque transmitting system 250 as motor 220 (not shown) begins to rotate. Initially, motor 220 drives gear reduction system 228, so that fourth gear 237 is rotated in the first rotational direction (represented schematically by arrow 700). As fourth gear 237 rotates in the first rotational direction, fourth gear 237 translates axially (indicated by arrow 702) towards pawl member 600 because of the threaded interface between fourth gear 237 and shaft 254. Fourth gear 237 continues to rotate and translate axially until frictional face 606 of boss portion 604 contacts and presses against boss engaging surface 614 of pawl member 600. At this point, the preload from compression spring 642 may provide some drag on engagement plate 640 and flange portion 628 (which are coupled) to keep shaft 254 from rotating while fourth gear 237 translates axially along shaft 254. Without this drag, or another source of friction or drag, shaft 254 may be inclined to turn with fourth gear 237 so that fourth gear 237 would not translate axially.

Figure 19:
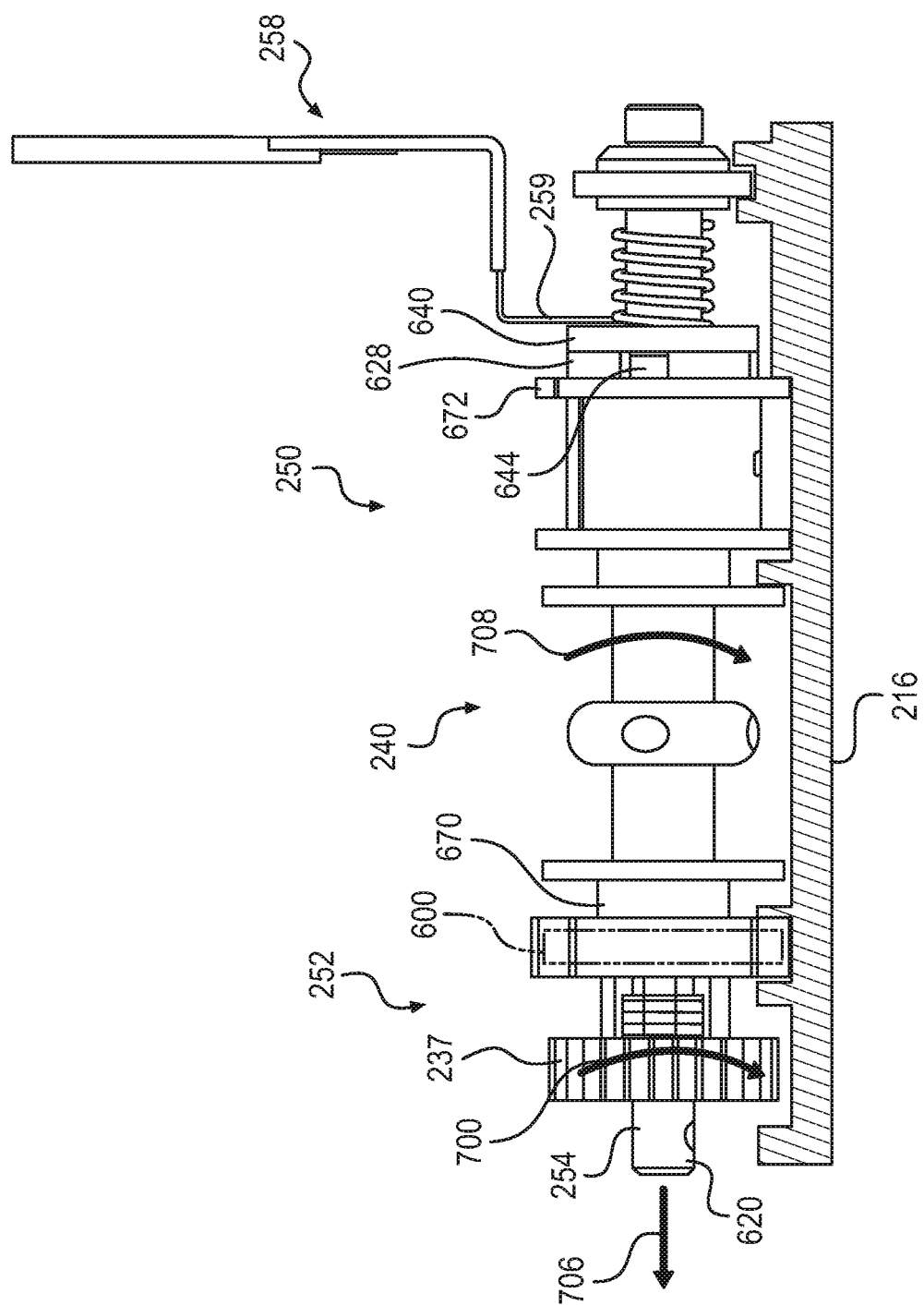
FIG. 19 is a side schematic view of an embodiment of a torque transmitting system in an incremental tightening configuration.

FIG. 19 shows the operation of torque transmitting system 250 in a configuration where spool 240 may begin to wind in lace (i.e., torque transmitting system 250 is in the incremental tighten mode). In this case, motor 220 continues to drive fourth gear 237 in the first rotational direction (indicated schematically as arrow 700), though contact with pawl member 600 prevents any further axial translation of fourth gear 237 along shaft 254. Therefore, as fourth gear 237 continues to turn, shaft 254 is translated axially (indicated schematically as arrow 706) so that first end portion 620 translates further from spool 240. As shaft 254 translates axially, flange portion 628 compresses against second end 672 of spool 240, allowing pins 644 to engage alignment holes (see FIG. 15) of spool 254. This locks shaft 254 and spool 240 together and prevents relative rotation of the two components. The contact between flange portion 628 and spool 240 prevents any further axial translation of shaft 254. At this point, with ratcheting assembly 252 clamped against first end portion 670 of spool 240, further driving of fourth gear 237 acts to rotate spool 240 in the first rotational direction (indicated schematically by arrow 708). As long as motor 240 continues to drive fourth gear 237, lace may be wound onto spool 240.

It can also be seen in FIG. 19 that as flange 628 moves towards spool 240 and engagement plate 640 follows under the force of compression spring 642, limit switch assembly 258 is separated from engagement plate 640. This breaks the continuity of current between contacts 259.

Figure 21:
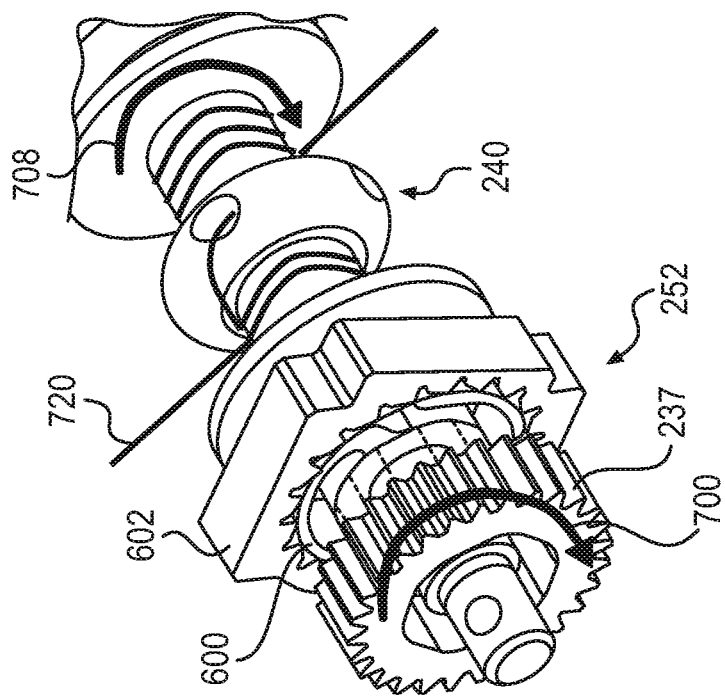
FIG. 21 is a schematic isometric view of the portion of torque transmitting system of FIG. 20, in which the gear, ratcheting assembly and spool are clamped together and the spool is rotated.
Figure 20:
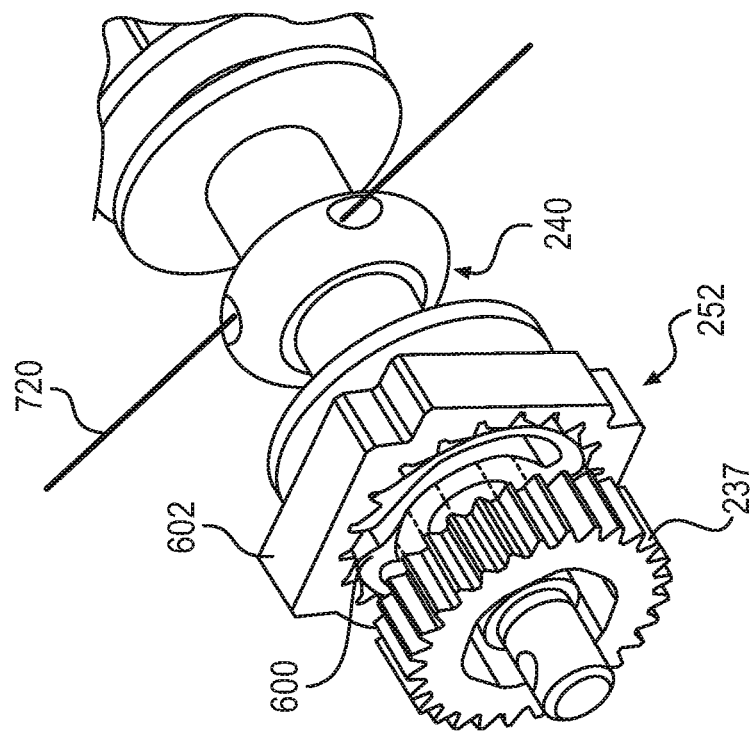
FIG. 20 is a schematic isometric view of a portion of a torque transmitting system as a gear contacts a ratcheting assembly.
Figure 22:
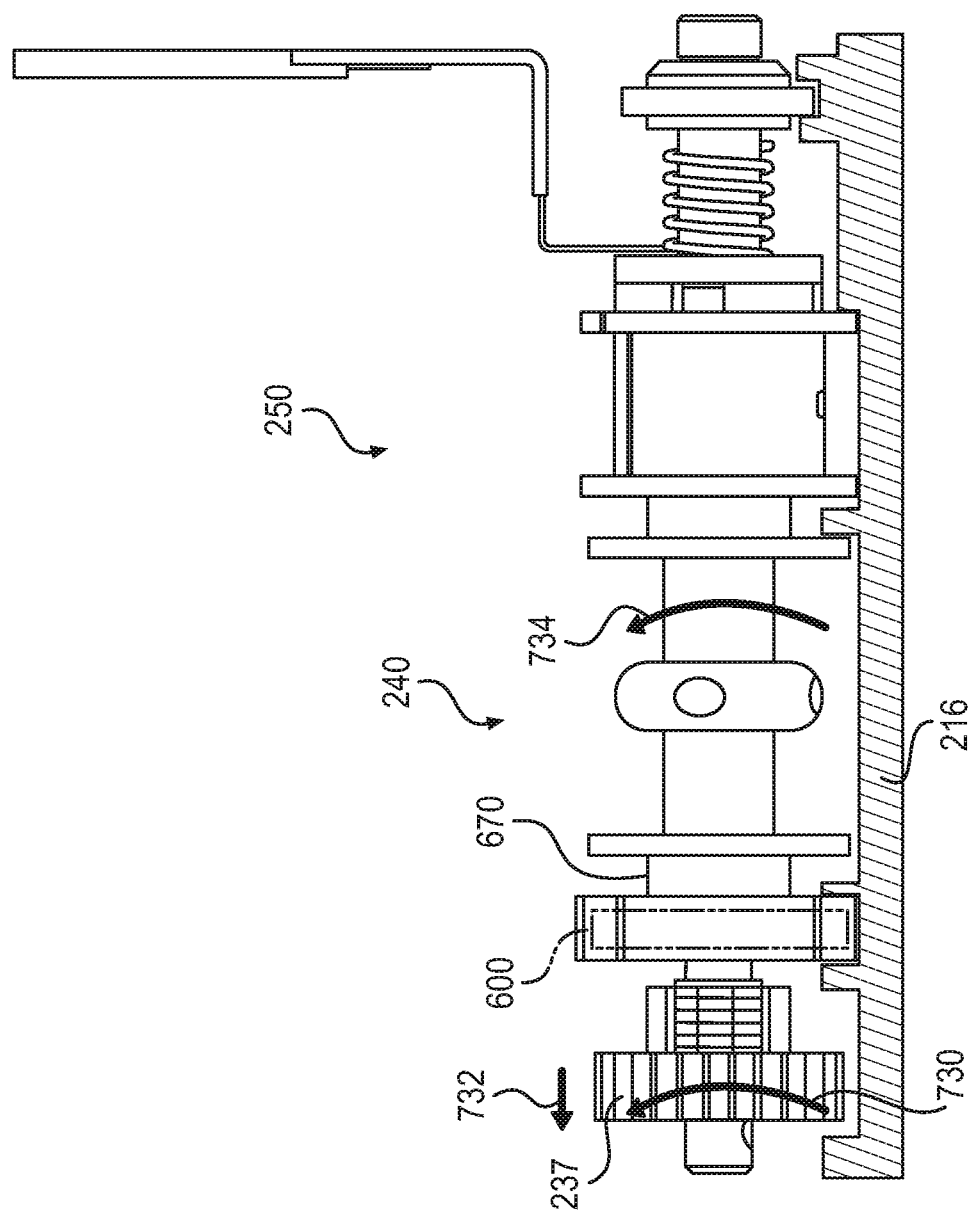
FIG. 22 is a side schematic isometric view of a torque transmitting system in an incremental loosening configuration.
Figure 24:
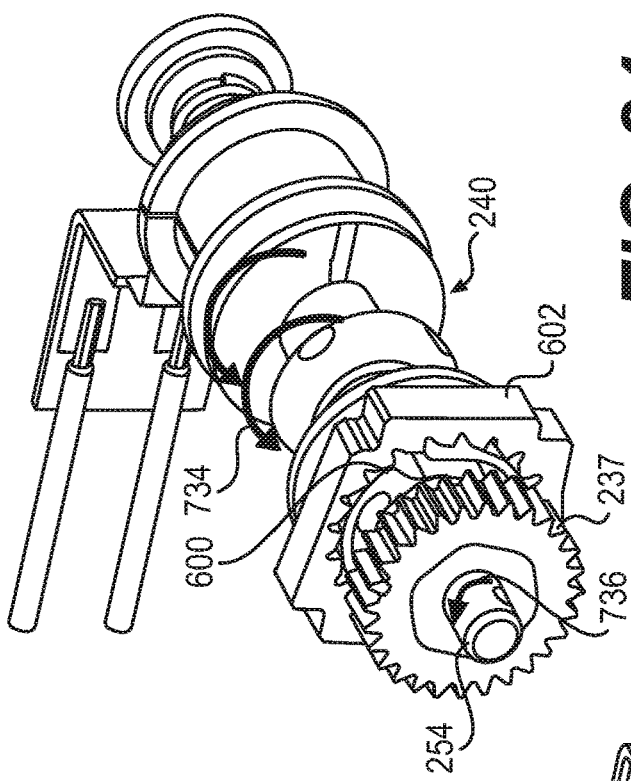
FIG. 24 is a schematic isometric view of a torque transmitting system in a second stage of an incremental loosening configuration.
Figure 25:
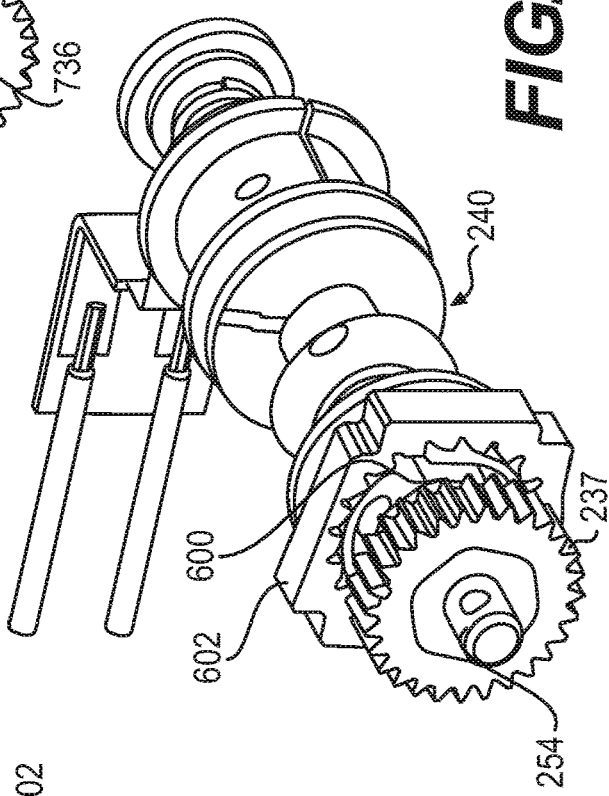
FIG. 25 is a schematic isometric view of a torque transmitting system in a third stage of an incremental loosening configuration.
Figure 23:
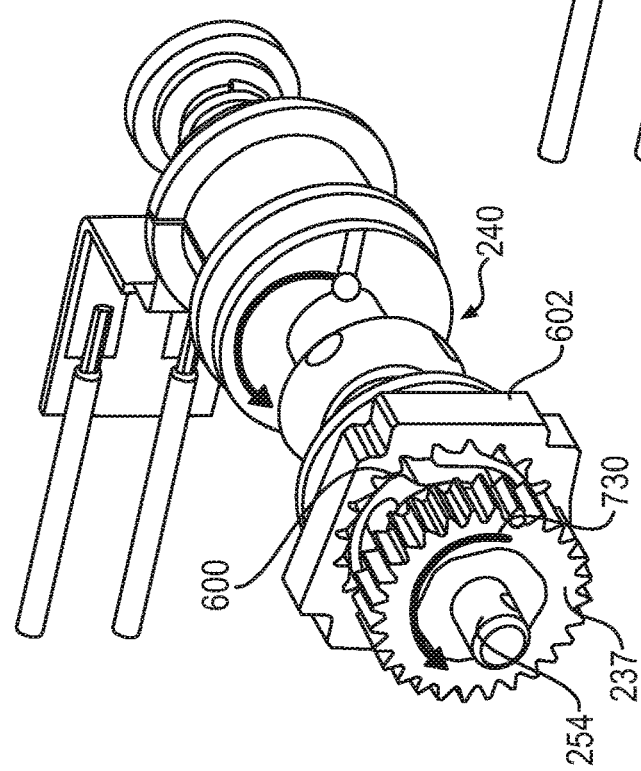
FIG. 23 is a schematic isometric view of a torque transmitting system in a first stage of an incremental loosening configuration.

FIGS. 20 and 21 illustrate close up schematic views of some components. For purposes of illustration, a schematic lace 720 is shown with spool 240. Referring to FIGS. 20 and 21, ratcheting assembly 252 ensures that torque can only be transmitted from fourth gear 237 to pawl member 600 and spool 240, and not vice versa. In particular, the one-way operation of ratcheting assembly 252 prevents torque generated by spool 240 from turning pawl member 600, fourth gear 237 and ultimately motor 220. In other words, as previously described, ratcheting assembly 252 functions as a load-holding mechanism that prevents spool 240 from unintentionally rotating in the second rotational direction (i.e., the unwinding direction). This arrangement may help prevent spool 240 from back winding motor 220 in situations where motor 220 stops or the torque applied to spool 240 by the lace exceeds to torque applied to the spool by fourth gear 237.

FIGS. 22-25 show the operation of torque transmitting system 250 in an incremental loosen mode. In some embodiments, incremental loosening may occur in several stages. During a first stage, shown in FIGS. 22 and 23, motor 220 is operated to drive fourth gear 237 in the second rotational direction (indicated schematically as arrow 730). This causes fourth gear 237 to translate axially away from pawl member 600 and spool 240 in a direction indicated schematically by arrow 732. As fourth gear 237 translates away from pawl member 600, the clamping force between fourth gear 237, pawl member 600 and first end 670 of spool 240 is released. During a second stage, shown in FIG. 24, tension in the lace then causes spool 240 to rotate in the second rotational direction (indicated schematically by arrow 734). Because spool 240 and shaft 254 are physically locked together at this stage, shaft 254 rotates along with spool 240 in the second rotational direction (indicated schematically by arrow 736). As shaft 254 rotates the threaded engagement between shaft 254 and fourth gear 237 (as well as the resistance to the rotation of fourth gear 237 provided by gear reduction system 228 and motor 220) causes fourth gear 237 to translate axially towards pawl member 600. In the last stage, shown in FIG. 25, fourth gear 237, pawl member 600 and spool 240 are clamped together, which prevents spool 240 from further rotation in the second rotational direction. These three stages may be repeated in succession to incrementally unwind lace from spool 240.

Figure 26:
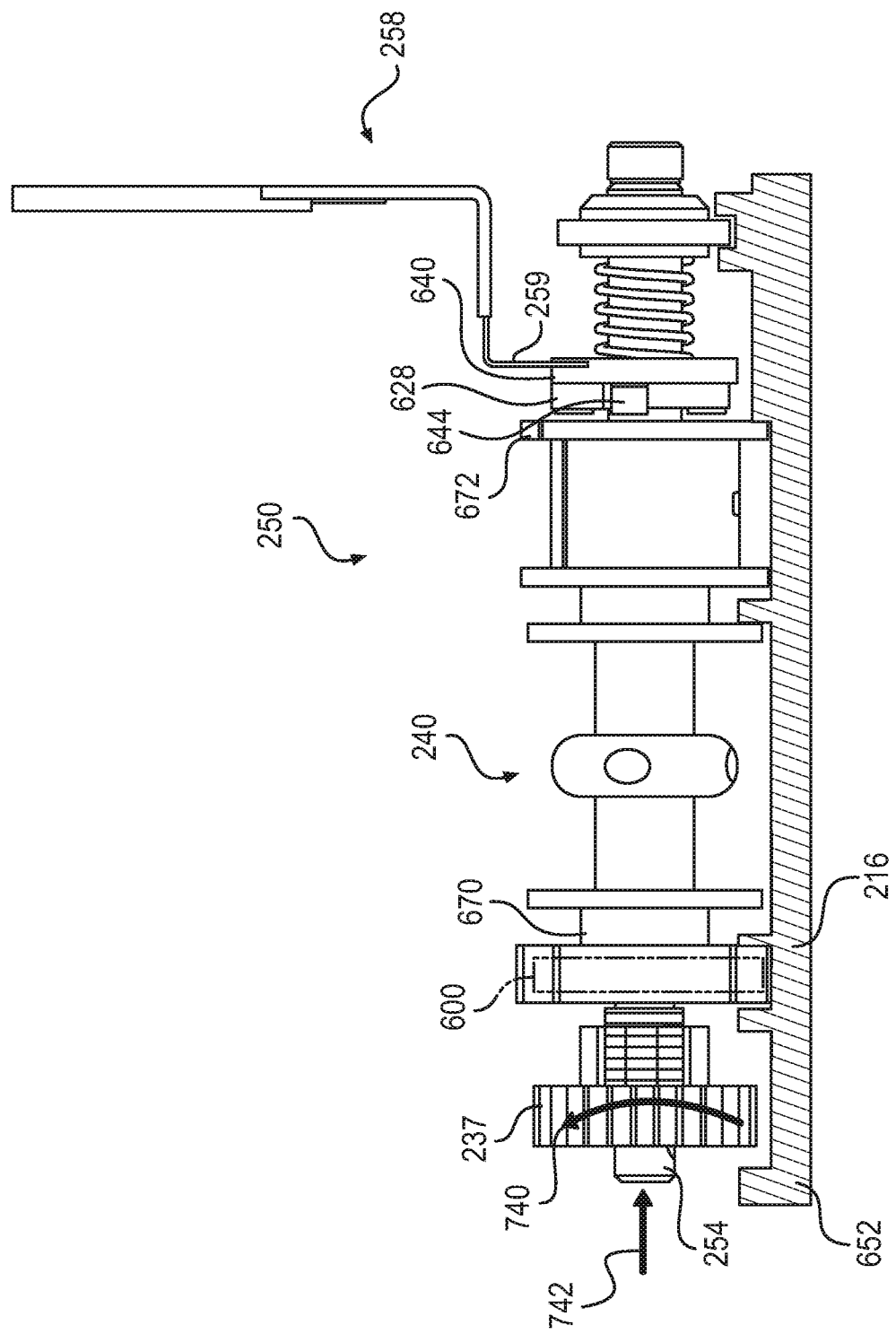
FIG. 26 is a schematic side view of an embodiment of a torque transmitting system transitioning to a full loosening configuration.

FIG. 26 shows the operation of torque transmitting system 250 in a fully loosen mode (or full release mode). Referring to FIG. 26, motor 220 may drive fourth gear 237 to rotate in the second rotational direction (indicated schematically by arrow 740) until the lace tension is low enough that spool 240 no longer unwinds. In some embodiments, fourth gear 237 may continue to rotate until fourth gear 237 encounters a hard stop provided by wall portion 652 of inner housing portion 216. With fourth gear 237 unable to translate further, continued driving of fourth gear 237 by motor 220 results in shaft 254 translating axially in the direction indicated schematically by arrow 742 until engagement plate 628 is no longer locked with spool 240 (i.e., until pins 644 disengaged from alignment holes 650 of spool 240). At this point, engagement plate 640 touches contacts 259 of limit switch assembly 258, thereby completing the limit switch continuity, which further causes motor 220 to stop. This leaves spool 240 in a fully loosened state and able to rotate relatively freely, though with some biasing in the first rotational direction provided by secondary winding assembly 260.

A secondary winding assembly may be configured to operate substantially independently of a torque transmitting system. This may allow the winding assembly to draw in slack during various stages of operation of the torque transmitting system. In particular, the secondary winding assembly may be configured to draw in slack in a tensile member (e.g., lace), which could occur during tightening, loosening and fully loosening of the tensile member.

Figure 27:
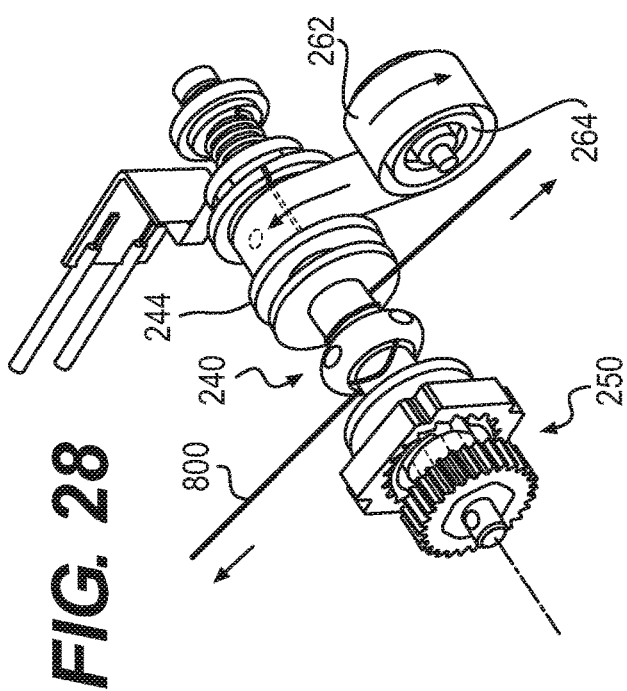
FIG. 27 is a schematic isometric view of a secondary winding assembly operating while a lace is being wound onto a spool.
Figure 28:
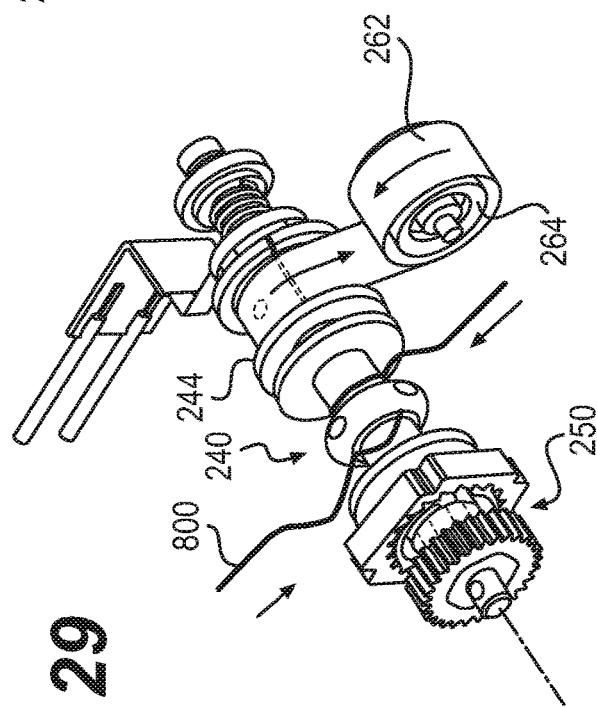
FIG. 28 is a schematic isometric view of a secondary winding assembly operating while a lace is being unwound from a spool due to tension on the lace.
Figure 29:
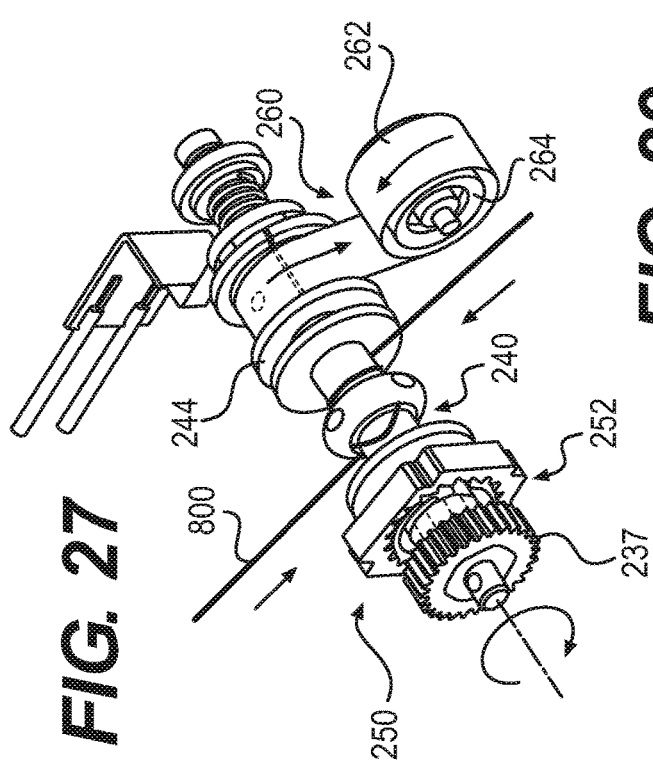
FIG. 29 is a schematic isometric view of a secondary winding assembly operating when a lace has developed some slack near the spool.

FIGS. 27 through 29 illustrate schematic isometric views of some portions of motorized tightening device 160. More specifically, FIGS. 27 through 29 are intended to illustrate the general operation of secondary winding assembly 260 during different operating modes of the system. FIG. 27 illustrates a configuration of motor tightening device 160 operating in a tightening mode. In this mode, fourth gear 237, in cooperation with torque transmitting system 250, drives spool 240 in a first rotational direction and thereby winds lace 800 around spool 240. In this mode, spring member 262 may be wound from spool 240 to spring bearing 264 as spool 240 is driven by the motor.

Referring next to FIG. 28, when motorized tightening device 160 operates in a fully loosened mode, the tension of lace 800 rotates spool 240 in the second winding direction and unwinds lace 800 from spool 240. As spool 240 winds in the second rotational direction, spring member 262 may unwind from spring bearing 264 and onto second receiving portion 244 of spool 240. This allows spring member 262 to return to a default configuration, in which secondary winding assembly 260 tends to bias spool 240 in the winding direction to draw in slack.

Referring next to FIG. 29, motorized tightening device 160 is operating in a mode where no torque is being supplied to spool 240 by a motor. In addition, slack has developed in lace 800 so that lace 800 is not applying much torque to spool 240 either. In this situation, secondary winding assembly 260 provides a biasing force to wind spool 240 in the first rotational direction, as spring member 262 unwinds from second receiving portion 244 of spool 240 and onto spring bearing 264.

Figure 30:
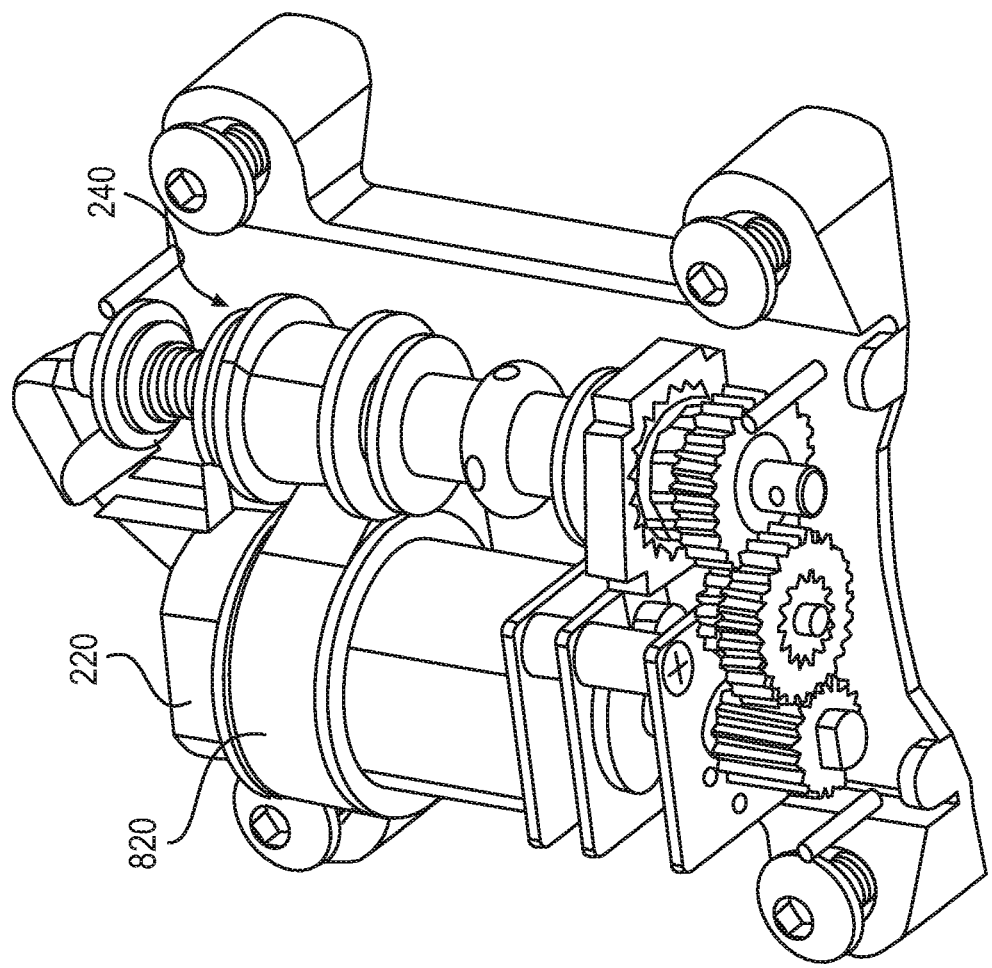
FIG. 30 is a schematic isometric view of motorized tensioning device including an alternative configuration for a secondary winding assembly.

Secondary winding assembly 260 may improve usability of tensioning system 150, by ensuring that slack is rapidly wound up when motor 220 is disengaged. This is desirable so a user can quickly put the article on or take the article off without having to wait for the motor to wind in slack. In the embodiment shown, this rapid slack winding is accomplished using constant force spring that is stored on a freewheeling spool and rewound onto one end of the lace spool. However, in other embodiments, a variety of different elements or systems could be used for this rapid slack winding. For example, in another embodiment a second small motor with either no reduction or light gear reduction could be used for slack winding. In still other embodiments, other spring elements could be used. For example, in another embodiment, an elastomeric torsion spring could be used. In still another embodiment, a geared clock spring could be used. Moreover, in other embodiments, a spring member could be wound onto other components of a tightening system. For example, in the alternative embodiment shown in FIG. 30, spring member 820 is configured to wind around spool 240 at one end, and around motor 220 at another. This alternative arrangement may provide a slightly more compact configuration for a motorized tightening system. In addition to improving the speed of fully winding and unwinding the lace, battery life may be greatly improved over systems that utilize a motor to completely wind and unwind a lace.

The location of a motorized tensioning device can vary from one embodiment to another. The illustrated embodiments show a motorized tensioning device disposed on the heel of an upper. However, other embodiments may incorporate a motorized tensioning device in any other location of an article of footwear, including the forefoot and midfoot portions of an upper. In still other embodiments, a motorized tensioning device could be disposed in a sole structure of an article. The location of a motorized tensioning device may be selected according to various factors including, but not limited to: size constraints, manufacturing constraints, aesthetic preferences, optimal lacing placement, ease of removability as well as possibly other factors.

In embodiments where motorized tensioning device 160 is disposed externally on upper 102, a wearer may access components by removing a portion of housing unit 212 (see FIG. 1). For example, in some cases spool 240 may be replaceable in the event of a broken lace.

Some embodiments may include provisions for incorporating a motorized tensioning device into removable components of an article. In one embodiment, a motorized tensioning device may be incorporated into an external heel counter. In some cases, an external heel counter may function as a harness for mounting a motorized tensioning device to an article. In such embodiments, the external heel counter may be specially adapted to receive a motorized tensioning device. An example of a heel counter configured for use with a lace tensioning device is disclosed in Gerber, U.S. Patent Application Publication No. 20130312293, (now U.S. patent application Ser. No. 13/481,132, filed May 25, 2012 and titled "Article of Footwear with Protective Member for a Control Device"), the entire disclosure of which is incorporated herein by reference.

Figure 31:
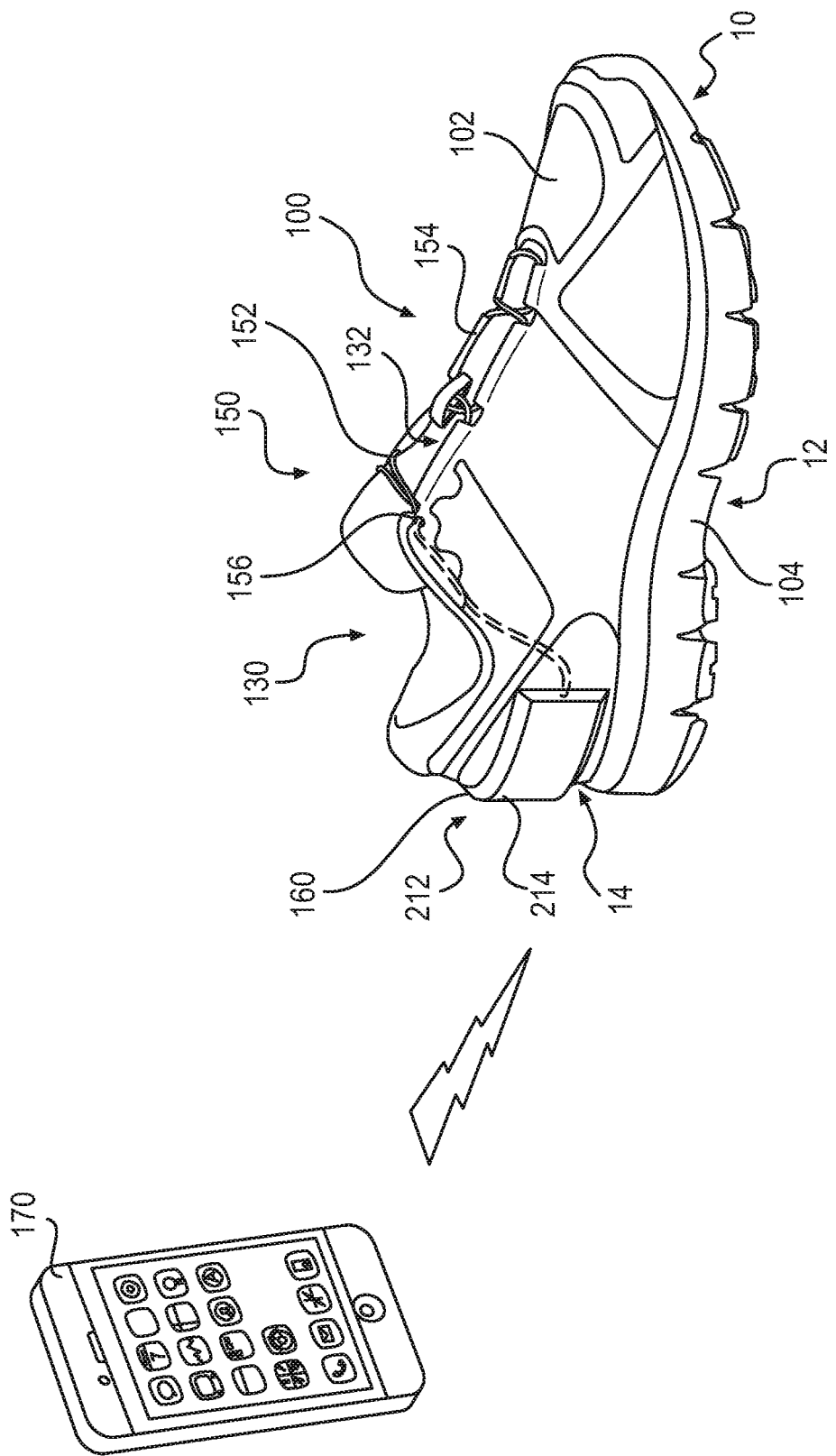
FIG. 31 is a schematic isometric view of an embodiment of an article of footwear with a tensioning system and a remote device for controlling the tensioning system.

FIG. 31 illustrates a schematic isometric view of an embodiment of article of footwear 100 that is configured with a tensioning system 150. In the current embodiment, article of footwear 100, also referred to hereafter simply as article 100, is shown in the form of an athletic shoe, such as a running shoe. However, in other embodiments, tensioning system 150 may be used with any other kind of footwear including, but not limited to: hiking boots, soccer shoes, football shoes, sneakers, running shoes, cross-training shoes, rugby shoes, basketball shoes, baseball shoes as well as other kinds of shoes. Moreover, in some embodiments article 100 may be configured for use with various kinds of non-sports related footwear, including, but not limited to: slippers, sandals, high heeled footwear, loafers as well as any other kinds of footwear. As discussed in further detail below, a tensioning system may not be limited to footwear and in other embodiments a tensioning system could be used with various kinds of apparel, including clothing, sportswear, sporting equipment and other kinds of apparel. In still other embodiments, a tensioning system may be used with braces, such as medical braces.

Article 100 may include upper 102 and sole structure 104. Generally, upper 102 may be any type of upper. In particular, upper 102 may have any design, shape, size and/or color. For example, in embodiments where article 100 is a basketball shoe, upper 102 could be a high top upper that is shaped to provide high support on an ankle. In embodiments where article 100 is a running shoe, upper 102 could be a low top upper.

In some embodiments, sole structure 104 may be configured to provide traction for article 100. In addition to providing traction, sole structure 104 may attenuate ground reaction forces when compressed between the foot and the ground during walking, running or other ambulatory activities. The configuration of sole structure 104 may vary significantly in different embodiments to include a variety of conventional or non-conventional structures. In some cases, the configuration of sole structure 104 can be configured according to one or more types of ground surfaces on which sole structure 104 may be used. Examples of ground surfaces include, but are not limited to: natural turf, synthetic turf, dirt, as well as other surfaces.

In different embodiments, sole structure 104 may include different components. For example, sole structure 104 may include an outsole, a midsole, and/or an insole. In addition, in some cases, sole structure 104 can include one or more cleat members or traction elements that are configured to increase traction with a ground surface.

In some embodiments, sole structure 104 may be joined with upper 102. In some cases, upper 102 is configured to wrap around a foot and secure sole structure 104 to the foot. In some cases, upper 102 may include opening 130 that provides access to an interior cavity of article 100.

Tensioning system 150 may comprise various components and systems for adjusting the size of opening 130 and thereby tightening (or loosening) upper 102 around a wearer's foot. In some embodiments, tensioning system 150 may comprise lace 152 as well as motorized tensioning device 160. Lace 152 may be configured to pass through various different lacing guides 154, which may be further associated with the edges of throat opening 132. In some cases, lacing guides 154 may provide a similar function to traditional eyelets on uppers. In particular, as lace 152 is pulled or tensioned, throat opening 132 may generally constrict so that upper 102 is tightened around a foot.

The arrangement of lacing guides 154 in this embodiment is only intended to be exemplary and it will be understood that other embodiments are not limited to a particular configuration for lacing guides 154. Furthermore, the particular types of lacing guides 154 illustrated in the embodiments are also exemplary and other embodiments may incorporate any other kinds of lacing guides or similar lacing provisions. In some other embodiments, for example, lace 154 could be inserted through traditional eyelets. Some examples of lace guiding provisions that may be incorporated into the embodiments are disclosed in Cotterman et al., U.S. Patent Application Publication Number 2012/0000091, published Jan. 5, 2012 and entitled "Lace Guide," the disclosure of which is incorporated herein by reference in its entirety. Additional examples are disclosed in Goodman et al., U.S. Patent Application Publication Number 2011/0266384, published Nov. 3, 2011 and entitled "Reel Based Lacing System" (the "Reel Based Lacing Application"), the disclosure of which is incorporated herein by reference in its entirety. Still additional examples of lace guides are disclosed in Kerns et al., U.S. Patent Application Publication Number 2011/0225843, published Sep. 22, 2011 and entitled "Guides For Lacing Systems," the disclosure of which is incorporated herein by reference in its entirety.

Lace 152 may comprise any type of type of lacing material known in the art. Examples of lace that may be used include cables or fibers having a low modulus of elasticity as well as a high tensile strength. A lace may comprise a single strand of material, or can comprise multiple strands of material. An exemplary material for the lace is SPECTRA™, manufactured by Honeywell of Morris Township N.J., although other kinds of extended chain, high modulus polyethylene fiber materials can also be used as a lace. Still further exemplary properties of a lace can be found in the Reel Based Lacing Application mentioned above.

In some embodiments, lace 152 may be passed through lacing guides 154 and may pass through internal channels (not shown) within upper 102 after entering channel openings 156 that are above lacing guides 154. In some embodiments, the internal channels extend around the sides of upper 102 and guide the lace towards motorized tensioning device 160, which may be mounted on heel portion 14 of upper 102. In some cases, motorized tensioning device 160 may include provisions for receiving portions of lace 152. In some cases, end portions of lace 152 exit internal channels of upper 102 and pass through apertures in a housing unit 212 of motorized tensioning device 160.

Motorized tensioning device 160 may be configured to automatically apply tension to lace 152 for purposes of tightening and loosening upper 102. As described in further detail below, motorized tensioning device 160 may include provisions for winding lace 152 onto, and unwinding lace 152 from, a spool internal to motorized tensioning device 160. Moreover, the provisions may include an electric motor that automatically winds and unwinds the spool in response to various inputs or controls.

Provisions for mounting motorized tensioning device 160 to upper 102 can vary in different embodiments. In some cases, motorized tensioning device 160 may be removably attached, so that motorized tensioning system 160 can be easily removed by a user and modified (for example, when a lace must be changed). Examples of provisions for removably attaching motorized tensioning system 160 to upper 102 are discussed in detail later. In other cases, motorized lacing device 160 could be permanently attached to upper 102. In one embodiment, for example, an external harness (not shown) may be used to mount motorized tensioning system 160 to upper 102 at heel portion 14.

In some embodiments, motorized tensioning device 160 may communicate with remote device 170. In some cases, motorized tensioning device 160 may receive operating instructions from remote device 170. For example, motorized tensioning device 160 may receive instructions to apply increased tension to lace 152 by winding the spool. In some cases, remote device 170 may be capable of receiving information from motorized tensioning device 160. For example, remote device 170 could receive information related to the current tension in lace 152 and/or other sensed information. As discussed below in reference to FIG. 32, remote device 170 may function as a remote control that may be used by the wearer to operate tensioning system 150.

In one embodiment, remote device 170 comprises a mobile phone, such as the iPhone made by Apple, Inc. In other embodiments, any other kinds of mobile phones could also be used including smartphones. In other embodiments, any portable electronic devices could be used including, but not limited to: personal digital assistants, digital music players, tablet computers, laptop computers, ultrabook computers as well as any other kinds of portable electronic devices. In still other embodiments, any other kinds of remote devices could be used including remote devices specifically designed for controlling motorized tensioning device 160. In another embodiment, discussed in detail below, remote device 170 could comprise a bracelet, wristband and/or armband that is worn by a user and specifically designed for communicating with motorized tensioning device 160. The type of remote device could be selected according to software and hardware requirements, ease of mobility, manufacturing expenses, as well as possibly other factors.

In some embodiments, motorized tightening device 160 may communicate with multiple remote devices. For example, a user may use a mobile device, such as an iPhone, at home to identify and set preferred tension settings, and another remote device, such as with a bracelet, wristband and/or armband, with more rudimentary controls might then be used to issue commands to motorized tightening device 160, for example while playing sports. For example, a bracelet might allow a user to recall a set tension and adjust it, but not set a new tension for later recall.

As already mentioned, remote device 170 may communicate with motorized tightening device 160 (or indirectly with motorized tightening device 160 via a secondary device, such as a separate control unit). Examples of different communication methods include, but are not limited to: wireless networks such as personal area networks (e.g., Bluetooth®) and local area networks (e.g., Wi-Fi) as well as any kinds of RF based methods known in the art. In some embodiments, infrared light may be used for wireless communication. Although the illustrated embodiments detail a remote device 170 that communicates wirelessly with motorized tensioning system 160, in other embodiments remote device 170 and motorized tensioning system 160 may be physically connected and communicate through one or more wires.

For purposes of clarity, a single article of footwear is shown in the embodiments. However, it will be understood that remote device 170 may be configured to operate a corresponding article of footwear which also includes a similar tensioning system (e.g., a pair of footwear each having a tensioning system). As described below, remote device 170 may be used to operate each the tensioning systems of each article independently of one another.

Figure 32:
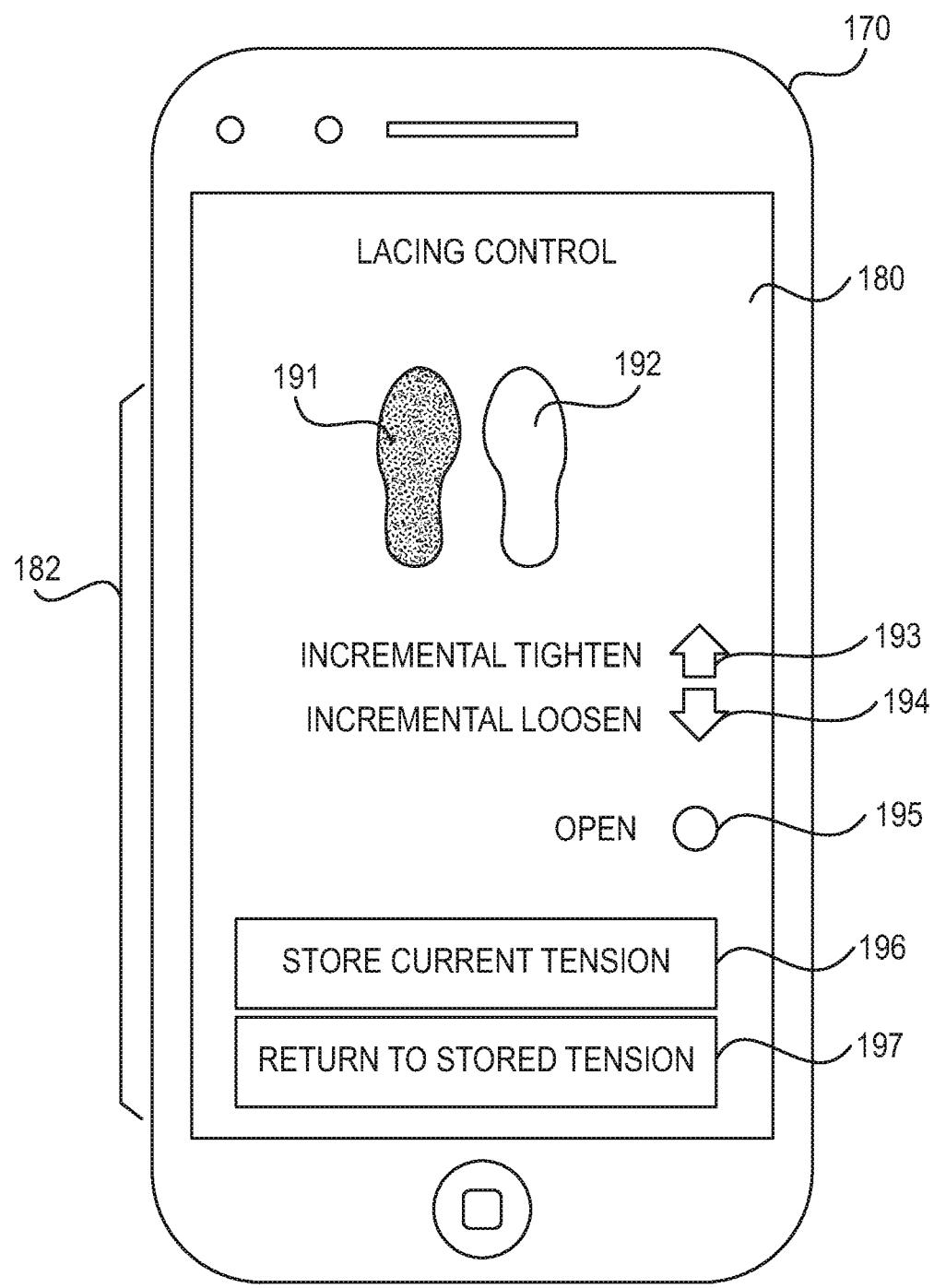
FIG. 32 is a schematic view of an embodiment of a remote device running a lacing control application.

FIG. 32 illustrates a schematic view of an embodiment of remote device 170, including a schematic representation of an exemplary user interface for controlling tensioning system 150. In some embodiments, remote device 170 may be capable of running a lacing control software application 180, hereafter referred to simply as application 180. In embodiments where remote device 170 is a mobile phone (or similar digital device) capable of running mobile software applications, application 180 may be downloaded by a user from a third party online store or website. Such a mobile phone (or similar digital device) may include a touch screen LCD device which may be used by application 180 for input and output interaction with a user. In some embodiments, an LCD or non-touch screen LCD may be used for output display only.

Application 180 may display, and respond to user interaction with, a plurality of control buttons 182 and initiate control commands in response to such interaction. Exemplary control commands may include, but are not limited to, left right shoe selection, incremental tighten, incremental loosen, open/fully loosen, store tension, and recall/restore tension. In the exemplary embodiment of FIG. 32, these control buttons include a first button 191 and a second button 192, which are respectively used to select the shoe (left or right) that will receive and respond to the control commands. In some embodiments, either first button 191 or second button 192 may be selected, but both may not be selected simultaneously. In other cases, it may be possible to select both first button 191 and second button 192 simultaneously, to allow a user to tighten, loosen, or open both shoes simultaneously. In addition, application 180 may include third button 193 for initiating an "incremental tighten" command, a fourth button 194 for initiating an "incremental loosen" command and a fifth button 195 for initiating an "open" (or fully loosen) command. Optionally, some embodiments could include a "fully tighten" command that would tighten the footwear until a predetermined threshold is achieved (for example, a threshold pressure, winding distance, etc.).

In some embodiments, a shoe, article, or other item may include more than one motorized tightening device 160. In such embodiments, each motorized tightening device 160 may include wireless communication hardware for separately communicating with a remote device 170, or a single wireless communication device may be provided for common use by multiple motorized tightening devices 160. For such embodiments, remote device 170 may be configured, such as with application 180, to provide additional buttons or other controls to individually adjust plural motorized tightening devices 160 on a single article. For example, button 191 illustrated in FIG. 32 could be subdivided into a top region and lower region which are separately responsive to user interaction. By use of these regions, one of two motorized tightening devices 160 could be selected for tension adjustment via buttons 193, 194, and 195. In another example, additional buttons like buttons 193 and 194 could be displayed at the same time by application 180, allowing for more rapid adjustment of multiple motorized tightening devices 160.

Application 180 may also include provisions for storing and using preferred tension settings. For example, sixth button 196 and seventh button 197 may be used to initiate a "store current tension" command and a "return to stored tension" command, respectively. In some cases, the tension values could be stored at the remote device, while in other cases the tension values could be stored in internal memory of a control board for the motorized tensioning device 160. Still other embodiments could include provisions for storing multiple tension settings. For example, a user may prefer a tighter fit for playing sports and a looser fit for casual activities. In such cases, remote device 170 may allow a user to store two or more tension settings, corresponding to at least two different lace tension preferences. In some embodiments, sixth button 196 may cause the tension setting for a single, currently selected, motorized tightening device 160 to be stored, and in some embodiments sixth button 196 may cause the tension settings for multiple motorized tightening devices 160 to be stored in a single action. Those skilled in the art appreciate that storage or recall of tensions for multiple motorized tightening devices 160, whether part of a single item or multiple items, such as a pair of shoes, may be performed with a single command issued by a remote device 170 or with a series of control commands, such as by issuing separate control commands to each motorized tightening device 160.

In some embodiments, application 180 and/or remote device 170 may be configured to selectively control individual items or individual sets of items, such as a pair of shoes, from among multiple items or sets of items within communication range of remote device 170. For example, application 180 may be configured to enumerate items by unique identifiers assigned to each item, display the enumerated items to a user, and receive an input selecting an item. In another example, an application 180 may be paired via Bluetooth® with a particular item or set of items. In another example, a remote device without an LCD display may include a control button that may be pressed, repeatedly if needed, to select a desired item, and the item may include an LED which is illuminated when it is in wireless communication with the remote device.

The embodiments are not limited to a particular user interface or application for remotely operating motorized tensioning device 160. The embodiments here are intended to be exemplary, and other embodiments could incorporate any additional control buttons, interface designs and software applications. As one example, some embodiments may not include provisions for selecting the shoe to be controlled, and instead could utilize two sets of control buttons, where each set corresponds to either the left or right shoe. The control buttons for initiating various operating commands can be selected according to various factors including: ease of use, aesthetic preferences of the designer, software design costs, operating properties of the motorized tensioning device 160 as well as possibly other factors.

Throughout the detailed description and in the claims, various operating modes, or configurations, of a tensioning system are described. These operating modes may refer to states of the tensioning system itself, as well as to the operating modes of individual subsystems and/or components of the tensioning system. Exemplary modes include an "incremental tighten mode", an "incremental loosen mode" and a "fully loosen" mode. The latter two modes may also be referred to as an "incremental release mode" and a "full release mode". In the incremental tighten mode, motorized tightening device 160 may operate in a manner that incrementally (or gradually) tightens, or increases the tension of, lace 152. In the incremental loosen mode, motorized tightening device 160 may operate in a manner that incrementally (or gradually) loosens, or releases tension in, lace 152. As discussed further below, the incremental tighten mode and the incremental loosen mode may tighten and loosen a lace in discrete steps or continuously. In the full release mode, motorized tightening device 160 may operate in a manner so that tension applied to the lace by the system is substantially reduced to a level where the user can easily remove his or her foot from the article. This is in contrast to the incremental release mode, where the system operates to achieve a lower tension for the lace relative to the current tension, but not necessarily to completely remove tension from the laces. Moreover, while the full release mode may be utilized to quickly release lace tension so the user can remove the article, the incremental release mode may be utilized to make minor adjustments to the lace tension as a user searches for the desired amount of tension. Although the embodiments describe three possible modes of operation (and associated control commands), other operating modes may also be possible. For example, some embodiments could incorporated a fully tighten operating mode where motorized tightening device 160 continues to tighten lace 152 until a predetermined tension has been achieved.

FIGS. 33 through 37 illustrate schematic views of an embodiment of article 100 being tightened and loosened during different operating modes of tensioning system 150. Each figure also shows a schematic view of remote device 170, including the particular control button used to initiate each operating mode.

Figure 33:
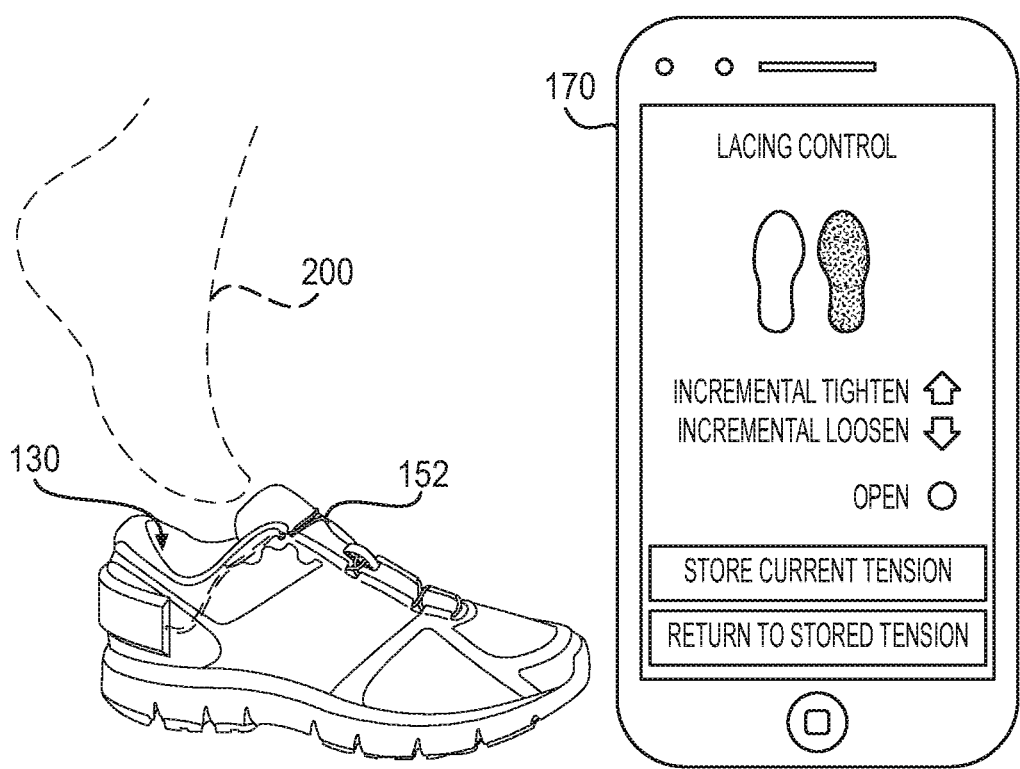
FIG. 33 is a schematic view of an embodiment of a foot being inserted into an article and a remote device running a lacing control application.
Figure 34:
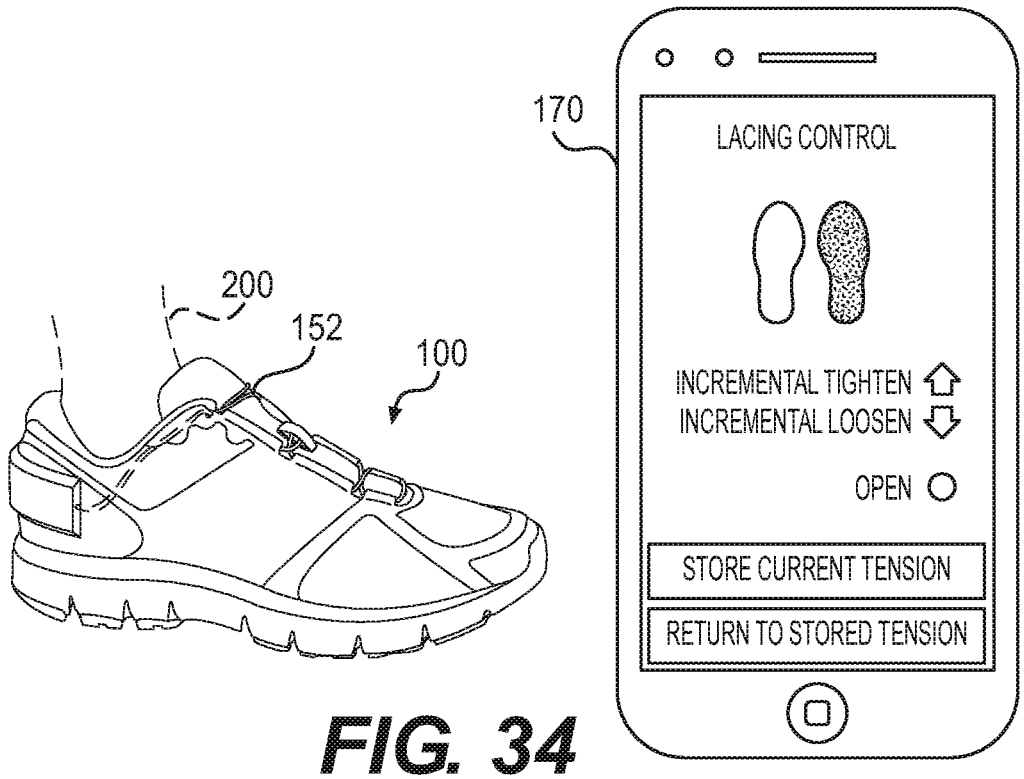
FIG. 34 is a schematic view of an embodiment of a foot fully inserted into an article and a remote device running a lacing control application.
Figure 35:
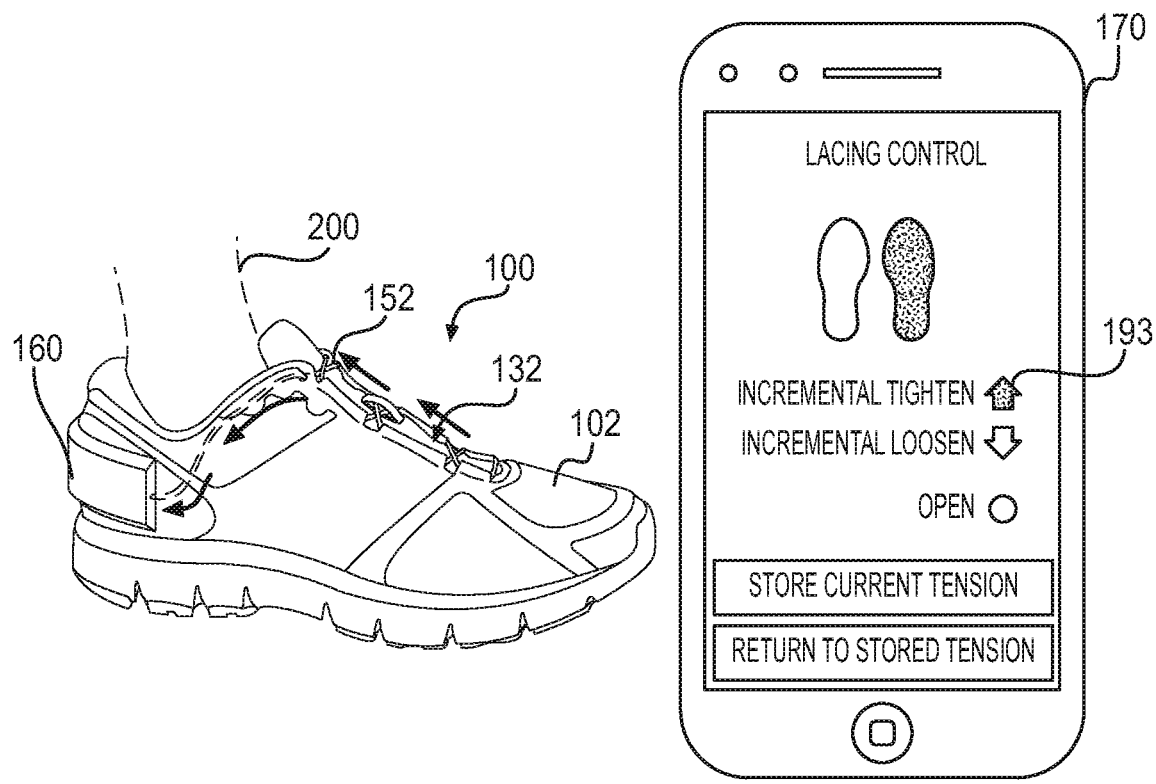
FIG. 35 is a schematic view of an embodiment of an article being tightened as a remote device sends an incremental tighten command to a tensioning system.

FIG. 33 shows article 100 is in a fully opened state just prior to the entry of foot 200. In this state, lace 152 may be loose enough to allow a user to insert his or her foot into opening 130. Referring next to FIG. 34, foot 200 is inserted into article 100, which remains in the fully opened state. Referring next to FIG. 35, an incremental tighten command has been sent to motorized tensioning device 160 by pressing third button 193 of remote device 170. This command causes motorized tensioning device 160 to enter an incremental tighten mode. At this point, the tension of lace 152 is increased to tighten upper 102 around foot 200. In particular, lace 152 is drawn into motorized tensioning device 160, which pulls on the portions of lace 152 disposed adjacent throat opening 132 and thus constricts throat opening 132. In some cases, this incremental tightening can occur in discrete steps so that each time the wearer presses third button 193, lace 152 is taken up by a predetermined amount (for example by rotating a spool within motorized tensioning device 160 through a predetermined angle). In other cases, this incremental tightening can occur in a continuous manner, as long as the wearer continues to touch third button 193. In some cases, the speed of tightening can be set so that the system does not overshoot a preferred level of tightness (i.e., the system doesn't move between not tight enough and overly tight too quickly) while also being large enough to avoid overly long times for fully tightening article 100.

Figure 36:
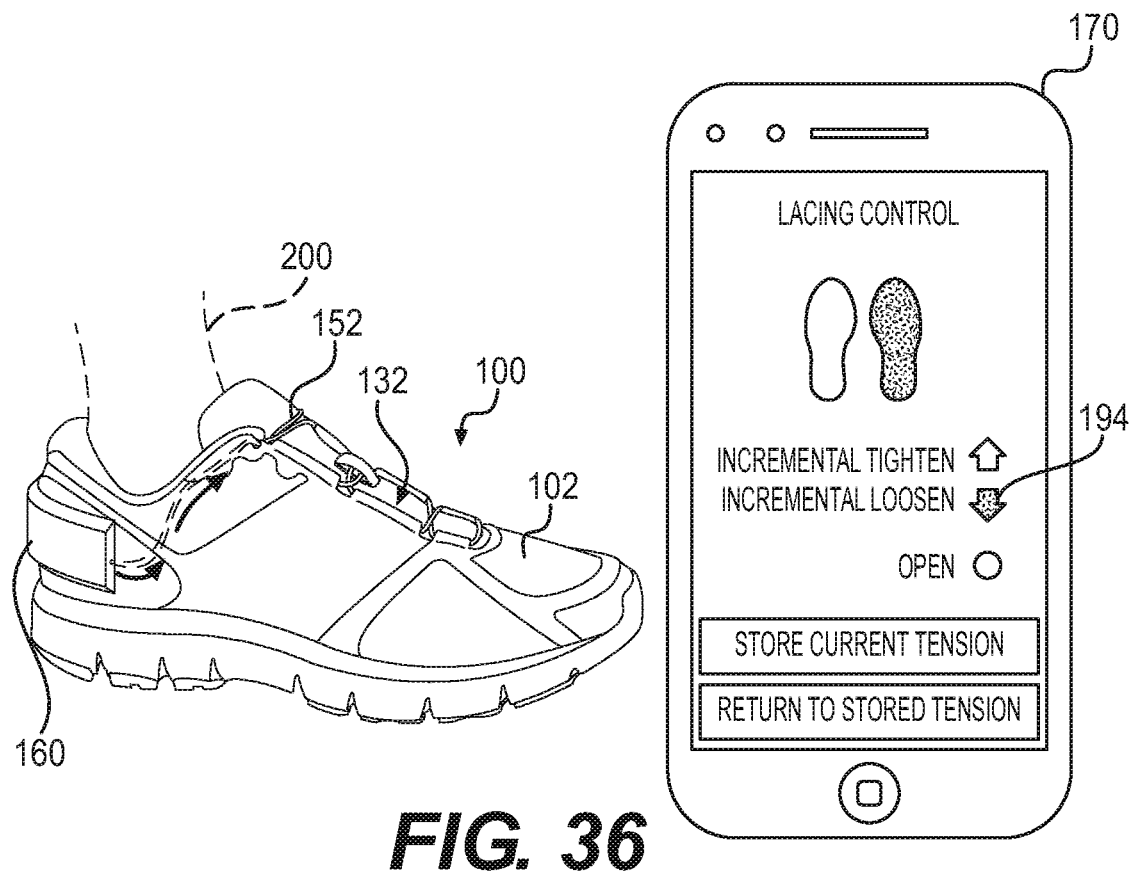
FIG. 36 is a schematic view of an embodiment of an article being loosened as a remote device sends an incremental loosen command to a tensioning system.
Figure 37:
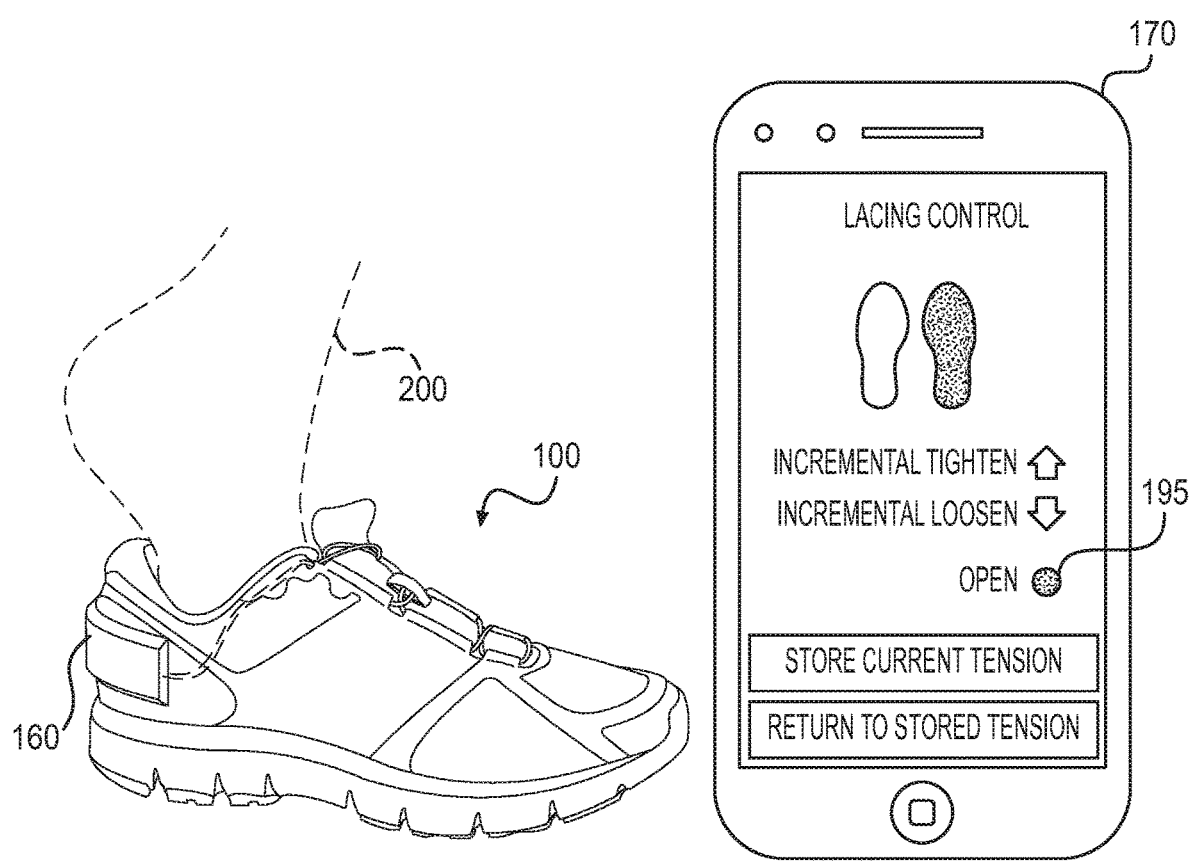
FIG. 37 is a schematic view of an embodiment of an article opened to allow a foot to be removed after a remote device has sent an open command to a tensioning system.

FIGS. 36 and 37 illustrate schematic views of two different operating modes where lace 152 may be loosened. Referring first to FIG. 36, a wearer can press fourth button 194 to initiate an incremental loosen command in tensioning system 150. Upon receiving the incremental loosen command, motorized tensioning device 160 may operate in an incremental loosen mode, in which lace 152 is released from motorized tensioning device 160 (i.e., sections of lace 152 exit from motorized tensioning device 160). This relaxes some of the tension in lace 152 and allows throat opening 132 to partially expand. In some cases, this incremental loosening can occur in discrete steps so that each time the wearer presses fourth button 194, lace 152 is let out up by a predetermined amount (for example by rotating a spool within motorized tensioning device 160 through a predetermined angle). In other cases, this incremental loosening can occur in a continuous manner, as long as the wearer continues to touch fourth button 194. In some cases, the speed of loosening can be set so that the system does not overshoot a preferred level of tightness (i.e., the system doesn't move between too tight and not tight enough too quickly) while also being large enough to avoid overly long times for fully loosening article 100. With this arrangement, a wearer can continue increasing and decreasing the tension of lace 152 (using the incremental tighten and incremental loosen modes) until a preferred level of tightness for upper 102 is achieved.

Referring next to FIG. 37, a wearer can press fifth button 195 to initiate an open, or fully loosen, command in tensioning system 150. In contrast to the incremental loosen command, the open command may be used to quickly relieve all (or most of) tension in lace 152 so that a user can quickly remove article 100. Thus, upon receiving the open command, motorized tensioning device 160 operates in a fully loosen mode. In this mode, motorized tensioning device operates to let out enough of lace 152 so that substantially all tension is removed from lace 152. In some cases, this may be achieved by continuously monitoring tension in lace 152 (for example, using sensors) and letting out lace 152 until the level of tension is below a threshold tension. In other cases, this may be achieved by letting out a predetermined length of lace 152 known to correspond approximately to the amount needed to achieve a fully loosened state for tensioning system 150. As seen in FIG. 37, with tensioning system 150 in the open state, foot 200 can be easily and comfortably removed from footwear 100.

Figure 38:
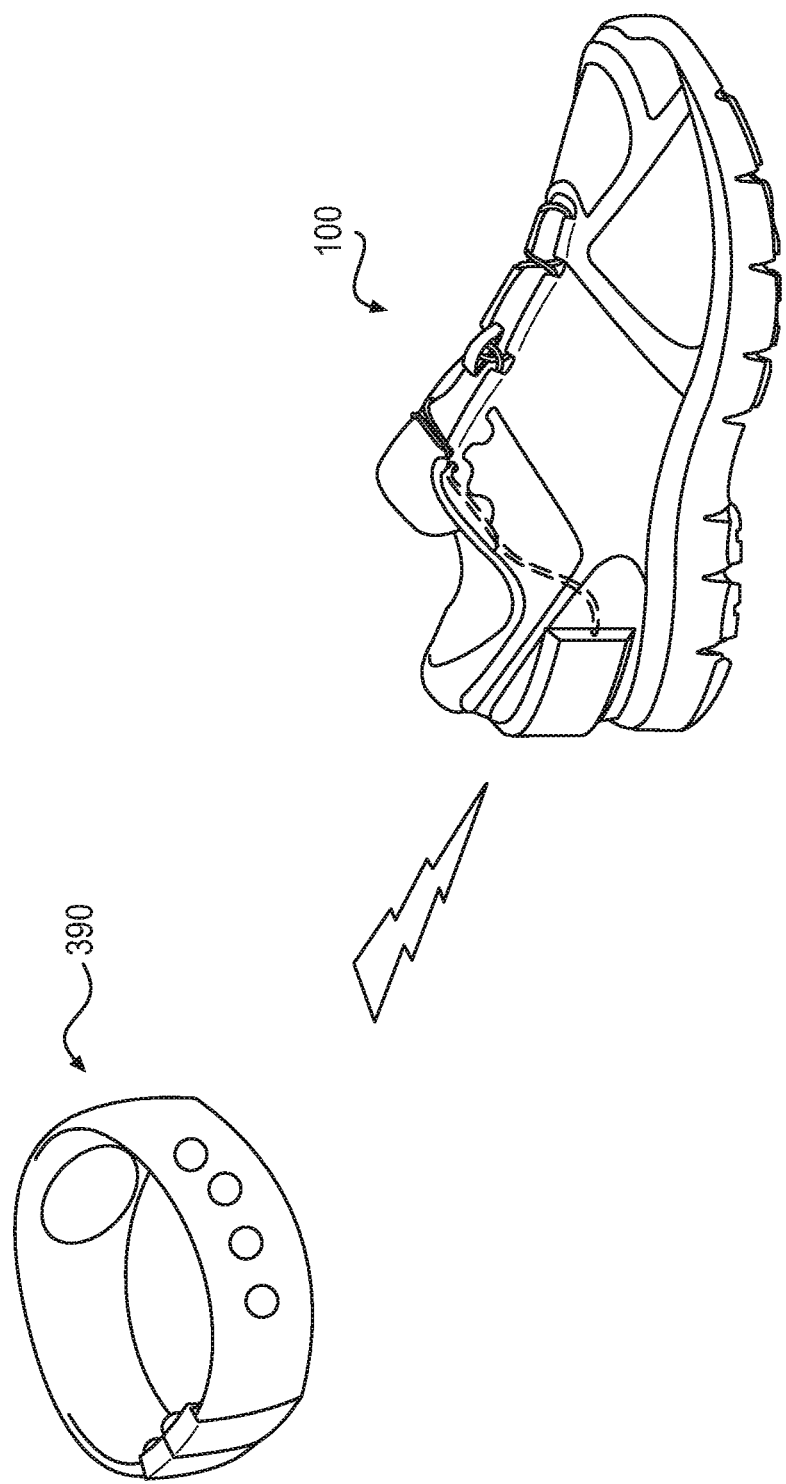
FIG. 38 is a schematic isometric view of an embodiment of an article of footwear including a tensioning system and a remote bracelet configured to control a motorized tensioning device of the tensioning system.

In different embodiments, control of a motorized lacing device can be accomplished using various methods and devices. Referring now to FIG. 38, some embodiments may utilize various kinds of remote devices, including an RF based control bracelet 390. Control bracelet 390 may incorporate one or more buttons for sending commands to a motorized tensioning device. In some cases, control bracelet 390 may include buttons for initiating incremental tightening and incremental loosening commands. In still other cases, additional buttons can be included for initiating any other commands including the open command (or fully loosen command), store tension command and return to stored tension command. Still other cases could incorporate any other buttons for issuing any other kinds of commands.

In some other embodiments, buttons for tightening, loosening and/or performing other functions can be located directly on an article. As an example, some embodiments could incorporate one or more buttons located on or adjacent to the housing of a motorized tensioning device. In still other embodiments, a motorized tightening device maybe controlled using voice commands. These commands could be transmitted through a remote device, or to a device capable of receiving voice commands that is integrated into the article and in communication with the motorized tensioning device.

Embodiments can incorporate a variety of sensors for providing information to a control unit of a motorized tensioning system. As described above, in some embodiments an Ft-bridge mechanism is used to measure current. The measured current is provided as an input to control unit 302 (see FIG. 5). In some cases, a predetermined current may be known to correspond to a certain lace tension. By checking the measured current against the predetermined current, a motorized tensioning system may adjust the tension of a lace until the predetermined current is measured, which indicates the desired lace tension has been achieved.

With current as a feedback, a variety of digital control strategies can be used. For instance, proportional control only could be used. Alternatively, PI control could be used or full PID. In cases some cases, simple averaging could be used or other filtering techniques including fuzzy logic and band-pass to reduce noise.

Still other embodiments can include additional types of sensors. In some cases, pressure sensors could be used under the insoles of an article to indicate when the user is standing. A motorized tensioning system can be programmed to automatically loosen the tension of the lace when the user moves from the standing position to a sitting position. Such a configuration may be useful for older adults that may require low tension when sitting to promote blood circulation but high tension for safety when standing.

Still other embodiments could include additional tension sensing elements. In one embodiment, three point bend indicators could be used in the lace to more accurately monitor the state of the tensioning system, including the lace. In other embodiments, various devices to measure deflection such as capacitive or inductive devices could be used. In some other embodiments, strain gauges could be used to measure tension induced strain in one or more components of a tensioning system.

In some embodiments, sensors such as gyroscopes and accelerometers could be incorporated into a tensioning system. In some embodiments, an accelerometer and/or gyroscope could be used to detect sudden moment and/or position information that may be used as feedback for adjusting lace tension. These sensors could also be implemented to control periods of sleep/awake to extend battery life. In some cases, for example, information from these sensors could be used to reduce tension in a system when the user is inactive, and increase tension during periods of greater activity.

Some embodiments may use memory (for example onboard memory associated with a control unit) to store sensed data over time. This data may be stored for later upload and analysis. For example, one embodiment of an article of footwear may sense and store tension information over time that can be later evaluated to look at trends in tightening.

It is also contemplated that some embodiments could incorporate pressure sensors to detect high pressure regions that may develop during tightening. In some cases, the tension of the lace could be automatically reduced to avoid such high pressure regions. Additionally, in some cases, a system could prompt a user to alter them to these high pressure regions and suggest ways of avoiding them (by altering use or fit of the article).

It is contemplated that in some embodiments a user could be provided with feedback through motor pulsing, which generates haptic feedback for the user in the form of vibrations/sounds. Such provisions could facilitate operation of a tensioning system directly, or provide haptic feedback for other systems in communication with a motorized tensioning device.

Various methods of automatically operating a motorized tensioning device in response to various inputs can be used. For example, after initially tightening a shoe, it is common for the lace tension to quickly decline in the first few minutes of use. Some embodiments of a tensioning system may include provisions for readjusting lace tension to the initial tension set by the user. In some embodiments, a control unit may be configured to monitor tension in those first minutes to then readjust tension to match original tension.

Figure 39:
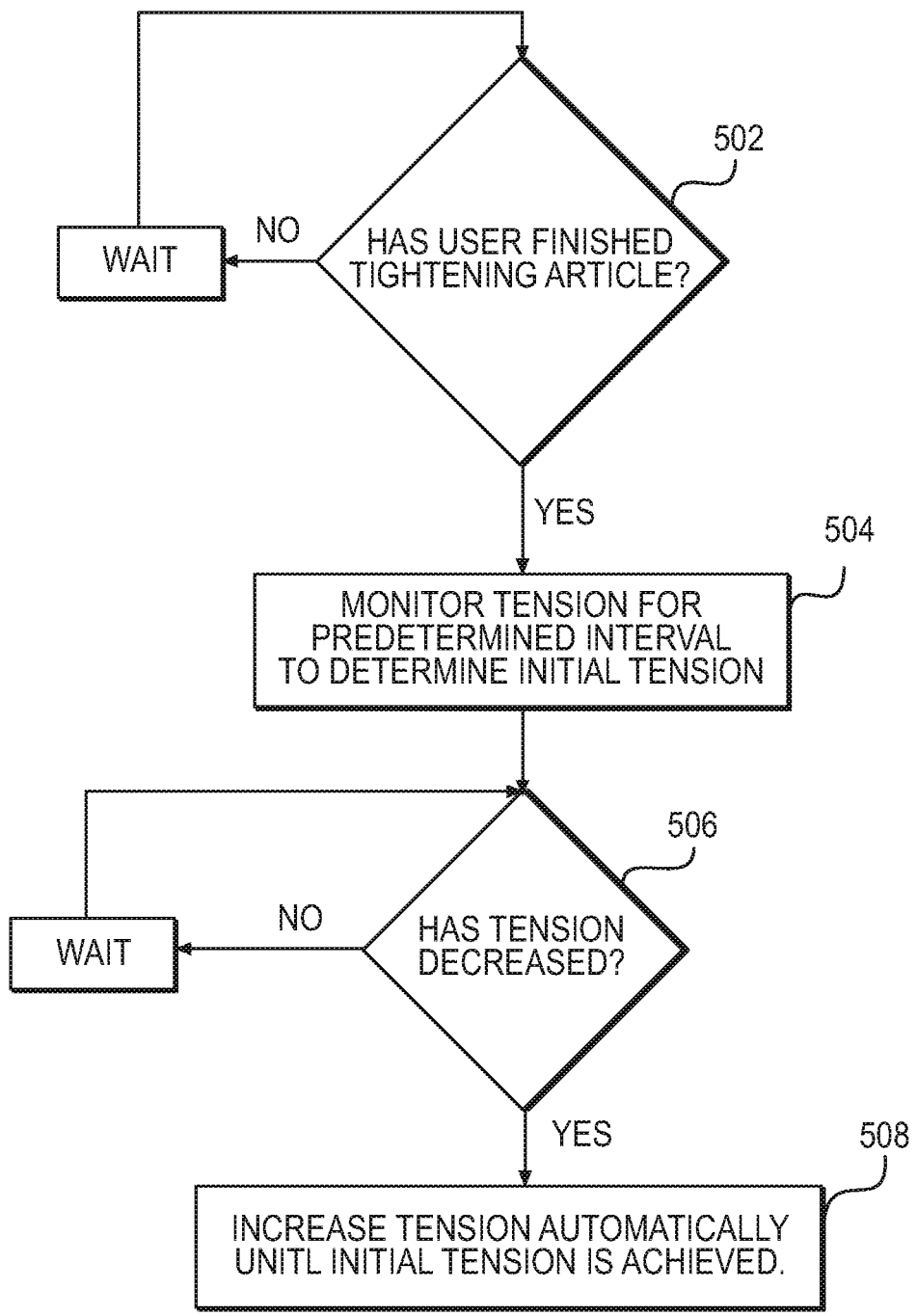
FIG. 39 is a schematic process for automatically controlling tension in an article to maintain an initial tension.

FIG. 39 is a schematic view of an exemplary process for automatically readjusting lace tension to maintain the user desired tension over time. In some embodiments, some of the following steps could be accomplished by a control unit 302 (see FIG. 5) associated with motorized tensioning device 160. In other embodiments, some of the following steps could be accomplished by other components of a tensioning system. It will be understood that in other embodiments one or more of the following steps may be optional.

In step 502, control unit 302 may determine if a user has finished tightening an article. In some cases, control unit 302 may determine that a user has finished tightening a lace if no control commands (e.g., an incremental tighten command) have been received after a predetermined period of time. If control unit 302 determines that the user has finished tightening the article, control unit 302 proceeds to step 504. Otherwise, control unit 302 may wait until it has been determined that the user has finished tightening the article.

In step 504, control unit 302 may monitor tension of the tensioning system (e.g., tension of a lace) for a predetermined interval to determine an initial tension. Methods for monitoring tension, including current sensors and other sensors have been previously discussed above. In some cases, control unit 302 may set the average measured tension over the predetermined interval as the initial tension.

Next, in step 506, control unit 302 may determine if the tension of the tensioning system has decreased. If not, control unit 302 may wait and then revaluate if the tension has decreased. Once it has been determined that the tension has decreased, control unit 302 may proceed to step 508. In step 508, control unit 302 may automatically increase the tension of the tensioning system until the initial tension has been achieved. In some embodiments, after step 508, control unit may wait and again automatically evaluate the tension at step 506. In some embodiments, control unit 302 may be additionally configured to automatically detect overtension and in response automatically decrease the tension of the tensioning system until the initial tension has been achieved. In some embodiments, control unit 302 may be configured to perform cyclic changes in tension, such as to enhance blood circulation.

In some embodiments, instead of only waiting a determined period of time, as illustrated in FIG. 39 and described above, the reevaluation of step 506 may be triggered by sensor information. In one example, sensor-based triggering may replace the waiting, with sensor information causing reevaluation of tension to occur. In another example, waiting may be performed as illustrated in FIG. 39, but with sensor information possibly causing the waiting to be terminated and triggering reevaluation of tension. Sensors providing such information to control unit 302 might include, but are not limited to, pressure sensors in shoe insoles to detect standing and/or rate of motion, bend indicators, strain gauges, gyroscopes, and accelerometers. In some embodiments, instead of or in addition to maintaining an initial tension, the sensor information may be used to establish a new target tension. For example, pressure sensors could be used to measure contact pressures of the upper of an article of footwear against the foot of a wearer and automatically adjust to achieve a desired pressure. In some embodiments, control unit 302 may be configured to store sensor information obtained over a period of time to identify triggering events. Additionally, control unit 302 may be configured to upload or otherwise provide stored sensor information to a remote device. Uploaded sensor information may be reviewed and analyzed for purposes including, but not limited to, monitoring correlations between footwear tightness and athletic performance.

Some embodiments may be configured to operate in two or more different modes. For example, some embodiments could operate in a "normal mode" and a "game mode" (or similarly, a "sports mode" or "active mode"). In the normal mode, the electric motor would be powered down after tensioning in order to save battery life. In contrast, when the game mode is selected by a user, the tension of the system may be continuously monitored and adjusted for maximum performance though at the expense of battery life. By enabling a user to change between these two modes, a user can choose to optimize battery life or optimize performance depending on the needs of the situation. In some embodiments, multiple target tensions may be stored and returned to, for either of the "normal mode" or the "game mode," such as configuring a target tension for sport and a substantially different tension for leisure. In some embodiments, control unit 302 may be configured to frequently, but not continuously, monitor and adjust tension, so as to further extend battery life while achieving some of the benefit of a continuously monitored "game mode."

Figure 40:
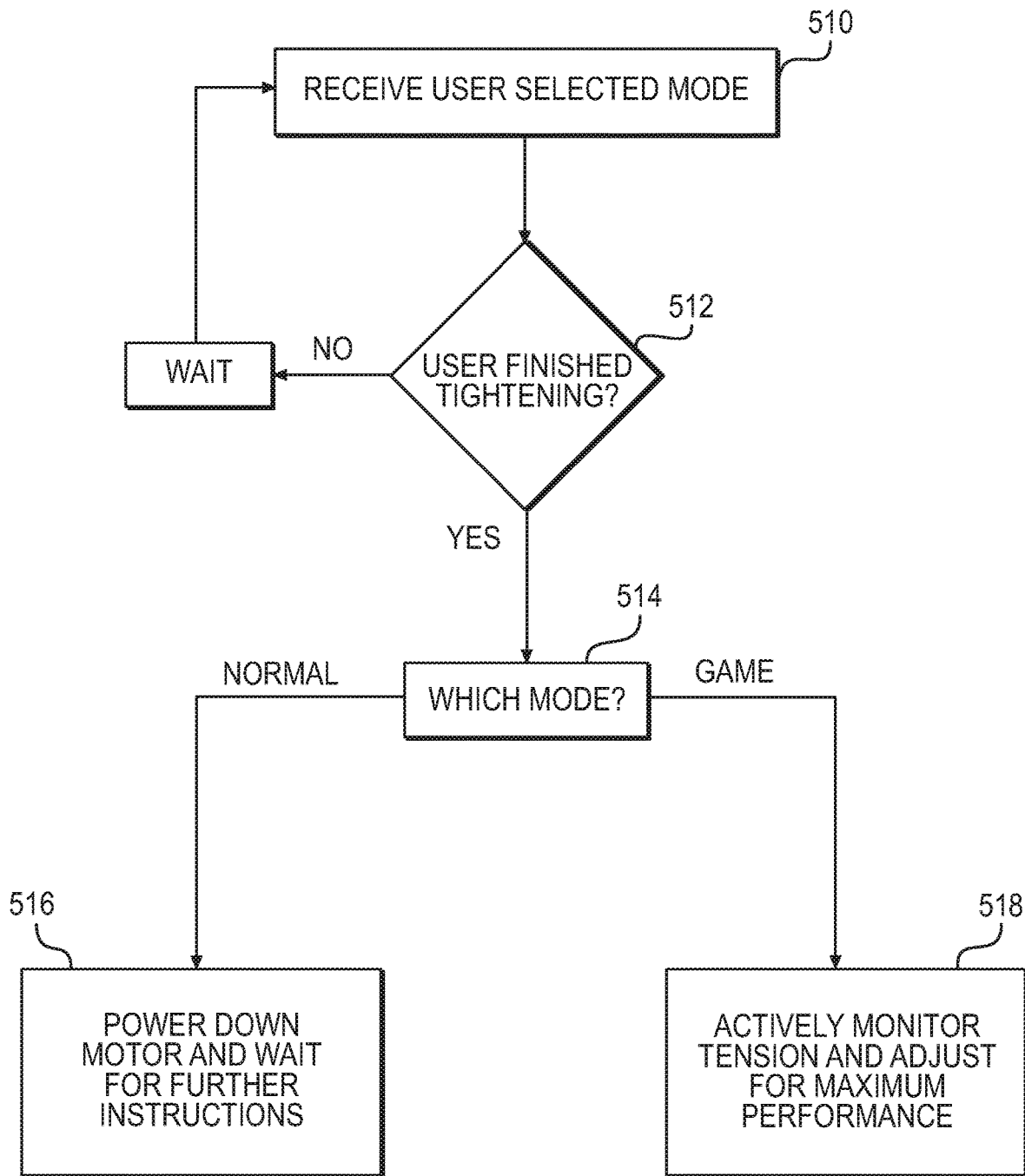
FIG. 40 is a schematic process for automatically controlling tension according to a user selected tensioning mode.

FIG. 40 is a schematic view of an exemplary process for operating a tensioning system in two different modes. In some embodiments, some of the following steps could be accomplished by a control unit 302 (see FIG. 5) associated with motorized tensioning device 160. In other embodiments, some of the following steps could be accomplished by other components of a tensioning system. It will be understood that in other embodiments one or more of the following steps may be optional.

In step 510, control unit 302 may receive the user selected mode. This may be determined by receiving a signal from a remote device, which may prompt a user to select with a "normal mode" or a "game mode". Next, in step 512, control unit 302 may determine if the user has finished tightening the article. If not, control unit 302 waits until the user has finished tightening the article. When the user has finished tightening the article, control unit 302 proceeds to step 514. At step 514, control unit 302 determines which mode has been selected from the information received during step 510. If the user has selected the normal mode, control unit proceeds to step 516, where the motor is powered down and the system awaits further instructions from the user (or other systems/sensors) to save battery power. If, however, the user has selected the game mode at step 514, control unit 302 proceeds to step 518. During step 518, control unit 302 may actively monitor the tension of the article and may automatically adjust the tension to achieve maximum performance.

As another example of a process for automatically controlling a tensioning system, GPS feedback from a remote device could be used to determine if a runner is on flat ground, climbing or descending. The system could automatically adjust the tension of the laces in footwear automatically, for example, by increasing tension in the laces during descent.

Methods of digitally tracking tensioning data measured by one or more sensors could be used in some embodiments. The average tension of the device could also be tracked. This tension data may be used to measure performance parameters, such as loading on the foot during an athletic activity. In some embodiments, such tension monitoring may be used to measure swelling. In addition, in some cases, the number of times the footwear is put on and taken off can be tracked. In addition, time of use could also be tracked. Data collection could be facilitated by various technologies including USB devices, data cords and blue tooth communication technologies. Moreover, the data collected can be transmitted through a variety of technologies to either a central database for evaluation.

Although the exemplary methods described above and shown in FIGS. 39 and 40 are directed to footwear, it will be understood that similar methods could be used for automated operation of other kinds of articles including tensioning systems. In particular, these methods could be used with any type of apparel.

Figure 41:
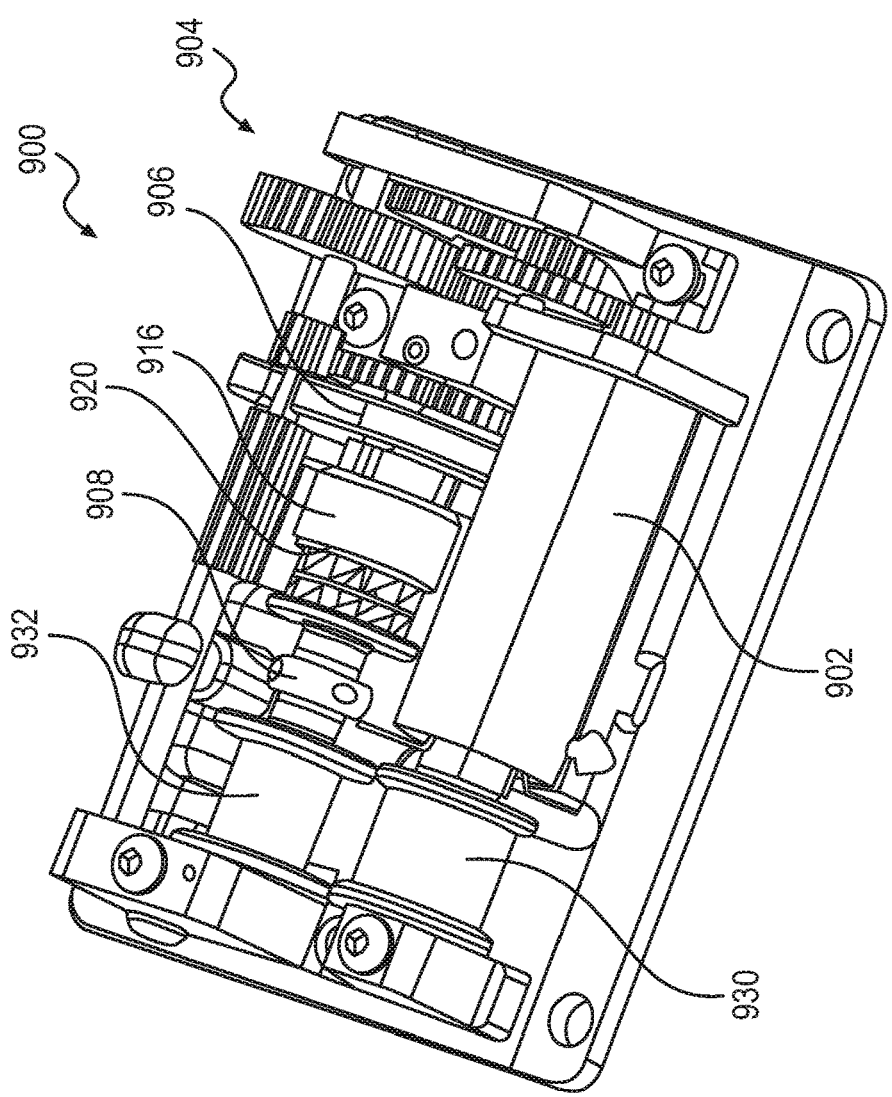
FIG. 41 is a schematic isometric view of an alternative embodiment of a motorized tensioning device.
Figure 43:
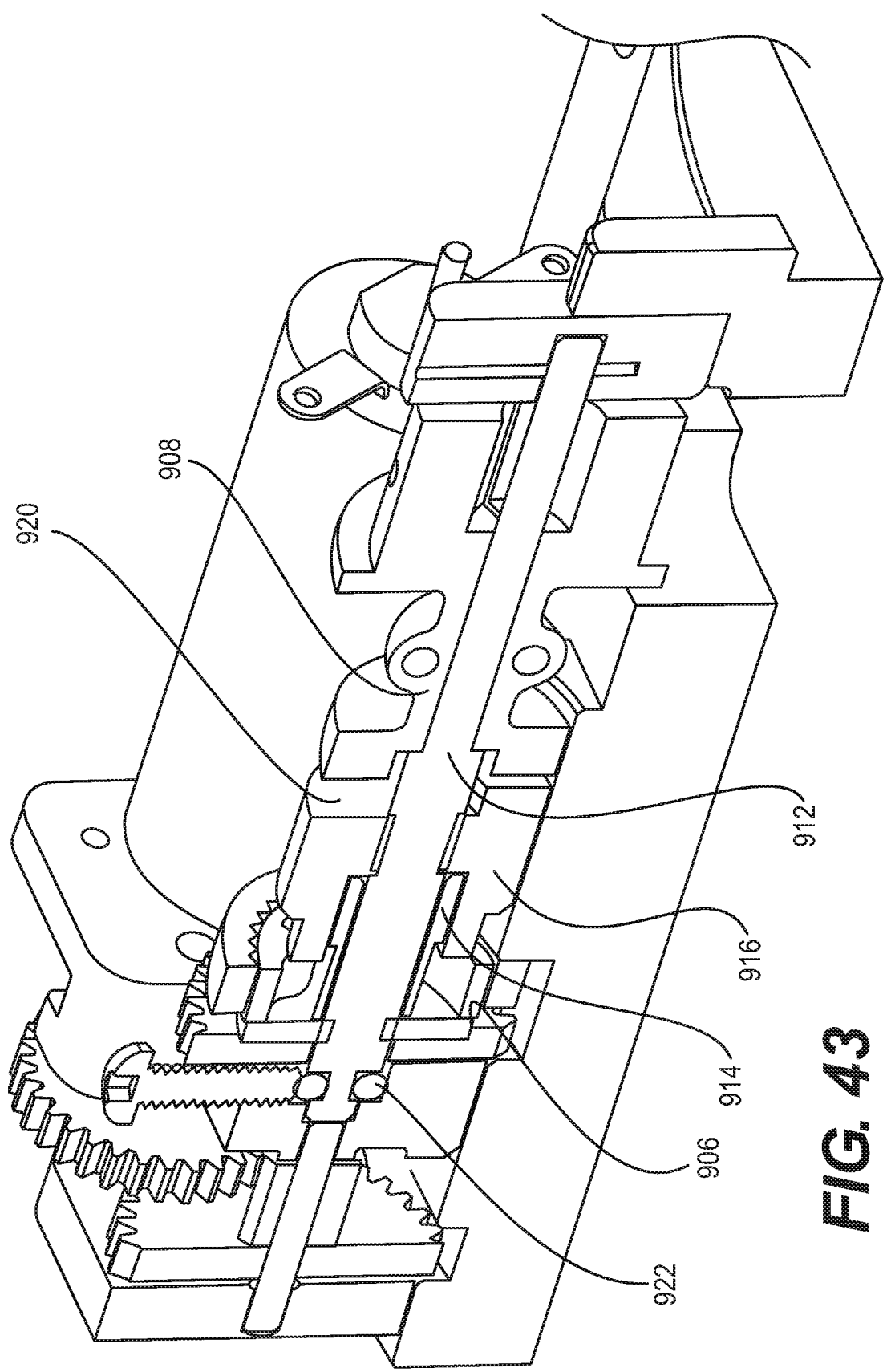
FIG. 43 is a cut-away view of an embodiment of a portion of a motorized tensioning device.

FIG. 41 shows a schematic view of an alternative embodiment of a motorized tensioning device 900. For purposes of describing some internal components, FIG. 43 illustrates a cross sectional view of some components of motorized tensioning device 900. Motorized tensioning device 900 may include some similar provisions as the previous embodiments, for example a motor 902 and a gear reduction system 904 that is driven by motor 902, Gear reduction system 904 as shown here includes 5 stages of spur gears. Other gear reductions that could be employed include: cycloidal, harmonic, and planetary. In some embodiments, the motor 902 and gear reduction system 904 combination may be sized to maximize the tradeoffs between current requirement, size, torque and speed. In the embodiment shown, the gear reduction is approximately 600:1 with an output RPM of 30 and a peak current of 1.2 amps.

Figure 42:
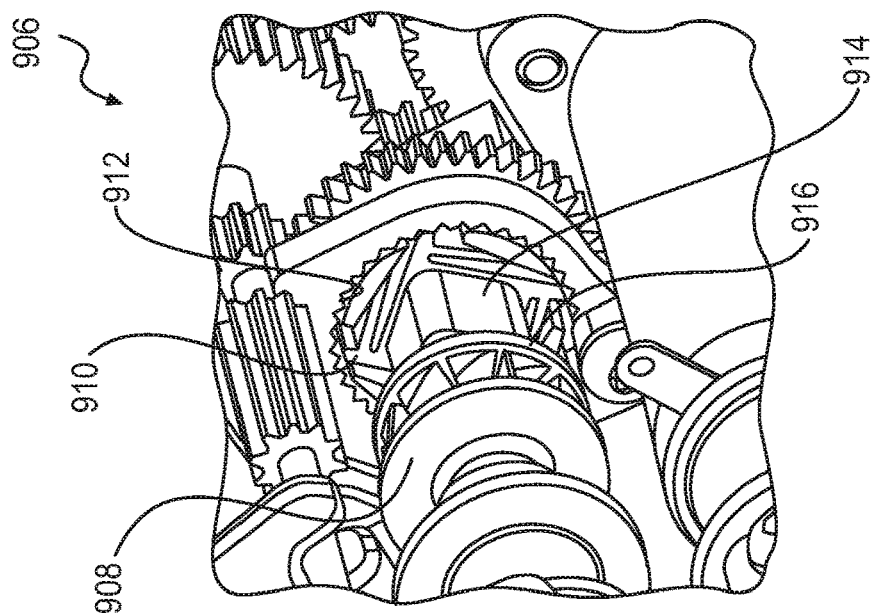
FIG. 42 is an enlarged isometric view of a load-holding mechanism of the motorized tensioning device of FIG. 41.

The output of gear reduction system 904 may enter an incrementally releasable load holding mechanism 906, which is shown in FIG. 42. This load holding mechanism 906 comprises a ratcheting type mechanism, which helps hold any loads applied to spool 908 without potentially back driving motor 902 and/or gear reduction system 904. The purpose is to hold the load without relying on the motor/gearbox to not back drive. Load holding mechanism 906 may hold load on spool 908 even while motor 902 is de-energized. When a small amount of lace tension is desired to be released, motor 902 unwinds and a sweeper element sweeps pawl elements 910 off internal teeth 912 allowing the output to unwind one tooth. This can be repeated as desired to precisely unwind the spool and correspondingly relax lace tension. This is important to allow the user to get to a precise fit. An exemplary load holding mechanism that may be used is disclosed in Soderberg et al., U.S. Patent Application Publication Number 2010/0139057, published Jun. 10, 2010 and titled "Reel Based Lacing System," the entire disclosure of which is incorporated herein by reference.

Referring to FIGS. 41 and 43, the output of load holding mechanism 906 in this embodiment is a male square drive 914. This drive element could be any number of sides or be an external spline. The male square drive mates with a female element 916 with sufficient clearance and of a material for low friction sliding along shaft 912 (see FIG. 43). The female element 916 is driven by the male square drive 914. The opposite end of female element 916 includes a face driving element 920. In the embodiment shown, this is a large number of triangular teeth which can engage or disengage from matching teeth on one flange of spool 908. These teeth could be from as few as one to more than eight. To encourage engagement the teeth may be back drafted from 5 to 60 degrees. In some embodiments, the teeth may be angled at approximately 45 degrees.

The center of female element 916 has a thread (not shown) which can engage threaded portion of shaft 912. When motor 902 is driven in one direction element 916 moves axially as a result of the internal thread and engages the face teeth between itself and corresponding teeth on spool 908. Shaft 912, which is normally stationary, has a frictional element 922 to prevent rotation during axial travel and engagement. When engagement is complete and the face teeth are fully engaged, the external thread of shaft 912 will experience torque. Over a certain torque level, motor 902 and gear reduction system 904 will overcome the torsional friction element 922 and shaft 912 will turn. In the embodiment shown, frictional element 922 is an O-ring on shaft 912 that is contained in a housing. The O-ring pressure can be adjusted via a screw which can clamp down on the O-ring. In other embodiments, this torsion friction could be accomplished by a number of means. For example, in another embodiment, torsional friction could be done as a coulomb frictional device such as an adjustable face clutch for instance using steel or brass against nylon or other brake pad materials and adjustable via an axial spring tensioner. In other embodiments, torsional friction could also be done electrically via a particle clutch or hydraulically via a rotary damper. In some embodiments, the number of turns to reach disengagement can be coordinated if desired with the number of turns to go from full lace tension to no tension. That way, incremental release can be done anywhere in the range of lace that is tensioned.

In the embodiment shown, rapid slack wind may be achieved via a constant force spring (not shown) that is stored on a freewheeling spool 930 and rewound onto one end 930 of spool 908.

In some embodiments, the lace may exit and is tended through radiused eyelets in a housing to prevent lace wear and increase lace fatigue life. In some embodiments, these exits may be located at least ½ of the spool diameter away from the spool to help the lace more or less level wind onto the spool to maximize capacity.

In some embodiments, a user initiated manual release element is also provided should the user every find themselves in tightened shoes with no remaining battery life. Many approaches could be used to manually disengage the spool from the load holding and motor/gearbox mechanism. For instance a tapered blade (not shown) can be inserted between the teeth on spool 908 and element 916 to separate them via a spring element allowing axial movement of spool 908 in the separation direction.

Figure 44:
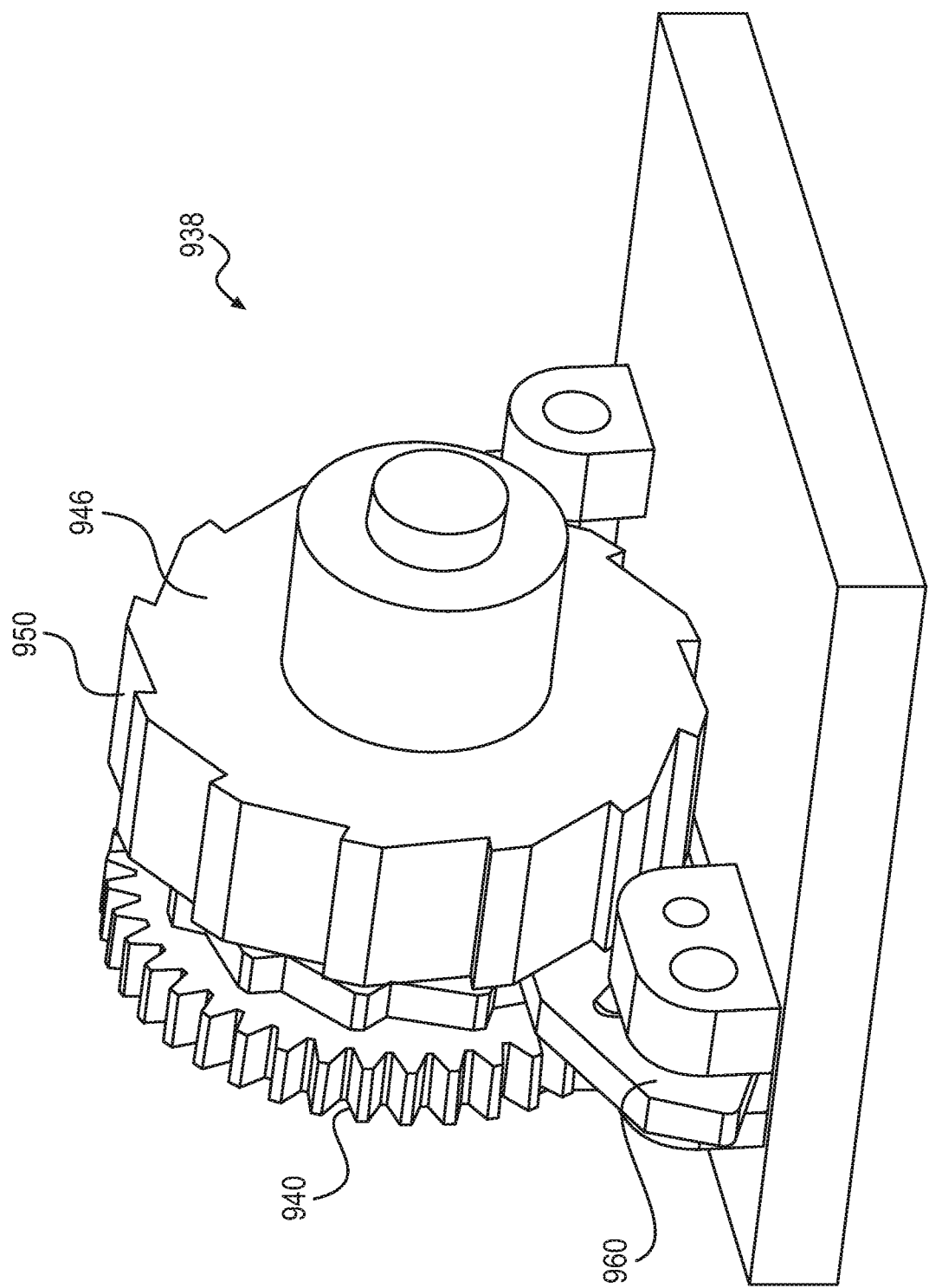
FIG. 44 is an isometric view of another embodiment of a load holding mechanism for a motorized tensioning device.
Figure 45:
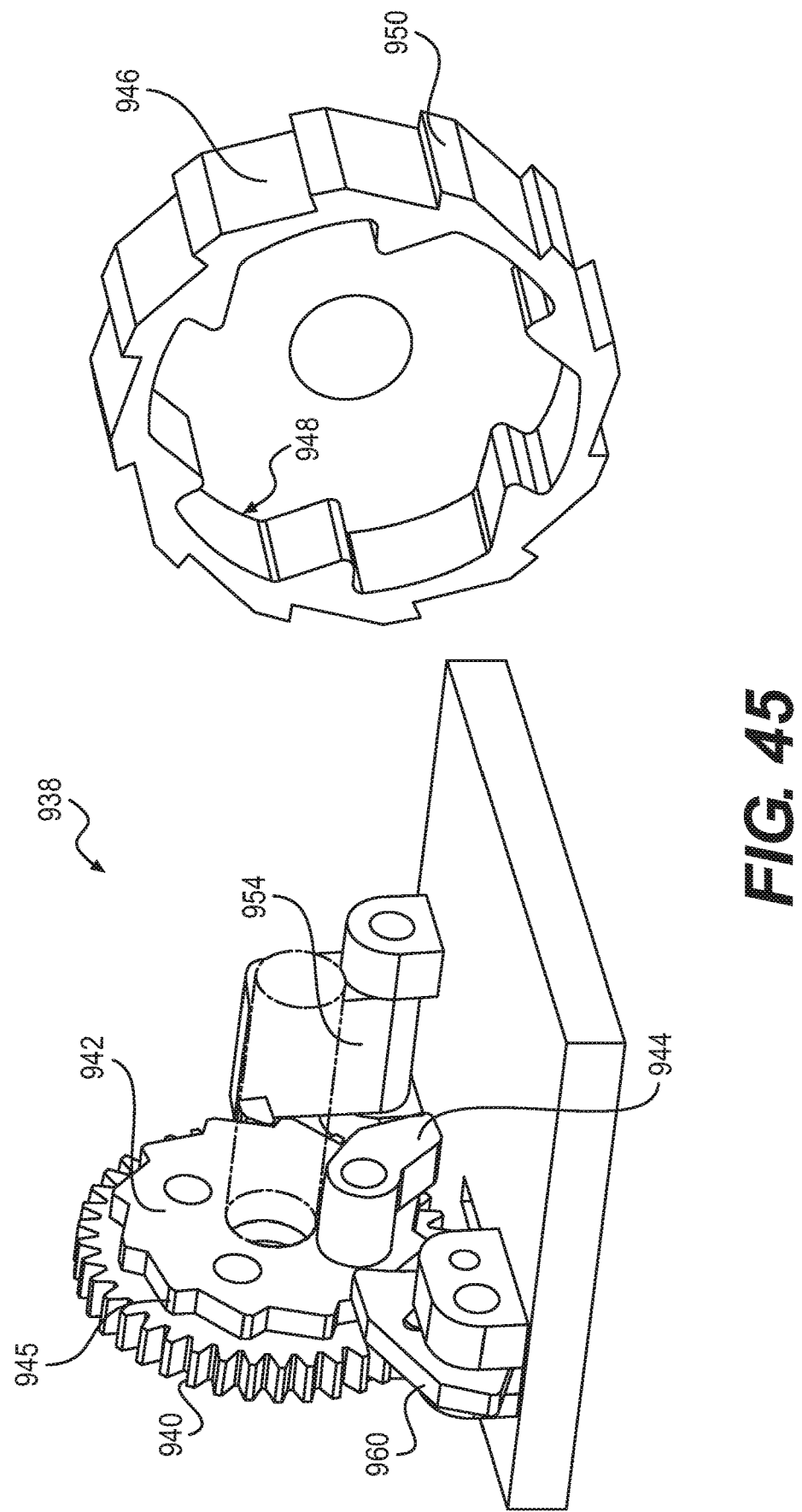
FIG. 45 is an isometric view of the load holding mechanism of FIG. 44, in which an output ring has been removed.

FIGS. 44 and 45 illustrate schematic views of an alternative tensioning and release mechanism that could be used with a motorized tightening system. For purposes of reference, this mechanism is shown in isolation from other components of a tightening device. This mechanism can be used for accomplishing tightening, load holding, incremental release and full release.

In this design, a system of cams and latches are used. Referring to FIGS. 44 and 45, load holding mechanism 938 includes a final stage output gear 940 of a gear reduction system (not shown) which is connected to a cylindrical plate 942 that has a single driving pawl 944 near its center. In the tightening direction, the motor is continually driven and the pawl 944 drives via detents in an output ring 946 that is attached to the spool. This output ring 946 has internal detents 948 that plate 942 drives and external female teeth 950 that engage an external load holding pawl 954. When the motor is stopped the external load holding pawl 954 resists the spool torque. It can be seen that plate 942 not only has the internal drive pawl 944 but also has cam elements 945 on its periphery that periodically disengage the external load holding pawl 954. When stopped and holding load the external pawl is engaged 954. Then the cylindrical plate 942 begins to back up for an incremental release. At first the output does not release. Then one of cam elements 945 on plate 942 releases outside load holding pawl 954. When this happens, output ring 946 catches up to pawl 954 and next the load holding pawl 954 engages and the mechanism stops in an incremental load holding position. In this way incremental release is accomplished. For this to operate a limit switch is employed to monitor plate 942 and stop in each incremental release position. In the embodiment shown there are six stop positions or every 60 degrees of rotation. This number can vary based on space requirements and the incremental lace release resolution desired. There could be as few as 1 stop per revolution and as many as 12, for example.

For full release, mechanism 938 must be stopped with both the internal and external pawl released at the same time. There is one more releasing pawl 960 required to accomplish this. In the figure, pawl 960 has three positions. Fully retracted, actuator extended, and releasing cam extended. After tensioning, pawl 960 is fully retracted. As incremental releases are actuated, the internal pawl 944 will likely pass this external pawl 960 and set it to the full release position. So when a full release is commanded, the internal pawl 944 will move into a position where both internal and external pawls are lifted and the user can freely extract lace and take off the article while only encountering minimal resistance which is provided by the slack take up mechanism.

Figure 46:
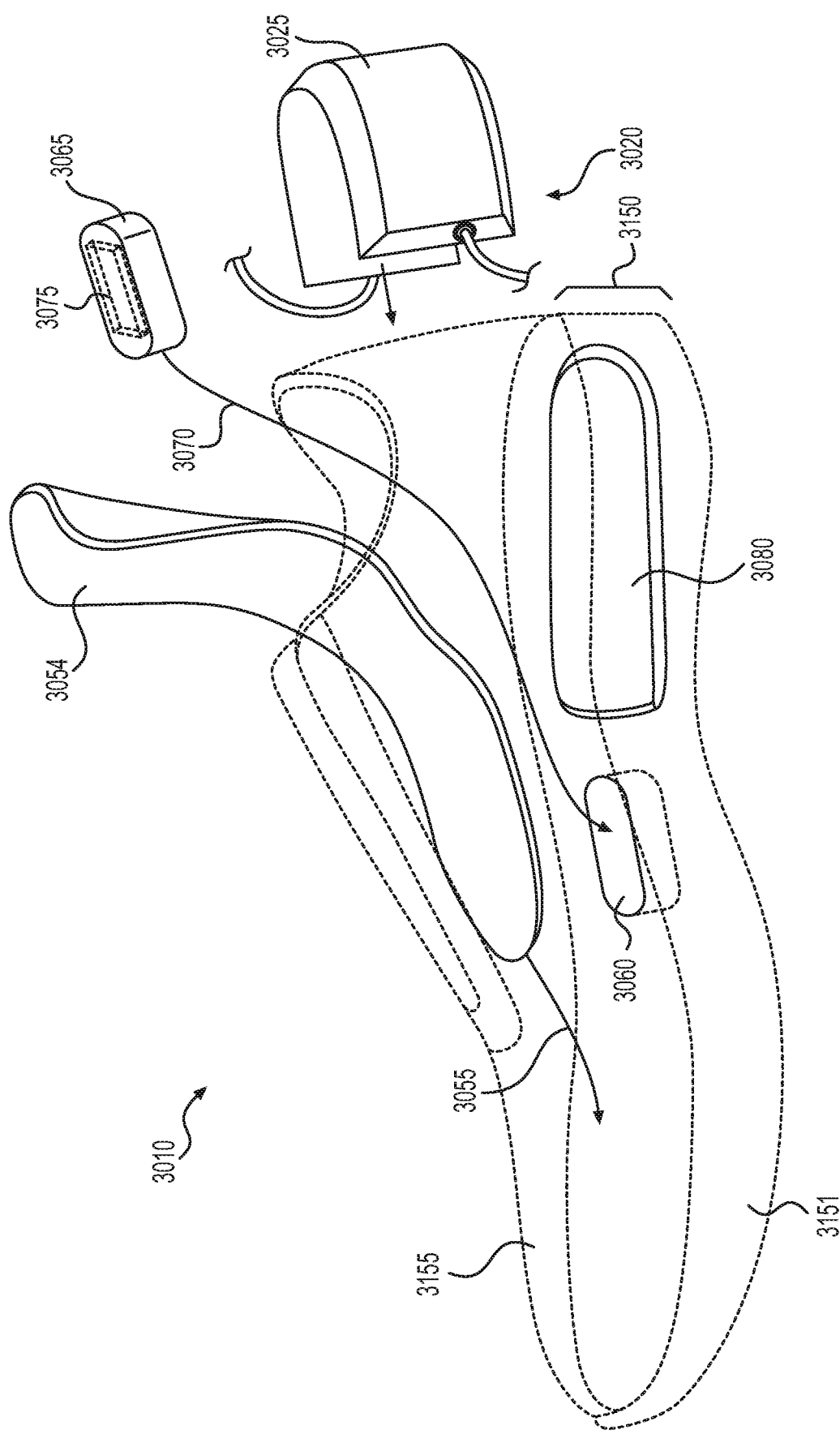
FIG. 46 is a schematic view of an article of footwear having an attachable tensioning system and showing select components of a sole structure of the footwear.

FIG. 46 illustrates an exemplary embodiment of an article of footwear 3010 including an upper 3155 and a sole structure 3150 secured to upper 3155. In some embodiments, sole structure 3150 may include a midsole 3151 and an insole 3054. Insole 3054 may be removably inserted into footwear 3010, as illustrated by an arrow 3055.

FIG. 46 also shows a motorized tensioning system 3020, which may be removably attached to footwear 3010. Footwear 3010 and tensioning system 3020 may have the same or similar attributes as footwear and tensioning systems discussed above. For example, tensioning system may include a tightening device, power source, and other componentry in a housing 3025, which may be removably attached to upper 3155, for example, on a heel portion of footwear 3010.

In addition, footwear 3010 may include various additional components disposed in sole structure 3150. For example, in some embodiments, footwear 3010 may include a cushioning element 3080 in a heel portion of sole structure 3150. Cushioning element 3080 may be incorporated into midsole 3151. In some embodiments, cushioning element 3080 may include a chamber containing a pressurized fluid. In some embodiments, cushioning element 3080 may include a foam cushioning material.

In some embodiments, footwear 3010 may include a removable electronics device 3065 in the heel portion of sole structure 3150. Electronics device 3065 may be removably inserted into a recess 3060 in midsole 3151 beneath insole 3054, as indicated by an arrow 3070. Electronics device 3065 may include a data acquisition component 3075 configured to collect performance data. In some embodiments, footwear 3010 may include both cushioning element 3080 and electronics device 3065. For example, as shown in FIG. 46, cushioning element 3080 may be located in the heel region of midsole 3151 and electronics device 3060 may be located in the midfoot region of midsole 3151.

Because the forefoot region of midsole 3151 may have a height that is relatively minimal, the placement of cushioning element 3080 and electronics package 3060 in midsole 3151 may leave little room for additional componentry in sole structure 3150. Accordingly, the attachability of housing 3025 of tensioning system 3020 to an outer heel portion of upper 3155 may enable use of motorized tightening in footwear that includes componentry incorporated into midsole 3151.

Figure 47:
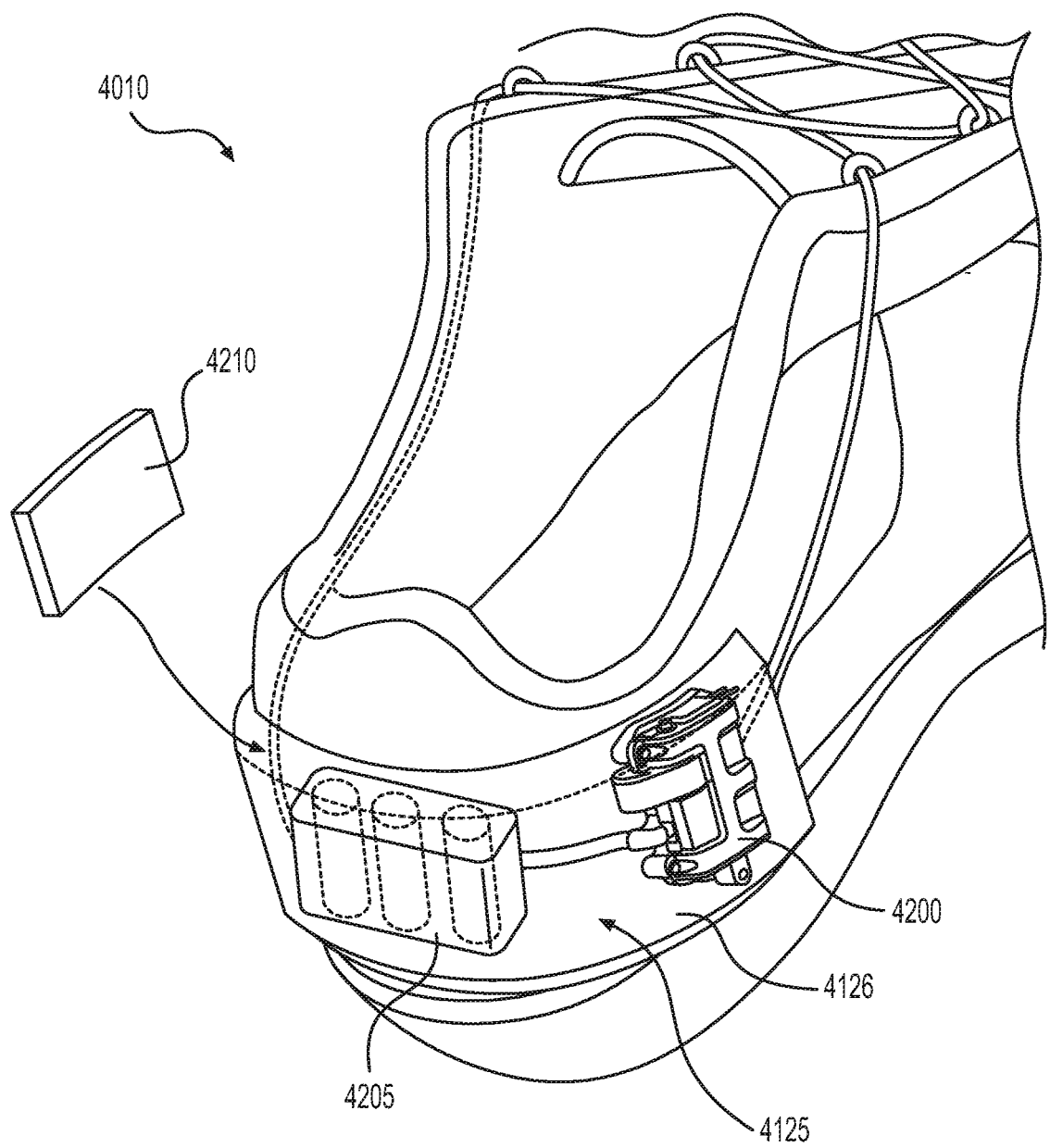
FIG. 47 is a schematic view of another embodiment of an article of footwear having an attachable tensioning system.

In some embodiments, the motorized tensioning system may incorporate a different arrangement of components. For example, as shown in FIG. 47, a motorized tensioning system 4125 may be removably attachable to an article of footwear 4010. The components and operation of tensioning system 4125 may be similar to other tensioning systems discussed above. For example, tensioning system 4125 may include a housing 4126 that is removably attachable to a heel portion of footwear 4010. In addition, housing 4126 may house a motorized tightening device 4200, a power source 4205 and a control unit 4210. However, in some embodiments, as shown in FIG. 47, tightening device 4200 may be disposed on a medial or lateral side of footwear 4010 when tensioning system 4125 is installed on footwear 4010. In addition, in some embodiments, as shown in FIG. 47, power source 4205 may be disposed in a rear-most portion of the heel portion of footwear 4010 when tensioning system 4125 is installed on footwear 4010. This arrangement may be advantageous in some cases, for example, when tightening device 4200 has a lower profile than power source 4205. It may be desirable to maintain a minimal width of tensioning system 4125, and thus, it may be preferred to house a larger sized battery on the rear-most portion of the heel portion.

Figure 48:
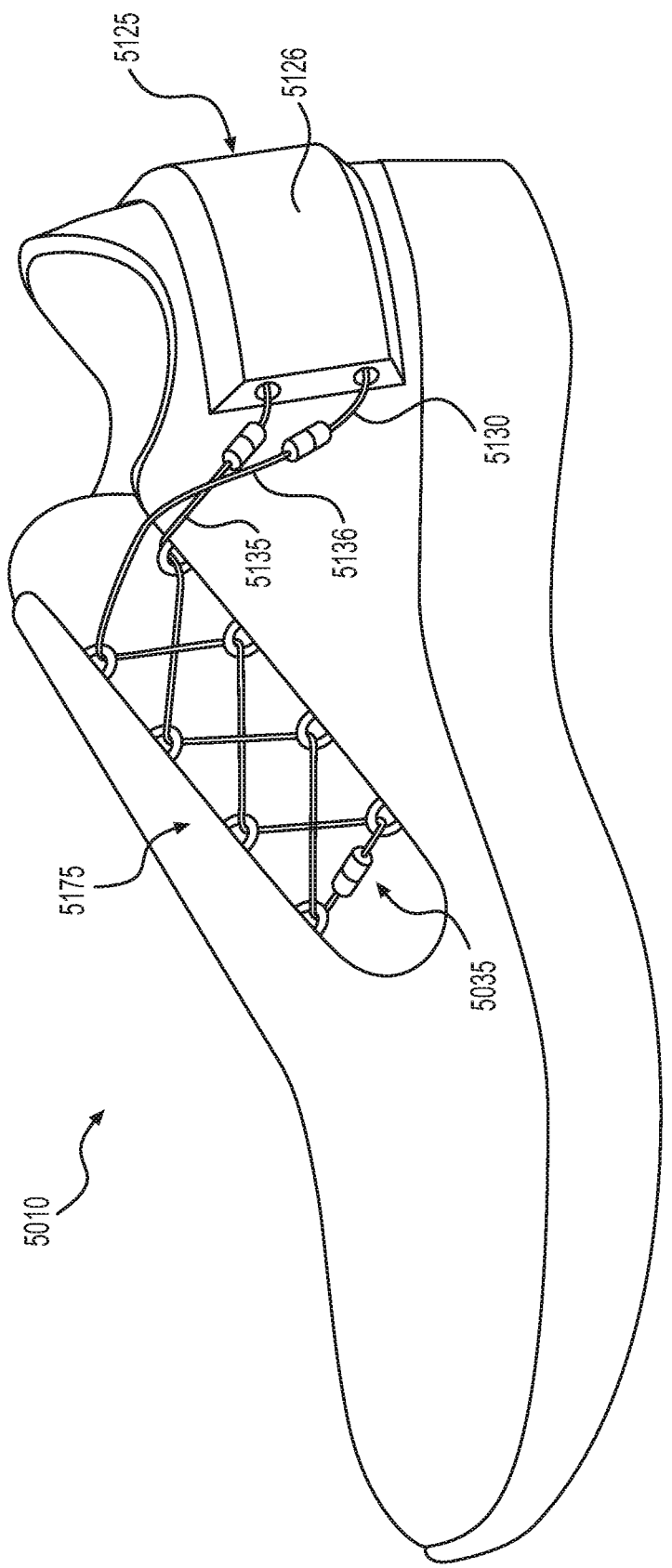
FIG. 48 is a schematic view of another embodiment of an article of footwear having an attachable tensioning system.

This arrangement may also be advantageous to operate alternative lacing arrangements. For example, as shown in FIG. 48, in some embodiments, an article of footwear 5010 may include a lacing region 5175 that is located on a medial or lateral side of footwear 5010. Such a lacing arrangement may provide improved fit, and may enable snug tightening without placing undue pressure on various portions of the foot, such as the instep region. In addition, locating lacing region 5175 away from the instep region may enable a relatively smooth surface of footwear 5010 to be presented in the instep region. This smooth surface may be desirable for soccer, to improve kicking accuracy and prevent impact of uneven materials with the foot.

A motorized tensioning system 5125 may be removably attachable to footwear 5010, and may include similar components to the tensioning systems discussed above. For example, tensioning system 5125 may include a motorized tightening device, a power source, and a control unit housed within a housing 5126. Tensioning system 5125 may also include a tensile member. The tensile member may include multiple portions connectible with manual couplings, such as connector 5035. For example, the tensile member may include a first tensile member portion 5130 associated with housing 5126. In addition, the tensile member may include a second tensile member portion 5135 and a third tensile member portion 5136, which may be laced through lacing region 5175. Because both ends of first tensile member portion 5130 may enter housing 5126 on the same side of footwear 5010, it may be desirable to locate the tightening device on the side of footwear 5010 nearest the entry point of first tensile member portion 5130.

Motorized tensioning systems that are heel-mounted may enable other lacing configurations to be used. For example, because the lace tension in a heel-mounted tensioning system is being applied from the heel region, and because the tensioning is automated, the lacing region need not be exposed. Accordingly, concealed lacing systems may be used. For example, in some embodiments, a lacing system is envisaged in which the lacing region is underfoot in the sole structure of the shoe.

Figure 49:
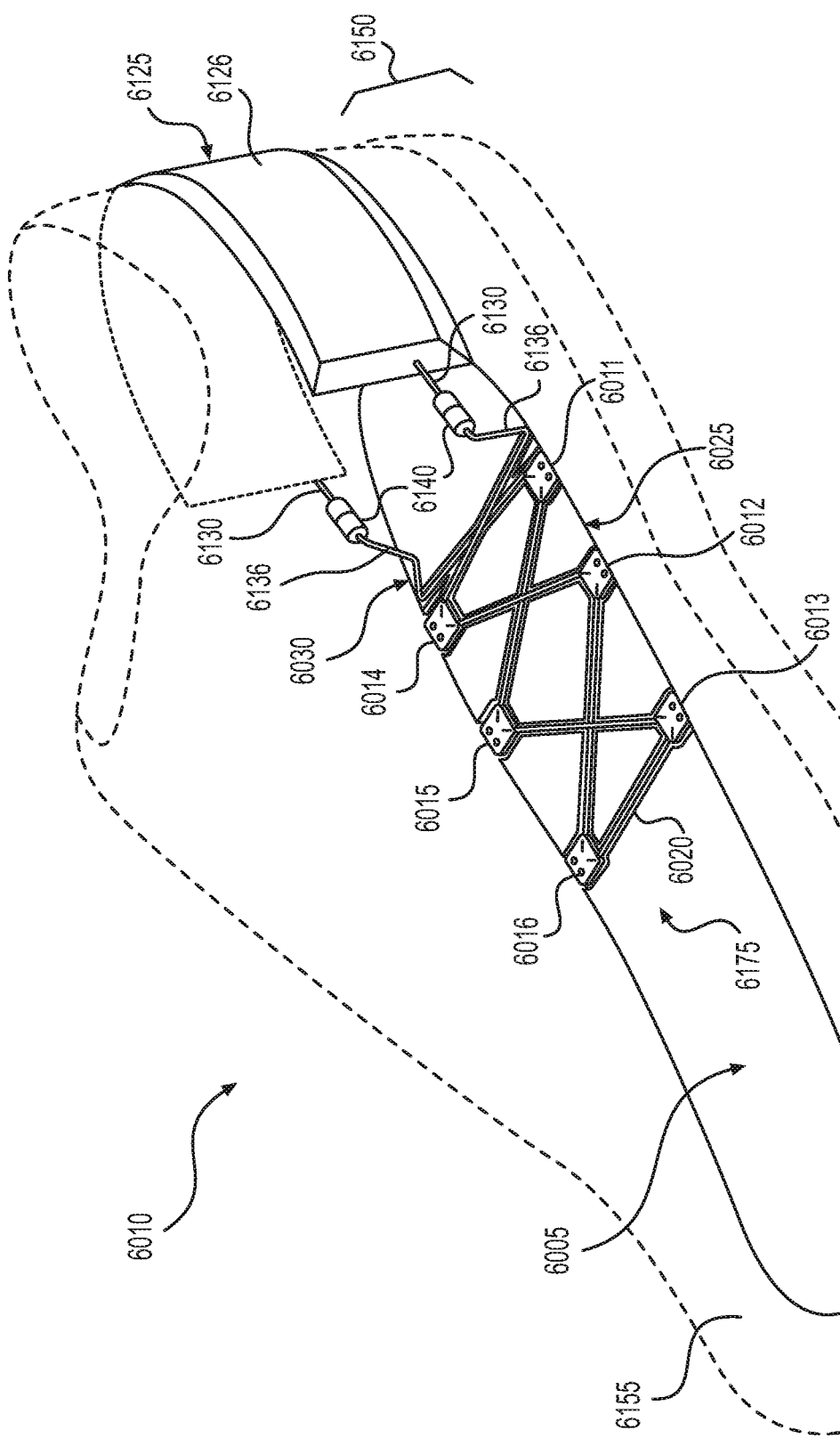
FIG. 49 is a schematic view of another embodiment of an article of footwear having an attachable tensioning system.

FIG. 49 shows an article of footwear 6010. Footwear 6010 may include a sole structure 6150 and an upper 6155 secured to sole structure 6150. In addition, FIG. 49 shows a motorized tensioning system 6125. Tensioning system 6125 may be removably attachable to footwear 6010, and may include similar components to the tensioning systems discussed above. For example, tensioning system 6125 may include a motorized tightening device, a power source, and a control unit housed within a housing 6126. Tensioning system 6125 may also include a tensile member. The tensile member may include multiple portions connectible with manual couplings. For example, the tensile member may include a first tensile member portion 6130 associated with housing 6126. In addition, the tensile member may include a second tensile member portion 6136 which may be laced into a lacing region 6175. Second tensile member portion 6136 may be removably attached to first tensile member portion 6130 by manual couplings 6140. Accordingly, housing 6126 and its contents, as well as first tensile member portion may be replaced due to the removability of housing 6126 from upper 6155 and manual couplings 6140.

As shown in FIG. 49, lacing region 6175 may be located internally, for example, in a footbed 6005 of sole structure 6150. Second tensile member portion 6136 may enter sole structure 6150 proximate a first peripheral edge 6025 and a second peripheral edge 6030 of footbed 6005. Further, second tensile member portion 6136 may be disposed in a groove 6020 in footbed 6005. Second tensile member portion 6136 may extend between anchor members that are located proximate first peripheral edge 6025 and second peripheral edge 6030 of footbed 6005. For example, a first anchor member 6011, a second anchor member 6012, and a third anchor member 6013 may be located proximate first peripheral edge 6025. In addition, a fourth anchor member 6014, a fifth anchor member 6015, and a third anchor member 6016 may be located proximate second peripheral edge 6030. These anchor members may be secured to upper 6155. When tensioning system 6125 applies tension to the tensile member, second tensile member portion 6136 may draw the anchor members closer to one another, thus tightening upper 6155 around the foot. Additional details of exemplary footbed lacing systems are provided in Baker et al., U.S. Pat. No. 8,387,282, issued Mar. 5, 2013, and entitled "Cable Tightening System for an Article of Footwear," the entire disclosure of which is incorporated herein by reference.

While various embodiments of the invention have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. An article of footwear, comprising:
   an upper;
   a sole structure, coupled to the upper;
   a lacing system, secured to at least one of the upper and the sole structure, comprising:
   a spool configured to rotate about a central axis, the spool comprising a shaft and at least one dividing portion on the shaft extending along the central axis, a first lace winding region and a second lace winding region along the shaft being separated by the dividing portion, wherein the at least one dividing portion includes a lace receiving channel enclosed by and extending through the dividing portion, the lace receiving channel being accessible via an aperture positioned on the dividing portion radially away from the shaft; and
   a lace, extending through the lace receiving channel and winding about each of the first and second lace winding regions and extending through the upper, wherein increasing tension on the lace increases tension on the upper;
   wherein the spool is configured to increase tension on the lace by increasing the winding of the lace around the first and second lace winding regions.

2. The article of footwear according to claim 1, wherein the spool rotates about the central axis in a first rotational direction to wind the lace to tighten the tensioning system.

3. The article of footwear according to claim 2, wherein the spool rotates about the central axis in a second rotational direction that is opposite the first rotational direction to unwind the lace to loosen the tensioning system.

4. The article of footwear according to claim 3, wherein rotation in at least one of the first rotational direction and the second rotational direction is performed using a motor associated with the tensioning system.

5. The article of footwear according to claim 3, wherein rotation in the second rotational direction is performed by applying tension to the lace while the tensioning system is in a loosened condition.

6. The article of footwear according to claim 1, wherein the dividing portion extends radially outward from the shaft; and
   wherein the lace receiving channel is spaced apart from the shaft.

7. The article of footwear according to claim 1, wherein the lace receiving channel is located adjacent to a perimeter edge of the dividing portion.

8. An article of footwear, comprising:
   an upper;
   a sole structure, coupled to the upper;
   a lacing system, secured to at least one of the upper and the sole structure, comprising:
   a motor;
   a spool in communication with the motor, the spool comprising a shaft and at least three dividing portions disposed along the shaft and extending along a central axis of the spool; and a lace, wherein a portion of the lace extends through a lace receiving channel enclosed by and extending through a center dividing portion to interconnect the lace with the spool, the lace receiving channel, the lace receiving channel being accessible via an aperture positioned on the central dividing portion radially away from the shaft, wherein the lace extends through the upper, wherein increasing tension on the lace increases tension on the upper; and wherein the lace is configured to be wound around portions of the shaft disposed on opposite sides of the center dividing portion when the lacing system is in a tightened condition.

9. The article of footwear according to claim 8, wherein equal portions of the lace are disposed on opposite sides of the center dividing portion when the tensioning system is in the tightened condition.

10. The article of footwear according to claim 8, wherein equal portions of lace are unwound from opposite sides of the center dividing portion when the tensioning system is placed in a loosened condition from the tightened condition.

11. The article of footwear according to claim 8, wherein the lace receiving channel is chamfered around a circumference of the lace receiving channel.

12. The article of footwear according to claim 8, wherein the lace is configured to slide through the lace receiving channel to adjust tension in different portions of the tensioning system.

13. The article of footwear according to claim 12, wherein tension of the tensioning system in at least one of a midfoot region and a forefoot region of an article of footwear is adjusted by changing an amount of a first portion of the lace that is associated with the midfoot region and changing an amount of a second portion of the lace that is associated with the forefoot region.

14. The article of footwear according to claim 8, wherein the at least three dividing portions include a first end portion, the center dividing portion, and a second end portion; and wherein the center dividing portion is located on the shaft between the first end portion and the second end portion.

15. The article of footwear according to claim 14, wherein a first portion of lace is wound on a first shaft section disposed between the first end portion and the center dividing portion when the tensioning system is in the tightened condition; and wherein a second portion of lace is wound on a second shaft section disposed between the second end portion and the center dividing portion when the tensioning system is in the tightened condition.

16. An article of footwear, comprising:
an upper;
a sole structure, coupled to the upper;
a lacing system; secured to at least one of the upper and the sole structure, comprising:
a shaft; and
at least one dividing portion extending along a central axis of the shaft and radially outward from the shaft, forming a first lace winding region and a second lace winding region along the shaft being separated by the dividing portion;
wherein the at least one dividing portion includes a lace receiving channel enclosed by and extending through the dividing portion, the lace receiving channel being accessible via an aperture positioned on the dividing portion radially away from the shaft, and wherein the shaft is configured to tighten the lacing system by increasing the winding of a lace around the first and second lace winding regions.

17. The article of footwear according to claim 16, further comprising at least three dividing portions forming the first lace winding region and the second lace winding region; and
wherein a center dividing portion includes the lace receiving channel.

18. The article of footwear according to claim 16, further comprising a first end and a second end disposed at opposite ends along the central axis of the shaft; and
wherein the shaft includes a screw disposed at the second end.

19. The article of footwear according to claim 18, wherein the screw is configured to receive a gear in communication with a motor of a tensioning system to rotate the shaft about the central axis.

20. The article of footwear according to claim 18, wherein the shaft is configured to receive a lace through the lace receiving channel; and
wherein rotation of the shaft about the central axis in a first rotational direction is configured to wind portions of the lace on opposite sides of the at least one dividing portion in the first and second winding regions divided by the at least dividing portion.

* * * * *

UNITED STATES PATENT AND TRADEMARK OFFICE
CERTIFICATE OF CORRECTION

| | |
|---|---|
| PATENT NO. | : 11,166,525 B2 |
| APPLICATION NO. | : 15/640282 |
| DATED | : November 9, 2021 |
| INVENTOR(S) | : Tiffany A. Beers |

It is certified that error appears in the above-identified patent and that said Letters Patent is hereby corrected as shown below:

On the Title Page

On page 4, in Column 2, under "Other Publications", Line 21, delete "Desicion" and insert --Decision-- therefor In the Claims In Column 40, Line 8, in Claim 16, delete "system;" and insert --system,-- therefor Signed and Sealed this
Thirteenth Day of September, 2022

Katherine Kelly Vidal
*Director of the United States Patent and Trademark Office*